US012458818B2

(12) United States Patent
Shan et al.

(10) Patent No.: US 12,458,818 B2
(45) Date of Patent: Nov. 4, 2025

(54) ANTI-TROPHOBLAST CELL SURFACE ANTIGEN 2 (TROP2) ANTIBODIES AND ANTIBODY DRUG CONJUGATES COMPRISING SAME

(71) Applicant: CSPC MEGALITH BIOPHARMACEUTICAL CO., LTD., Hebei (CN)

(72) Inventors: Yuxi Shan, Sacramento, CA (US); Lixin Feng, Sacramento, CA (US); Ryan Joseph Browde, Sacramento, CA (US); Lisha Allen, Sacramento, CA (US); Ru Bin Yang, Sacramento, CA (US)

(73) Assignee: CSPC MEGALITH BIOPHARMACEUTICAL CO., LTD., Hebei (CN)

( * ) Notice: Subject to any disclaimer, the term of this patent is extended or adjusted under 35 U.S.C. 154(b) by 966 days.

(21) Appl. No.: 17/437,423

(22) PCT Filed: Mar. 18, 2020

(86) PCT No.: PCT/US2020/023421

§ 371 (c)(1),
(2) Date: Sep. 9, 2021

(87) PCT Pub. No.: WO2020/191092

PCT Pub. Date: Sep. 24, 2020

(65) Prior Publication Data

US 2022/0153862 A1 May 19, 2022

Related U.S. Application Data

(60) Provisional application No. 62/820,831, filed on Mar. 19, 2019.

(51) Int. Cl.

| | |
|---|---|
| ***A61P 35/00*** | (2006.01) |
| ***A61K 39/00*** | (2006.01) |
| ***A61K 47/68*** | (2017.01) |
| ***C07K 16/30*** | (2006.01) |
| ***G01N 33/574*** | (2006.01) |

(52) U.S. Cl.

CPC .... *A61K 47/6851* (2017.08); *A61K 47/68031* (2023.08); *A61P 35/00* (2018.01); *C07K 16/30* (2013.01); *G01N 33/57492* (2013.01); *A61K 2039/505* (2013.01); *C07K 2317/24* (2013.01); *C07K 2317/73* (2013.01); *C07K 2317/92* (2013.01)

(58) Field of Classification Search

None

See application file for complete search history.

(56) References Cited

U.S. PATENT DOCUMENTS

2016/0296633 A1 10/2016 Goldenberg et al.

FOREIGN PATENT DOCUMENTS

| | | | |
|---|---|---|---|
| CN | 110903395 | A | 3/2020 |
| EP | 3088419 | A1 | 11/2016 |
| WO | 2010089782 | A1 | 8/2010 |
| WO | 2013068946 | A2 | 5/2013 |
| WO | 2016087651 | A1 | 6/2016 |
| WO | 2016172427 | A1 | 10/2016 |
| WO | 2019029715 | A1 | 2/2019 |

OTHER PUBLICATIONS

Scott et al., 2012, vol. 12. Nature Reviews, pp. 278-287.*
Chen, 2018, Friont. immunol. vol. 9: 1-7.*
Feb. 23, 2023 extended European Search Report issued in European Patent Application No. 20772616.7.
Bing Yao, et al., Selection of Payloads for Antibody-Drug Conjugates Targeting Ubiquitously Expressed Tumor-Associated Antigens: a Case Study, The AAPS Journal, May 27, 2022, 24(4):70.
Jun. 18, 2020 International Search Report issued in International Patent Application No. PCT/US2020/023421.
Jun. 18, 2020 Written Opinion of the International Searching Authority issued in International Patent Application No. PCT/US2020/023421.
Cubas et al. (2009) Biochimica et Biophysica Acta. 1796: 309-314.
Vidmar et al. (2013) Protein Exp and Pur. 91: 69-76.
Huang et al. (2005) Clin Cancer Res. 11: 4357-4364.
Shvartsur et al. (2015) Genes Cancer. 6: 84-105.
Guerra et al. (2008) Cancer Res. 68: 8113-8121.

(Continued)

*Primary Examiner* — Amy E Juedes
(74) *Attorney, Agent, or Firm* — Houston Beshining Law Office PLLC; Liangang Ye

(57) ABSTRACT

Provided are anti-Trophoblast cell surface antigen 2 (TROP2) antibodies and fragments thereof. Also provided are isolated nucleic acid molecules that encode anti-TROP2 antibodies, vectors comprising such nucleic acids, and host cells comprising such vectors or nucleic acids. Provided are methods of making anti-TROP2 antibodies. Also provided are antibody drug conjugates (ADCs) comprising an anti-TROP2 antibody and an active moiety (e.g., a therapeutic moiety such as a toxin) and methods of making anti-TROP2 ADCs. Also provided are related pharmaceutical compositions and methods using such pharmaceutical compositions in the treatment of disorders associated with aberrant TROP2 expression (e.g., cancer).

25 Claims, 7 Drawing Sheets

Specification includes a Sequence Listing.

(56) References Cited

OTHER PUBLICATIONS

Lin et al. (2012) EMBO Mol Med. 4: 472-485.
Zhang et al. (1997) Science. 276: 1268-1272.
Tsujikawa et al. (1999) Nat Genet. 21: 420-423.
Fong et al. (2008) Mod path. 21:186-191.
Muhlmann et al. (2009) J Clin Path. 62:152-158.
Wu et al. (2013) Head & Neck. 35:1373-1378.
Wang (2011) Mol Cancer Res. 9: 1686-1695.
Wang et al. (2008) Mol Cancer Ther 7: 280-285.
Aug. 23, 2023 Chinese First Office Action issued in Chinese Patent Application No. 2020800228543.
Nov. 21, 2024 European First Office Action issued in European Patent Application No. 20772616.7.

* cited by examiner

SEQUENCE LISTING

```
<160> NUMBER OF SEQ ID NOS: 105

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Asp Tyr Ser Ile Asn
1               5                   10


<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Gly Phe Ser Leu Thr Arg Tyr Gly Val His
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Tyr Thr Phe Thr Asp Tyr Ser Ile His
1               5                   10


<210> SEQ ID NO 4
```

<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Tyr Thr Phe Thr Asp Tyr Gly Met Asn
1 5 10

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

Trp Ile Gly Val Ile Ser Thr Tyr Tyr Gly Asp Ala Ser Tyr Asn Gln
1 5 10 15

Lys Phe

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Trp Leu Gly Val Ile Trp Ser Gly Gly Asn Thr Asp Tyr Asn Ala Ala
1 5 10 15

Phe

<210> SEQ ID NO 7
<211> LENGTH: 18
<212> TYPE: PRT
<213> ORGANISM: Artificial Sequence
<220> FEATURE:
<223> OTHER INFORMATION: Synthetic Construct

<400> SEQUENCE: 7

Trp Ile Gly Val Ile Ser Ser Tyr Tyr Gly Asp Ala Thr Tyr Asn Gln
1 5 10 15

Lys Phe

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8

Trp Ile Gly Leu Ile Ser Thr Tyr Tyr Gly Asp Ala Thr Tyr Thr Gln
1 5 10 15

Lys Phe

<210> SEQ ID NO 9
<211> LENGTH: 18
<212> TYPE: PRT
<213> ORGANISM: Artificial Sequence
<220> FEATURE:
<223> OTHER INFORMATION: Synthetic Construct

<400> SEQUENCE: 9

Trp Ile Gly Val Ile Ser Thr Phe Tyr Gly Asp Ala Asn Tyr Asn Gln
1 5 10 15

Lys Phe

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Ala Arg Tyr Gly Asp Gly Tyr Asn Gln Phe Asp Tyr
1 5 10

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Ala Arg Glu Asp Arg Tyr Val Gly Glu Phe Ala Tyr
1 5 10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Ala Leu Leu Gly Ala Tyr Asn Tyr Phe Asp Tyr
1 5 10

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Ala Arg Arg Gly Asn Tyr Asp Ser Met Asp Tyr
1 5 10

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

Glu Ser Val Asp Ser Tyr Gly Asn Asn Phe Met His
1 5 10

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

Glu Ser Val Asp Ser Tyr Gly Asn Ser Phe Ile His
1 5 10

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

Glu Ser Val Asp Ser Tyr Gly Asn Ser Phe Met His
1 5 10

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Leu Leu Ile Tyr Arg Ala Ser Asn Leu Glu Ser
1 5 10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Leu Leu Val Tyr Arg Ala Ser Asn Leu Glu Ser
1 5 10

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gln Ser Tyr Glu Asp Pro Tyr Thr
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Ser Asn Glu Asp Pro Arg Thr
1 5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

```
Gln Gln Ser Tyr Glu Asp Pro Pro Thr
1               5
```

<210> SEQ ID NO 22
<211> LENGTH: 119
<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Ile Asn Trp Val Lys Gln Ser His Ala Lys Ser Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Tyr Gly Asp Gly Tyr Asn Gln Phe Asp Tyr Trp Gly Gln Gly
            100                 105                 110

Thr Thr Leu Thr Val Ser Ser
        115
```

<210> SEQ ID NO 23
<211> LENGTH: 118
<212> TYPE: PRT
<213> ORGANISM: Artificial Sequence
<220> FEATURE:
<223> OTHER INFORMATION: Synthetic Construct

<400> SEQUENCE: 23

```
Glu Val Gln Leu Glu Gln Ser Gly Pro Gly Leu Val Gln Pro Ser Gln
1               5                   10                  15

Ser Leu Ser Ile Thr Cys Thr Val Ser Gly Phe Ser Leu Thr Arg Tyr
            20                  25                  30

Gly Val His Trp Val Arg Gln Ser Pro Gly Arg Ser Leu Glu Trp Leu
        35                  40                  45

Gly Val Ile Trp Ser Gly Gly Asn Thr Asp Tyr Asn Ala Ala Phe Ile
    50                  55                  60

Ser Arg Leu Thr Ile Thr Lys Asp Asn Ser Lys Ser Gln Val Phe Phe
65                  70                  75                  80

Lys Met Asn Ser Leu Gln Pro Asn Asp Thr Gly Val Tyr Tyr Cys Ala
                85                  90                  95

Arg Glu Asp Arg Tyr Val Gly Glu Phe Ala Tyr Trp Gly Gln Gly Thr
            100                 105                 110

Leu Val Thr Val Ser Ala
        115
```

<210> SEQ ID NO 24
<211> LENGTH: 118
<212> TYPE: PRT
<213> ORGANISM: Artificial Sequence
<220> FEATURE:

<223> OTHER INFORMATION: Synthetic Construct

<400> SEQUENCE: 24

Gln Val Gln Leu Gln Gln Ser Gly Ala Glu Leu Val Arg Pro Gly Val
1 5 10 15

Ser Val Lys Ile Ser Cys Lys Gly Ser Gly Tyr Thr Phe Thr Asp Tyr
20 25 30

Ser Ile His Trp Val Lys Gln Ser His Ala Lys Ser Leu Glu Trp Ile
35 40 45

Gly Val Ile Ser Ser Tyr Tyr Gly Asp Ala Thr Tyr Asn Gln Lys Phe
50 55 60

Lys Gly Lys Ala Thr Met Thr Val Asp Lys Ser Ser Ser Thr Ala Tyr
65 70 75 80

Met Glu Leu Ala Arg Leu Thr Ser Glu Asp Ser Ala Ile Tyr Tyr Cys
85 90 95

Ala Leu Leu Gly Ala Tyr Asn Tyr Phe Asp Tyr Trp Gly Gln Gly Thr
100 105 110

Thr Leu Thr Val Ser Ser
115

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Gln Gln Ser Gly Ala Glu Leu Val Arg Pro Gly Val
1 5 10 15

Ser Val Lys Ile Ser Cys Lys Gly Ser Gly Tyr Thr Phe Thr Asp Tyr
20 25 30

Ser Ile His Trp Val Lys Gln Ser His Ala Lys Ser Leu Glu Trp Ile
35 40 45

Gly Leu Ile Ser Thr Tyr Tyr Gly Asp Ala Thr Tyr Thr Gln Lys Phe
50 55 60

Lys Gly Lys Ala Thr Met Thr Val Asp Lys Ser Ser Ser Thr Ala Tyr
65 70 75 80

Met Glu Leu Ala Arg Leu Thr Ser Glu Asp Ser Ala Ile Tyr Tyr Cys
85 90 95

Ala Leu Leu Gly Ala Tyr Asn Tyr Phe Asp Tyr Trp Gly Gln Gly Thr
100 105 110

Thr Leu Thr Val Ser Ser
115

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Gln Gln Ser Gly Ala Glu Leu Val Arg Pro Gly Val
1 5 10 15

Ser Val Lys Ile Ser Cys Lys Gly Ser Gly Tyr Thr Phe Thr Asp Tyr
20 25 30

Gly Met Asn Trp Val Lys Gln Ser His Ala Lys Ser Leu Glu Trp Ile

```
        35                  40                  45

Gly Val Ile Ser Thr Phe Tyr Gly Asp Ala Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Arg Gly Asn Tyr Asp Ser Met Asp Tyr Trp Gly Gln Gly Thr
            100                 105                 110

Ser Val Thr Val Ser Ser
        115


<210> SEQ ID NO 27
<211> LENGTH: 111
<212> TYPE: PRT
<213> ORGANISM: Artificial Sequence
<220> FEATURE:
<223> OTHER INFORMATION: Synthetic Construct

<400> SEQUENCE: 27

Asp Ile Val Leu Thr Gln Ser Pro Ala Ser Leu Ala Val Ser Leu Gly
1               5                   10                  15

Gln Arg Ala Thr Ile Ser Cys Arg Val Ser Glu Ser Val Asp Ser Tyr
            20                  25                  30

Gly Asn Asn Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Met Glu Ala Asp Asp Val Ala Thr Tyr Tyr Cys Gln Gln Ser Tyr
                85                  90                  95

Glu Asp Pro Tyr Thr Phe Gly Gly Gly Thr Lys Leu Glu Ile Lys
            100                 105                 110


<210> SEQ ID NO 28
<211> LENGTH: 111
<212> TYPE: PRT
<213> ORGANISM: Artificial Sequence
<220> FEATURE:
<223> OTHER INFORMATION: Synthetic Construct

<400> SEQUENCE: 28

Asp Ile Val Leu Thr Gln Ser Thr Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Arg Thr Phe Gly Gly Gly Thr Lys Leu Glu Ile Lys
            100                 105                 110
```

<210> SEQ ID NO 29
<211> LENGTH: 111
<212> TYPE: PRT
<213> ORGANISM: Artificial Sequence
<220> FEATURE:
<223> OTHER INFORMATION: Synthetic Construct

<400> SEQUENCE: 29

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Val Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Tyr
                85                  90                  95

Glu Asp Pro Pro Thr Phe Gly Gly Gly Thr Lys Leu Glu Ile Lys
            100                 105                 110
```

<210> SEQ ID NO 30
<211> LENGTH: 111
<212> TYPE: PRT
<213> ORGANISM: Artificial Sequence
<220> FEATURE:
<223> OTHER INFORMATION: Synthetic Construct

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Val Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Ile Ala Thr Tyr Tyr Cys Gln Gln Ser Tyr
                85                  90                  95

Glu Asp Pro Pro Thr Phe Gly Gly Gly Thr Lys Leu Glu Ile Lys
            100                 105                 110
```

<210> SEQ ID NO 31
<211> LENGTH: 111
<212> TYPE: PRT
<213> ORGANISM: Artificial Sequence
<220> FEATURE:
<223> OTHER INFORMATION: Synthetic Construct

<400> SEQUENCE: 31

```
Asp Ile Val Leu Thr Gln Ser Pro Val Phe Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
```

```
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Glu Thr Tyr Tyr Cys Gln Gln Ser Tyr
                85                  90                  95

Glu Asp Pro Pro Thr Phe Gly Gly Gly Thr Lys Leu Glu Ile Glu
            100                 105                 110


<210> SEQ ID NO 32
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa = Tyr or Phe
<220> FEATURE:
<221> NAME/KEY: VARIANT
<222> LOCATION: (3)..(3)
<223> OTHER INFORMATION: Xaa = Thr or Ser
<220> FEATURE:
<221> NAME/KEY: VARIANT
<222> LOCATION: (4)..(4)
<223> OTHER INFORMATION: Xaa = Phe or Leu
<220> FEATURE:
<221> NAME/KEY: VARIANT
<222> LOCATION: (6)..(6)
<223> OTHER INFORMATION: Xaa = Asp or Arg
<220> FEATURE:
<221> NAME/KEY: VARIANT
<222> LOCATION: (8)..(8)
<223> OTHER INFORMATION: Xaa = Ser or Gly
<220> FEATURE:
<221> NAME/KEY: VARIANT
<222> LOCATION: (9)..(9)
<223> OTHER INFORMATION: Xaa = Ile, Met, or Val
<220> FEATURE:
<221> NAME/KEY: VARIANT
<222> LOCATION: (10)..(10)
<223> OTHER INFORMATION: Xaa = His or Asn

<400> SEQUENCE: 32

Gly Xaa Xaa Xaa Thr Xaa Tyr Xaa Xaa Xaa
1               5                   10


<210> SEQ ID NO 33
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa = Ile, Leu, or Met
<220> FEATURE:
<221> NAME/KEY: VARIANT
<222> LOCATION: (4)..(4)
<223> OTHER INFORMATION: Xaa = Val or Leu
<220> FEATURE:
<221> NAME/KEY: VARIANT
<222> LOCATION: (6)..(6)
<223> OTHER INFORMATION: Xaa = Ser or Trp
<220> FEATURE:
<221> NAME/KEY: VARIANT
<222> LOCATION: (7)..(7)
<223> OTHER INFORMATION: Xaa = Ser or Thr
<220> FEATURE:
```

<221> NAME/KEY: VARIANT
<222> LOCATION: (8)..(8)
<223> OTHER INFORMATION: Xaa = Tyr, Phe, or Gly
<220> FEATURE:
<221> NAME/KEY: VARIANT
<222> LOCATION: (9)..(9)
<223> OTHER INFORMATION: Xaa = Tyr or none
<220> FEATURE:
<221> NAME/KEY: VARIANT
<222> LOCATION: (11)..(11)
<223> OTHER INFORMATION: Xaa = Asp or Asn
<220> FEATURE:
<221> NAME/KEY: VARIANT
<222> LOCATION: (12)..(12)
<223> OTHER INFORMATION: Xaa = Ala or Thr
<220> FEATURE:
<221> NAME/KEY: VARIANT
<222> LOCATION: (13)..(13)
<223> OTHER INFORMATION: Xaa = Thr, Ser, Asn, or Asp
<220> FEATURE:
<221> NAME/KEY: VARIANT
<222> LOCATION: (15)..(15)
<223> OTHER INFORMATION: Xaa = Asn or Thr
<220> FEATURE:
<221> NAME/KEY: VARIANT
<222> LOCATION: (16)..(16)
<223> OTHER INFORMATION: Xaa = Gln or Ala
<220> FEATURE:
<221> NAME/KEY: VARIANT
<222> LOCATION: (17)..(17)
<223> OTHER INFORMATION: Xaa = Lys or Ala

<400> SEQUENCE: 33

```
Trp Xaa Gly Xaa Ile Xaa Xaa Xaa Xaa Gly Xaa Xaa Xaa Tyr Xaa Xaa
1               5                   10                  15

Xaa Phe
```

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: Xaa = Leu or Arg
<220> FEATURE:
<221> NAME/KEY: VARIANT
<222> LOCATION: (3)..(3)
<223> OTHER INFORMATION: Xaa = Leu, Tyr, Arg, or Glu
<220> FEATURE:
<221> NAME/KEY: VARIANT
<222> LOCATION: (4)..(4)
<223> OTHER INFORMATION: Xaa = Gly or Asp
<220> FEATURE:
<221> NAME/KEY: VARIANT
<222> LOCATION: (5)..(5)
<223> OTHER INFORMATION: Xaa = Asp, Arg, or none
<220> FEATURE:
<221> NAME/KEY: VARIANT
<222> LOCATION: (6)..(6)
<223> OTHER INFORMATION: Xaa = Ala, Gly, Asn, or Tyr
<220> FEATURE:
<221> NAME/KEY: VARIANT
<222> LOCATION: (7)..(7)
<223> OTHER INFORMATION: Xaa = Tyr or Val
<220> FEATURE:
<221> NAME/KEY: VARIANT
<222> LOCATION: (8)..(8)
<223> OTHER INFORMATION: Xaa = Asn, Asp, or Gly
<220> FEATURE:
<221> NAME/KEY: VARIANT
<222> LOCATION: (9)..(9)
<223> OTHER INFORMATION: Xaa = Tyr, Gln, Ser, or Glu
<220> FEATURE:

<221> NAME/KEY: VARIANT
<222> LOCATION: (10)..(10)
<223> OTHER INFORMATION: Xaa = Phe or Met
<220> FEATURE:
<221> NAME/KEY: VARIANT
<222> LOCATION: (11)..(11)
<223> OTHER INFORMATION: Xaa = Asp or Ala

<400> SEQUENCE: 34

Ala Xaa Xaa Xaa Xaa Xaa Xaa Xaa Xaa Xaa Xaa Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (9)..(9)
<223> OTHER INFORMATION: Xaa = Asn or Ser
<220> FEATURE:
<221> NAME/KEY: VARIANT
<222> LOCATION: (11)..(11)
<223> OTHER INFORMATION: Xaa = Met or Ile

<400> SEQUENCE: 35

Glu Ser Val Asp Ser Tyr Gly Asn Xaa Phe Xaa His
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Leu or Arg
<220> FEATURE:
<221> NAME/KEY: VARIANT
<222> LOCATION: (3)..(3)
<223> OTHER INFORMATION: Xaa = Ile or Val

<400> SEQUENCE: 36

Xaa Leu Xaa Tyr Arg Ala Ser Asn Leu Glu Ser
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = Asn or Tyr
<220> FEATURE:
<221> NAME/KEY: VARIANT
<222> LOCATION: (8)..(8)
<223> OTHER INFORMATION: Xaa = Pro, Arg, or Tyr

<400> SEQUENCE: 37

Gln Gln Ser Xaa Glu Asp Pro Xaa Thr
1               5

<210> SEQ ID NO 38
<211> LENGTH: 11

```
<212> TYPE: PRT
<213> ORGANISM: Artificial Sequence
<220> FEATURE:
<223> OTHER INFORMATION: Synthetic Construct

<400> SEQUENCE: 38

Arg Leu Ile Tyr Arg Ala Ser Asn Leu Glu Ser
1               5                   10


<210> SEQ ID NO 39
<211> LENGTH: 18
<212> TYPE: PRT
<213> ORGANISM: Artificial Sequence
<220> FEATURE:
<223> OTHER INFORMATION: Synthetic Construct

<400> SEQUENCE: 39

Trp Met Gly Val Ile Ser Thr Tyr Tyr Gly Asp Ala Ser Tyr Asn Gln
1               5                   10                  15

Lys Phe


<210> SEQ ID NO 40
<211> LENGTH: 119
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Val Ile Ser Thr Tyr Tyr Gly Asp Ala Ser Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110

Thr Met Val Thr Val Ser Ser
        115


<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Val Ile Ser Thr Tyr Tyr Gly Asp Ala Ser Tyr Asn Gln Lys Phe
```

```
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser
        115


<210> SEQ ID NO 42
<211> LENGTH: 119
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Arg Leu Glu Trp Met
        35                  40                  45

Gly Val Ile Ser Thr Tyr Tyr Gly Asp Ala Ser Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser
        115


<210> SEQ ID NO 43
<211> LENGTH: 119
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Val Ile Ser Thr Tyr Tyr Gly Asp Ala Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110
```

```
Thr Leu Val Thr Val Ser Ser
        115


<210> SEQ ID NO 44
<211> LENGTH: 119
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asp Tyr
            20                  25                  30

Ser Ile Asn Trp Val Arg Gln Met Pro Gly Lys Gly Leu Glu Trp Met
        35                  40                  45

Gly Val Ile Ser Thr Tyr Tyr Gly Asp Ala Ser Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser
        115


<210> SEQ ID NO 45
<211> LENGTH: 119
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Ile Asn Trp Val Lys Gln Ser His Ala Lys Ser Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Tyr Gly Asp Gly Tyr Asn Gln Phe Asp Tyr Trp Gly Gln Gly
            100                 105                 110

Thr Thr Leu Thr Val Ser Ser
        115


<210> SEQ ID NO 46
<211> LENGTH: 111
<212> TYPE: PRT
<213> ORGANISM: Artificial Sequence
<220> FEATURE:
<223> OTHER INFORMATION: Synthetic Construct
```

<400> SEQUENCE: 46

```
Asp Ile Val Met Thr Gln Ser Pro Asp Ser Leu Ala Val Ser Leu Gly
1               5                   10                  15

Glu Arg Ala Thr Ile Asn Cys Arg Val Ser Glu Ser Val Asp Ser Tyr
            20                  25                  30

Gly Asn Asn Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Tyr
                85                  90                  95

Glu Asp Pro Tyr Thr Phe Gly Gln Gly Thr Lys Leu Glu Ile Lys
            100                 105                 110
```

<210> SEQ ID NO 47
<211> LENGTH: 111
<212> TYPE: PRT
<213> ORGANISM: Artificial Sequence
<220> FEATURE:
<223> OTHER INFORMATION: Synthetic Construct

<400> SEQUENCE: 47

```
Asp Val Val Met Thr Gln Ser Pro Leu Ser Leu Pro Val Thr Leu Gly
1               5                   10                  15

Gln Pro Ala Ser Ile Ser Cys Arg Val Ser Glu Ser Val Asp Ser Tyr
            20                  25                  30

Gly Asn Asn Phe Met His Trp Phe Gln Gln Arg Pro Gly Gln Ser Pro
        35                  40                  45

Arg Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Tyr
                85                  90                  95

Glu Asp Pro Tyr Thr Phe Gly Gly Gly Thr Lys Val Glu Ile Lys
            100                 105                 110
```

<210> SEQ ID NO 48
<211> LENGTH: 111
<212> TYPE: PRT
<213> ORGANISM: Artificial Sequence
<220> FEATURE:
<223> OTHER INFORMATION: Synthetic Construct

<400> SEQUENCE: 48

```
Asp Ile Val Met Thr Gln Ser Pro Leu Ser Leu Pro Val Thr Pro Gly
1               5                   10                  15

Glu Pro Ala Ser Ile Ser Cys Arg Val Ser Glu Ser Val Asp Ser Tyr
            20                  25                  30

Gly Asn Asn Phe Met His Trp Tyr Leu Gln Lys Pro Gly Gln Ser Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80
```

```
Arg Val Glu Ala Glu Asp Val Gly Val Tyr Tyr Cys Gln Gln Ser Tyr
                85                  90                  95

Glu Asp Pro Tyr Thr Phe Gly Gly Gly Thr Lys Val Glu Ile Lys
            100                 105                 110


<210> SEQ ID NO 49
<211> LENGTH: 111
<212> TYPE: PRT
<213> ORGANISM: Artificial Sequence
<220> FEATURE:
<223> OTHER INFORMATION: Synthetic Construct

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Val Ser Glu Ser Val Asp Ser Tyr
            20                  25                  30

Gly Asn Asn Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Tyr
                85                  90                  95

Glu Asp Pro Tyr Thr Phe Gly Gly Gly Thr Lys Val Glu Ile Lys
            100                 105                 110


<210> SEQ ID NO 50
<211> LENGTH: 111
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Val Ser Glu Ser Val Asp Ser Tyr
            20                  25                  30

Gly Asn Asn Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Tyr
                85                  90                  95

Glu Asp Pro Tyr Thr Phe Gly Gly Gly Thr Lys Leu Glu Ile Lys
            100                 105                 110


<210> SEQ ID NO 51
<211> LENGTH: 111
<212> TYPE: PRT
<213> ORGANISM: Artificial Sequence
<220> FEATURE:
<223> OTHER INFORMATION: Synthetic Construct

<400> SEQUENCE: 51

Asp Ile Val Leu Thr Gln Ser Pro Ala Ser Leu Ala Val Ser Leu Gly
```

1 5 10 15

Gln Arg Ala Thr Ile Ser Cys Arg Val Ser Glu Ser Val Asp Ser Tyr
20 25 30

Gly Asn Asn Phe Met His Trp Tyr Gln Gln Lys Pro Gly Gln Pro Pro
35 40 45

Lys Leu Leu Ile Tyr Arg Ala Ser Asn Leu Glu Ser Gly Val Pro Ala
50 55 60

Arg Phe Ser Gly Ser Gly Ser Gly Thr Asp Phe Thr Leu Thr Ile Asn
65 70 75 80

Pro Met Glu Ala Asp Asp Val Ala Thr Tyr Tyr Cys Gln Gln Ser Tyr
85 90 95

Glu Asp Pro Tyr Thr Phe Gly Gly Gly Thr Lys Leu Glu Ile Lys
100 105 110

<210> SEQ ID NO 52
<211> LENGTH: 449
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Ser Ile Asn Trp Val Arg Gln Ala Pro Gly Gln Gly Leu Glu Trp Met
35 40 45

Gly Val Ile Ser Thr Tyr Tyr Gly Asp Ala Ser Tyr Asn Gln Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Tyr Gly Asp Gly Tyr Asn Gln Phe Asp Tyr Trp Gly Gln Gly
100 105 110

Thr Met Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp 260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 53
<211> LENGTH: 449
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Ser Ile Asn Trp Val Arg Gln Ala Pro Gly Gln Gly Leu Glu Trp Met
35 40 45

Gly Val Ile Ser Thr Tyr Tyr Gly Asp Ala Ser Tyr Asn Gln Lys Phe
50 55 60

Lys Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Tyr Gly Asp Gly Tyr Asn Gln Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 54
<211> LENGTH: 449
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Arg Leu Glu Trp Met
        35                  40                  45

Gly Val Ile Ser Thr Tyr Tyr Gly Asp Ala Ser Tyr Asn Gln Lys Phe
    50                  55                  60

Lys Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 55
<211> LENGTH: 449
<212> TYPE: PRT
<213> ORGANISM: Artificial Sequence
<220> FEATURE:
<223> OTHER INFORMATION: Synthetic Construct

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Val Ile Ser Thr Tyr Tyr Gly Asp Ala Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 56
<211> LENGTH: 449
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asp Tyr
            20                  25                  30

Ser Ile Asn Trp Val Arg Gln Met Pro Gly Lys Gly Leu Glu Trp Met
        35                  40                  45

Gly Val Ile Ser Thr Tyr Tyr Gly Asp Ala Ser Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Gly Asp Gly Tyr Asn Gln Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 57
<211> LENGTH: 449
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ser Ile Asn Trp Val Lys Gln Ser His Ala Lys Ser Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Tyr Gly Asp Gly Tyr Asn Gln Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 58
<211> LENGTH: 218
<212> TYPE: PRT
<213> ORGANISM: Artificial Sequence
<220> FEATURE:
<223> OTHER INFORMATION: Synthetic Construct

<400> SEQUENCE: 58

Asp Ile Val Met Thr Gln Ser Pro Asp Ser Leu Ala Val Ser Leu Gly
1 5 10 15

Glu Arg Ala Thr Ile Asn Cys Arg Val Ser Glu Ser Val Asp Ser Tyr
20 25 30

Gly Asn Asn Phe Met His Trp Tyr Gln Gln Lys Pro Gly Gln Pro Pro
35 40 45

Lys Leu Leu Ile Tyr Arg Ala Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Tyr
85 90 95

Glu Asp Pro Tyr Thr Phe Gly Gln Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 59
<211> LENGTH: 218
<212> TYPE: PRT
<213> ORGANISM: Artificial Sequence
<220> FEATURE:
<223> OTHER INFORMATION: Synthetic Construct

<400> SEQUENCE: 59

Asp Val Val Met Thr Gln Ser Pro Leu Ser Leu Pro Val Thr Leu Gly
1               5                   10                  15

Gln Pro Ala Ser Ile Ser Cys Arg Val Ser Glu Ser Val Asp Ser Tyr
            20                  25                  30

Gly Asn Asn Phe Met His Trp Phe Gln Gln Arg Pro Gly Gln Ser Pro
        35                  40                  45

Arg Arg Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Tyr
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 60
<211> LENGTH: 218
<212> TYPE: PRT
<213> ORGANISM: Artificial Sequence
<220> FEATURE:
<223> OTHER INFORMATION: Synthetic Construct

<400> SEQUENCE: 60

Asp Ile Val Met Thr Gln Ser Pro Leu Ser Leu Pro Val Thr Pro Gly
```

```
1               5                   10                  15

Glu Pro Ala Ser Ile Ser Cys Arg Val Ser Glu Ser Val Asp Ser Tyr
            20                  25                  30

Gly Asn Asn Phe Met His Trp Tyr Leu Gln Lys Pro Gly Gln Ser Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Tyr
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 61
<211> LENGTH: 218
<212> TYPE: PRT
<213> ORGANISM: Artificial Sequence
<220> FEATURE:
<223> OTHER INFORMATION: Synthetic Construct

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Val Ser Glu Ser Val Asp Ser Tyr
            20                  25                  30

Gly Asn Asn Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Tyr
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
```

145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 62
<211> LENGTH: 218
<212> TYPE: PRT
<213> ORGANISM: Artificial Sequence
<220> FEATURE:
<223> OTHER INFORMATION: Synthetic Construct

<400> SEQUENCE: 62

Asp Ile Gln Met Thr Gln Ser Pro Ser Ser Leu Ser Ala Ser Val Gly
1 5 10 15

Asp Arg Val Thr Ile Thr Cys Arg Val Ser Glu Ser Val Asp Ser Tyr
20 25 30

Gly Asn Asn Phe Met His Trp Tyr Gln Gln Lys Pro Gly Lys Ala Pro
35 40 45

Lys Leu Leu Ile Tyr Arg Ala Ser Asn Leu Glu Ser Gly Val Pro Ser
50 55 60

Arg Phe Ser Gly Ser Gly Ser Gly Thr Asp Phe Thr Phe Thr Ile Ser
65 70 75 80

Ser Leu Gln Pro Glu Asp Ile Ala Thr Tyr Tyr Cys Gln Gln Ser Tyr
85 90 95

Glu Asp Pro Tyr Thr Phe Gly Gly Gly Thr Lys Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 63
<211> LENGTH: 218
<212> TYPE: PRT
<213> ORGANISM: Artificial Sequence
<220> FEATURE:
<223> OTHER INFORMATION: Synthetic Construct

<400> SEQUENCE: 63

Asp Ile Val Leu Thr Gln Ser Pro Ala Ser Leu Ala Val Ser Leu Gly
1 5 10 15

```
Gln Arg Ala Thr Ile Ser Cys Arg Val Ser Glu Ser Val Asp Ser Tyr
            20                  25                  30

Gly Asn Asn Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Met Glu Ala Asp Asp Val Ala Thr Tyr Tyr Cys Gln Gln Ser Tyr
                85                  90                  95

Glu Asp Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 64
<211> LENGTH: 330
<212> TYPE: PRT
<213> ORGANISM: Artificial Sequence
<220> FEATURE:
<223> OTHER INFORMATION: Synthetic Construct

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 65
<211> LENGTH: 329
<212> TYPE: PRT
<213> ORGANISM: Artificial Sequence
<220> FEATURE:
<223> OTHER INFORMATION: Synthetic Construct

<400> SEQUENCE: 65

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 66
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 66

```
caggtgcagc tggtgcagtc tggagcagag gtgaagaagc caggagcaag cgtgaaggtg     60

tcctgcaagg cctctggcta caccttcaca gactatagca tcaactgggt gaggcaggca    120

cctggacagg gactggagtg gatgggcgtg atcagcacat actatggcga cgcctcctac    180

aatcagaagt ttaagggccg cgtgaccatg accacagata cctctacaag caccgcctat    240

atggagctgc ggtccctgag atctgacgat acagccgtgt actattgtgc ccggtacggc    300

gacggctata accagttcga ttactggggc cagggcacaa tggtgaccgt gagctccgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260
```

```
caggggaacg tcttctcatg ctccgtgatg catgaggctc tgcacaacca ctacacgcag   1320

aagagcctct ccctgtctcc gggtaaatga                                    1350
```

<210> SEQ ID NO 67
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 67

```
caggtgcagc tggtgcagtc tggagcagag gtgaagaagc caggagcaag cgtgaaggtg     60

tcctgcaagg cctctggcta caccttcaca gactatagca tcaactgggt gcggcaggca    120

cctggacagg gactggagtg gatgggcgtg atcagcacat actatggcga cgcctcctac    180

aatcagaagt ttaagggccg ggtgaccatg acaagagata cctccacatc taccgtgtat    240

atggagctga gctccctgag gtccgaggat accgccgtgt actattgtgc ccgctacggc    300

gacggctata accagttcga ttactggggc cagggcacac tggtgaccgt gtctagcgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaatga                                    1350
```

<210> SEQ ID NO 68
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 68

```
caggtgcagc tggtgcagtc tggagcagag gtgaagaagc caggagcaag cgtgaaggtg     60

tcctgcaagg cctctggcta caccttcaca gactatagca tcaactgggt gaggcaggca    120

cctggacagc gcctggagtg gatgggcgtg atcagcacct actatggcga cgcctcctac    180

aatcagaagt ttaagggccg ggtgaccatc acaagagata cctccgcctc tacagcctat    240

atggagctga gctccctgcg gtccgaggat acagccgtgt actattgtgc cagatacggc    300
```

gacggctata accagttcga ttactggggc cagggcaccc tggtgacagt gtctagcgct 360
agcaccaagg gcccatcggt cttcccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagaaagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaatga 1350

<210> SEQ ID NO 69
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 69
caggtgcagc tggtgcagag cggagcagag gtgaagaagc caggaagctc cgtgaaggtg 60
tcttgcaagg ccagcggcta caccttcaca gactattcca tcaactgggt gaggcaggca 120
cctggacagg gactggagtg gatgggcgtg atctccacct actatggcga cgcctcttac 180
aatcagaagt ttaagggccg ggtgaccatc acagccgatg agagcacctc cacagcctat 240
atggagctgt ctagcctgcg gtctgaggat acagccgtgt actattgtgc cagatacggc 300
gacggctata accagttcga ttactggggc cagggcaccc tggtgacagt gtcctctgct 360
agcaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagaaagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaatga 1350

<210> SEQ ID NO 70
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 70
gaggtgcagc tggtgcagtc cggagcagag gtgaagaagc caggcgagag cctgaagatc 60
tcctgcaagg gctctggcta caccttcaca gactattcta tcaactgggt gcggcagatg 120
cctggcaagg gactggagtg gatgggcgtg atcagcacct actatggcga cgcctcctac 180
aatcagaagt ttaagggcca ggtgaccatc tctgccgata agtccatctc tacagcctat 240
ctgcagtgga gctccctgaa ggccagcgat acagccatgt actattgtgc cagatacggc 300
gacggctata accagttcga ttactggggc cagggcaccc tggtgacagt gtctagcgct 360
agcaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagaaagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaatga 1350

<210> SEQ ID NO 71
<211> LENGTH: 657
<212> TYPE: DNA
<213> ORGANISM: Artificial Sequence
<220> FEATURE:
<223> OTHER INFORMATION: Synthetic Construct

<400> SEQUENCE: 71
gacatcgtga tgacccagtc ccctgattct ctggccgtgt ctctgggaga gagggcaaca 60
atcaactgca gagtgtctga gagcgtggac agctacggca acaatttcat gcactggtat 120
cagcagaagc caggccagcc ccctaagctg ctgatctaca gggcaagcaa tctggagtcc 180
ggagtgccag accggttctc cggatctgga agcggaaccg acttcaccct gacaatcagc 240
tccctgcagg cagaggacgt ggccgtgtac tattgtcagc agtcctacga ggatccctat 300
acctttggcc agggcacaaa gctggagatc aagcgaacgg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 72
<211> LENGTH: 657
<212> TYPE: DNA
<213> ORGANISM: Artificial Sequence
<220> FEATURE:
<223> OTHER INFORMATION: Synthetic Construct

<400> SEQUENCE: 72
gacgtggtca tgacccagtc cccctgtct ctgcctgtga cactgggaca gccagcaagc 60
atctcctgca gggtgtctga gagcgtggat tcctacggca acaatttcat gcactggttt 120
cagcagaggc caggccagtc tccccggaga ctgatctata gggcaagcaa cctggagtcc 180
ggagtgcctg accggttctc cggatctgga agcggaaccg acttcaccct gaagatctct 240
agggtggagg cagaggacgt gggcgtgtac tattgtcagc agagctacga ggatccatat 300
accttcggcg gcggcacaaa ggtggagatc aagcgaacgg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttag 657

<210> SEQ ID NO 73
<211> LENGTH: 657
<212> TYPE: DNA
<213> ORGANISM: Artificial Sequence
<220> FEATURE:
<223> OTHER INFORMATION: Synthetic Construct

<400> SEQUENCE: 73
gacatcgtga tgacccagtc ccctctgtct ctgccagtga cacctggaga gccagcaagc 60
atctcctgca gggtgtctga gagcgtggat tcctacggca acaatttcat gcactggtat 120
ctgcagaagc ccggccagtc tcctcagctg ctgatctaca gggcaagcaa cctggagtcc 180
ggagtgccag acagattctc cggatctgga agcggaaccg acttcaccct gaagatctct 240
agggtggagg cagaggacgt gggcgtgtac tattgtcagc agagctacga ggatccctat 300
acctttggcg gcggcacaaa ggtggagatc aagcgaacgg tggctgcacc atctgtcttc 360
atcttcccgc catctgatga gcagttgaaa tctggaactg cctctgttgt gtgcctgctg 420

```
aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgttag       657
```

<210> SEQ ID NO 74
<211> LENGTH: 657
<212> TYPE: DNA
<213> ORGANISM: Artificial Sequence
<220> FEATURE:
<223> OTHER INFORMATION: Synthetic Construct

<400> SEQUENCE: 74

```
gagatcgtgc tgacccagtc cccagccaca ctgtctctga gcccaggaga gagggccacc     60

ctgtcttgcc gcgtgtccga gtctgtggat agctacggca acaatttcat gcactggtat    120

cagcagaagc caggacaggc acctaggctg ctgatctaca gagcaagcaa cctggagtcc    180

ggaatcccag cacggttcag cggatccggc tctggcacag actttaccct gacaatcagc    240

tccctggagc ctgaggattt cgccgtgtac tattgtcagc agtcttacga ggacccatat    300

acctttggcg gcggcacaaa ggtggagatc aagcgaacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgttag       657
```

<210> SEQ ID NO 75
<211> LENGTH: 657
<212> TYPE: DNA
<213> ORGANISM: Artificial Sequence
<220> FEATURE:
<223> OTHER INFORMATION: Synthetic Construct

<400> SEQUENCE: 75

```
gatatccaga tgacccagtc tcctagctcc ctgtccgcct ctgtgggcga tagggtgacc     60

atcacatgca gagtgagcga gtccgtggac tcctacggca acaatttcat gcactggtat    120

cagcagaagc ccggcaaggc ccctaagctg ctgatctaca gggcctctaa cctggagagc    180

ggagtgccat cccggttttc tggaagcgga tccggaaccg acttcacctt tacaatctct    240

agcctgcagc cagaggatat cgccacatac tattgtcagc agagctacga ggacccctat    300

accttcggcg gcggcacaaa gctggagatc aagcgaacgg tggctgcacc atctgtcttc    360

atcttcccgc catctgatga gcagttgaaa tctggaactg cctctgttgt gtgcctgctg    420

aataacttct atcccagaga ggccaaagta cagtggaagg tggataacgc cctccaatcg    480

ggtaactccc aggagagtgt cacagagcag gacagcaagg acagcaccta cagcctcagc    540

agcaccctga cgctgagcaa agcagactac gagaaacaca aagtctacgc ctgcgaagtc    600

acccatcagg gcctgagctc gcccgtcaca aagagcttca acaggggaga gtgttag       657
```

<210> SEQ ID NO 76
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 76
atgggctgga gctggatcct gctgttcctc ctgagcgtga cagcaggagt gcacagccag 60
gtgcagctgg tgcagtctgg agcagaggtg aagaagccag gagcaagcgt gaaggtgtcc 120
tgcaaggcct ctggctacac cttcacagac tatagcatca actgggtgag gcaggcacct 180
ggacagggac tggagtggat gggcgtgatc agcacatact atggcgacgc ctcctacaat 240
cagaagttta agggccgcgt gaccatgacc acagatacct ctacaagcac cgcctatatg 300
gagctgcggt ccctgagatc tgacgataca gccgtgtact attgtgcccg gtacggcgac 360
ggctataacc agttcgatta ctggggccag ggcacaatgg tgaccgtgag ctccgctagc 420
accaagggcc catcggtctt ccccctggca ccctcctcca agagcacctc tgggggcaca 480
gcggccctgg gctgcctggt caaggactac ttccccgaac cggtgacggt gtcgtggaac 540
tcaggcgccc tgaccagcgg cgtgcacacc ttcccggctg tcctacagtc ctcaggactc 600
tactccctca gcagcgtggt gaccgtgccc tccagcagct tgggcaccca gacctacatc 660
tgcaacgtga atcacaagcc cagcaacacc aaggtggaca agaaagttga gcccaaatct 720
tgtgacaaaa ctcacacatg cccaccgtgc ccagcacctg aactcctggg gggaccgtca 780
gtcttcctct tccccccaaa acccaaggac accctcatga tctcccggac ccctgaggtc 840
acatgcgtgg tggtggacgt gagccacgaa gaccctgagg tcaagttcaa ctggtacgtg 900
gacggcgtgg aggtgcataa tgccaagaca aagccgcggg aggagcagta caacagcacg 960
taccgtgtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc cccgagaacc acaggtgtac accctgcccc catcccggga tgagctgacc 1140
aagaaccagg tcagcctgac ctgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaatga 1407

<210> SEQ ID NO 77
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 77
atgggctgga gctggatcct gctgttcctc ctgagcgtga cagcaggagt gcacagccag 60
gtgcagctgg tgcagtctgg agcagaggtg aagaagccag gagcaagcgt gaaggtgtcc 120
tgcaaggcct ctggctacac cttcacagac tatagcatca actgggtgcg gcaggcacct 180
ggacagggac tggagtggat gggcgtgatc agcacatact atggcgacgc ctcctacaat 240
cagaagttta agggccgggt gaccatgaca agagatacct ccacatctac cgtgtatatg 300
gagctgagct ccctgaggtc cgaggatacc gccgtgtact attgtgcccg ctacggcgac 360
ggctataacc agttcgatta ctggggccag ggcacactgg tgaccgtgtc tagcgctagc 420
accaagggcc catcggtctt ccccctggca ccctcctcca agagcacctc tgggggcaca 480
gcggccctgg gctgcctggt caaggactac ttccccgaac cggtgacggt gtcgtggaac 540

```
tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agaaagttga gcccaaatct    720

tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga tgagctgacc   1140

aagaaccagg tcagcctgac ctgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaatga                                       1407
```

```
<210> SEQ ID NO 78
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 78
```

```
atgggctgga gctggatcct gctgttcctc ctgagcgtga cagcaggagt gcacagccag     60

gtgcagctgg tgcagtctgg agcagaggtg aagaagccag gagcaagcgt gaaggtgtcc    120

tgcaaggcct ctggctacac cttcacagac tatagcatca actgggtgag gcaggcacct    180

ggacagcgcc tggagtggat gggcgtgatc agcacctact atggcgacgc ctcctacaat    240

cagaagttta agggccgggt gaccatcaca agagatacct ccgcctctac agcctatatg    300

gagctgagct ccctgcggtc cgaggataca gccgtgtact attgtgccag atacggcgac    360

ggctataacc agttcgatta ctggggccag ggcaccctgg tgacagtgtc tagcgctagc    420

accaagggcc catcggtctt ccccctggca ccctcctcca agagcacctc tgggggcaca    480

gcggccctgg gctgcctggt caaggactac ttccccgaac cggtgacggt gtcgtggaac    540

tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agaaagttga gcccaaatct    720

tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga tgagctgacc   1140

aagaaccagg tcagcctgac ctgcctggtc aaaggcttct atcccagcga catcgccgtg   1200
```

gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaatga 1407

<210> SEQ ID NO 79
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 79
atgggctgga gctggatcct gctgttcctc ctgagcgtga cagcaggagt gcacagccag 60
gtgcagctgg tgcagagcgg agcagaggtg aagaagccag gaagctccgt gaaggtgtct 120
tgcaaggcca gcggctacac cttcacagac tattccatca actgggtgag gcaggcacct 180
ggacagggac tggagtggat gggcgtgatc tccacctact atggcgacgc ctcttacaat 240
cagaagttta agggccgggt gaccatcaca gccgatgaga gcacctccac agcctatatg 300
gagctgtcta gcctgcggtc tgaggataca gccgtgtact attgtgccag atacggcgac 360
ggctataacc agttcgatta ctggggccag ggcaccctgg tgacagtgtc ctctgctagc 420
accaagggcc catcggtctt ccccctggca ccctcctcca agagcacctc tgggggcaca 480
gcggccctgg gctgcctggt caaggactac ttccccgaac cggtgacggt gtcgtggaac 540
tcaggcgccc tgaccagcgg cgtgcacacc ttcccggctg tcctacagtc ctcaggactc 600
tactccctca gcagcgtggt gaccgtgccc tccagcagct tgggcaccca gacctacatc 660
tgcaacgtga atcacaagcc cagcaacacc aaggtggaca agaaagttga gcccaaatct 720
tgtgacaaaa ctcacacatg cccaccgtgc ccagcacctg aactcctggg gggaccgtca 780
gtcttcctct tccccccaaa acccaaggac accctcatga tctcccggac ccctgaggtc 840
acatgcgtgg tggtggacgt gagccacgaa gaccctgagg tcaagttcaa ctggtacgtg 900
gacggcgtgg aggtgcataa tgccaagaca aagccgcggg aggagcagta caacagcacg 960
taccgtgtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc cccgagaacc acaggtgtac accctgcccc catcccggga tgagctgacc 1140
aagaaccagg tcagcctgac ctgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaatga 1407

<210> SEQ ID NO 80
<211> LENGTH: 1407
<212> TYPE: DNA
<213> ORGANISM: Artificial Sequence
<220> FEATURE:
<223> OTHER INFORMATION: Synthetic Construct

<400> SEQUENCE: 80
atgggctgga gctggatcct gctgttcctc ctgagcgtga cagcaggagt gcacagcgag 60

```
gtgcagctgg tgcagtccgg agcagaggtg aagaagccag gcgagagcct gaagatctcc    120
tgcaagggct ctggctacac cttcacagac tattctatca actgggtgcg gcagatgcct    180
ggcaagggac tggagtggat gggcgtgatc agcacctact atggcgacgc ctcctacaat    240
cagaagttta agggccaggt gaccatctct gccgataagt ccatctctac agcctatctg    300
cagtggagct ccctgaaggc cagcgataca gccatgtact attgtgccag atacggcgac    360
ggctataacc agttcgatta ctggggccag ggcaccctgg tgacagtgtc tagcgctagc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct tgggcaccca gacctacatc    660
tgcaacgtga atcacaagcc cagcaacacc aaggtggaca agaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407
```

<210> SEQ ID NO 81
<211> LENGTH: 714
<212> TYPE: DNA
<213> ORGANISM: Artificial Sequence
<220> FEATURE:
<223> OTHER INFORMATION: Synthetic Construct

<400> SEQUENCE: 81

```
atgggctgga gctggatcct gctgttcctc ctgagcgtga cagcaggagt gcacagcgac     60
atcgtgatga cccagtcccc tgattctctg gccgtgtctc tgggagagag ggcaacaatc    120
aactgcagag tgtctgagag cgtggacagc tacggcaaca atttcatgca ctggtatcag    180
cagaagccag gccagccccc taagctgctg atctacaggg caagcaatct ggagtccgga    240
gtgccagacc ggttctccgg atctggaagc ggaaccgact tcaccctgac aatcagctcc    300
ctgcaggcag aggacgtggc cgtgtactat tgtcagcagt cctacgagga tccctatacc    360
tttggccagg gcacaaagct ggagatcaag cgaacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714
```

<210> SEQ ID NO 82
<211> LENGTH: 714
<212> TYPE: DNA
<213> ORGANISM: Artificial Sequence
<220> FEATURE:
<223> OTHER INFORMATION: Synthetic Construct

<400> SEQUENCE: 82
atgggctgga gctggatcct gctgttcctc ctgagcgtga cagcaggagt gcacagcgac 60
gtggtcatga cccagtcccc cctgtctctg cctgtgacac tgggacagcc agcaagcatc 120
tcctgcaggg tgtctgagag cgtggattcc tacggcaaca atttcatgca ctggtttcag 180
cagaggccag gccagtctcc ccggagactg atctataggg caagcaacct ggagtccgga 240
gtgcctgacc ggttctccgg atctggaagc ggaaccgact tcaccctgaa gatctctagg 300
gtggaggcag aggacgtggg cgtgtactat tgtcagcaga gctacgagga tccatatacc 360
ttcggcggcg gcacaaaggt ggagatcaag cgaacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 83
<211> LENGTH: 714
<212> TYPE: DNA
<213> ORGANISM: Artificial Sequence
<220> FEATURE:
<223> OTHER INFORMATION: Synthetic Construct

<400> SEQUENCE: 83
atgggctgga gctggatcct gctgttcctc ctgagcgtga cagcaggagt gcacagcgac 60
atcgtgatga cccagtcccc tctgtctctg ccagtgacac ctggagagcc agcaagcatc 120
tcctgcaggg tgtctgagag cgtggattcc tacggcaaca atttcatgca ctggtatctg 180
cagaagcccg gccagtctcc tcagctgctg atctacaggg caagcaacct ggagtccgga 240
gtgccagaca gattctccgg atctggaagc ggaaccgact tcaccctgaa gatctctagg 300
gtggaggcag aggacgtggg cgtgtactat tgtcagcaga gctacgagga tccctatacc 360
tttggcggcg gcacaaaggt ggagatcaag cgaacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 84
<211> LENGTH: 714
<212> TYPE: DNA
<213> ORGANISM: Artificial Sequence
<220> FEATURE:
<223> OTHER INFORMATION: Synthetic Construct

<400> SEQUENCE: 84

```
atgggctgga gctggatcct gctgttcctc ctgagcgtga cagcaggagt gcacagcgag     60

atcgtgctga cccagtcccc agccacactg tctctgagcc caggagagag ggccaccctg    120

tcttgccgcg tgtccgagtc tgtggatagc tacggcaaca atttcatgca ctggtatcag    180

cagaagccag gacaggcacc taggctgctg atctacagag caagcaacct ggagtccgga    240

atcccagcac ggttcagcgg atccggctct ggcacagact ttaccctgac aatcagctcc    300

ctggagcctg aggatttcgc cgtgtactat tgtcagcagt cttacgagga cccatatacc    360

tttggcggcg gcacaaaggt ggagatcaag cgaacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg ttag          714
```

```
<210> SEQ ID NO 85
<211> LENGTH: 714
<212> TYPE: DNA
<213> ORGANISM: Artificial Sequence
<220> FEATURE:
<223> OTHER INFORMATION: Synthetic Construct

<400> SEQUENCE: 85

atgggctgga gctggatcct gctgttcctc ctgagcgtga cagcaggagt gcacagcgat     60

atccagatga cccagtctcc tagctccctg tccgcctctg tgggcgatag ggtgaccatc    120

acatgcagag tgagcgagtc cgtggactcc tacggcaaca atttcatgca ctggtatcag    180

cagaagcccg gcaaggcccc taagctgctg atctacaggg cctctaacct ggagagcgga    240

gtgccatccc ggtttctgg aagcggatcc ggaaccgact tcacctttac aatctctagc    300

ctgcagccag aggatatcgc cacatactat tgtcagcaga gctacgagga cccctatacc    360

ttcggcggcg gcacaaagct ggagatcaag cgaacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg ttag          714
```

```
<210> SEQ ID NO 86
<211> LENGTH: 323
<212> TYPE: PRT
<213> ORGANISM: Artificial Sequence
<220> FEATURE:
<223> OTHER INFORMATION: Synthetic Construct

<400> SEQUENCE: 86

Met Ala Arg Gly Pro Gly Leu Ala Pro Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60
```

```
Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu


<210> SEQ ID NO 87
<211> LENGTH: 20
<212> TYPE: PRT
<213> ORGANISM: Artificial Sequence
<220> FEATURE:
<223> OTHER INFORMATION: Synthetic Construct

<400> SEQUENCE: 87

Trp Ile Gly Val Ile Ser Thr Tyr Tyr Gly Asp Ala Ser Tyr Asn Gln
1               5                   10                  15

Lys Phe Lys Gly
            20


<210> SEQ ID NO 88
<211> LENGTH: 19
<212> TYPE: PRT
<213> ORGANISM: Artificial Sequence
<220> FEATURE:
<223> OTHER INFORMATION: Synthetic Construct

<400> SEQUENCE: 88

Trp Leu Gly Val Ile Trp Ser Gly Gly Asn Thr Asp Tyr Asn Ala Ala
1               5                   10                  15
```

Phe Ile Ser

<210> SEQ ID NO 89
<211> LENGTH: 20
<212> TYPE: PRT
<213> ORGANISM: Artificial Sequence
<220> FEATURE:
<223> OTHER INFORMATION: Synthetic Construct

<400> SEQUENCE: 89

Trp Ile Gly Val Ile Ser Ser Tyr Tyr Gly Asp Ala Thr Tyr Asn Gln
1               5                   10                  15

Lys Phe Lys Gly
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic Construct

<400> SEQUENCE: 90

Trp Ile Gly Leu Ile Ser Thr Tyr Tyr Gly Asp Ala Thr Tyr Thr Gln
1               5                   10                  15

Lys Phe Lys Gly
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic Construct

<400> SEQUENCE: 91

Trp Ile Gly Val Ile Ser Thr Phe Tyr Gly Asp Ala Asn Tyr Asn Gln
1               5                   10                  15

Lys Phe Lys Gly
            20

<210> SEQ ID NO 92
<211> LENGTH: 15
<212> TYPE: PRT
<213> ORGANISM: Artificial Sequence
<220> FEATURE:
<223> OTHER INFORMATION: Synthetic Construct

<400> SEQUENCE: 92

Arg Val Ser Glu Ser Val Asp Ser Tyr Gly Asn Asn Phe Met His
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Construct

<400> SEQUENCE: 93

Arg Ala Ser Glu Ser Val Asp Ser Tyr Gly Asn Ser Phe Ile His
1               5                   10                  15

<210> SEQ ID NO 94

<211> LENGTH: 15
<212> TYPE: PRT
<213> ORGANISM: Artificial Sequence
<220> FEATURE:
<223> OTHER INFORMATION: Synthetic Construct

<400> SEQUENCE: 94

Arg Ala Ser Glu Ser Val Asp Ser Tyr Gly Asn Ser Phe Met His
1 5 10 15

<210> SEQ ID NO 95
<211> LENGTH: 20
<212> TYPE: PRT
<213> ORGANISM: Artificial Sequence
<220> FEATURE:
<223> OTHER INFORMATION: Synthetic Construct

<400> SEQUENCE: 95

Trp Met Gly Val Ile Ser Thr Tyr Tyr Gly Asp Ala Ser Tyr Asn Gln
1 5 10 15

Lys Phe Lys Gly
20

<210> SEQ ID NO 96
<211> LENGTH: 17
<212> TYPE: PRT
<213> ORGANISM: Artificial Sequence
<220> FEATURE:
<223> OTHER INFORMATION: Synthetic Construct

<400> SEQUENCE: 96

Val Ile Ser Thr Tyr Tyr Gly Asp Ala Ser Tyr Asn Gln Lys Phe Lys
1 5 10 15

Gly

<210> SEQ ID NO 97
<211> LENGTH: 16
<212> TYPE: PRT
<213> ORGANISM: Artificial Sequence
<220> FEATURE:
<223> OTHER INFORMATION: Synthetic Construct

<400> SEQUENCE: 97

Val Ile Trp Ser Gly Gly Asn Thr Asp Tyr Asn Ala Ala Phe Ile Ser
1 5 10 15

<210> SEQ ID NO 98
<211> LENGTH: 17
<212> TYPE: PRT
<213> ORGANISM: Artificial Sequence
<220> FEATURE:
<223> OTHER INFORMATION: Synthetic Construct

<400> SEQUENCE: 98

Val Ile Ser Ser Tyr Tyr Gly Asp Ala Thr Tyr Asn Gln Lys Phe Lys
1 5 10 15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Leu Ile Ser Thr Tyr Tyr Gly Asp Ala Thr Tyr Thr Gln Lys Phe Lys
1 5 10 15

Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic Construct

<400> SEQUENCE: 100

Val Ile Ser Thr Phe Tyr Gly Asp Ala Asn Tyr Asn Gln Lys Phe Lys
1 5 10 15

Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic Construct

<400> SEQUENCE: 101

Val Ile Ser Thr Tyr Tyr Gly Asp Ala Ser Tyr Asn Gln Lys Phe Lys
1 5 10 15

Gly

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 102

Arg Ala Ser Asn Leu Glu Ser
1 5

<210> SEQ ID NO 103
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Trp or none
<220> FEATURE:
<221> NAME/KEY: VARIANT
<222> LOCATION: (2)..(2)
<223> OTHER INFORMATION: Xaa = Leu, Met, Ile, or none
<220> FEATURE:
<221> NAME/KEY: VARIANT
<222> LOCATION: (3)..(3)
<223> OTHER INFORMATION: Xaa = Gly or none
<220> FEATURE:
<221> NAME/KEY: VARIANT
<222> LOCATION: (4)..(4)
<223> OTHER INFORMATION: Xaa = Val or Leu
<220> FEATURE:
<221> NAME/KEY: VARIANT
<222> LOCATION: (6)..(6)
<223> OTHER INFORMATION: Xaa = Ser or Trp
<220> FEATURE:
<221> NAME/KEY: VARIANT
<222> LOCATION: (7)..(7)

<223> OTHER INFORMATION: Xaa = Ser or Thr
<220> FEATURE:
<221> NAME/KEY: VARIANT
<222> LOCATION: (8)..(8)
<223> OTHER INFORMATION: Xaa = Tyr, Phe, or Gly
<220> FEATURE:
<221> NAME/KEY: VARIANT
<222> LOCATION: (9)..(9)
<223> OTHER INFORMATION: Xaa = Tyr or none
<220> FEATURE:
<221> NAME/KEY: VARIANT
<222> LOCATION: (11)..(11)
<223> OTHER INFORMATION: Xaa = Asp or Asn
<220> FEATURE:
<221> NAME/KEY: VARIANT
<222> LOCATION: (12)..(12)
<223> OTHER INFORMATION: Xaa = Ala or Thr
<220> FEATURE:
<221> NAME/KEY: VARIANT
<222> LOCATION: (13)..(13)
<223> OTHER INFORMATION: Xaa = Thr, Ser, Asn, or Asp
<220> FEATURE:
<221> NAME/KEY: VARIANT
<222> LOCATION: (15)..(15)
<223> OTHER INFORMATION: Xaa = Asn or Thr
<220> FEATURE:
<221> NAME/KEY: VARIANT
<222> LOCATION: (16)..(16)
<223> OTHER INFORMATION: Xaa = Gln or Ala
<220> FEATURE:
<221> NAME/KEY: VARIANT
<222> LOCATION: (17)..(17)
<223> OTHER INFORMATION: Xaa = Lys or Ala
<220> FEATURE:
<221> NAME/KEY: VARIANT
<222> LOCATION: (19)..(19)
<223> OTHER INFORMATION: Xaa = Lys, Ile, or none
<220> FEATURE:
<221> NAME/KEY: VARIANT
<222> LOCATION: (20)..(20)
<223> OTHER INFORMATION: Xaa = Gly, Ser, or none

<400> SEQUENCE: 103

```
Xaa Xaa Xaa Xaa Ile Xaa Xaa Xaa Xaa Gly Xaa Xaa Xaa Tyr Xaa Xaa
1               5                   10                  15

Xaa Phe Xaa Xaa
            20
```

<210> SEQ ID NO 104
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Arg or none
<220> FEATURE:
<221> NAME/KEY: VARIANT
<222> LOCATION: (2)..(2)
<223> OTHER INFORMATION: Xaa = Ala, Val, or none
<220> FEATURE:
<221> NAME/KEY: VARIANT
<222> LOCATION: (3)..(3)
<223> OTHER INFORMATION: Xaa = Ser or none
<220> FEATURE:
<221> NAME/KEY: VARIANT
<222> LOCATION: (12)..(12)
<223> OTHER INFORMATION: Xaa = Asn or Ser
<220> FEATURE:
<221> NAME/KEY: VARIANT
<222> LOCATION: (14)..(14)
<223> OTHER INFORMATION: Xaa = Met or Ile

<400> SEQUENCE: 104

-continued

```
Xaa Xaa Xaa Glu Ser Val Asp Ser Tyr Gly Asn Xaa Phe Xaa His
1               5                   10                  15


<210> SEQ ID NO 105
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Leu, Arg, or none
<220> FEATURE:
<221> NAME/KEY: VARIANT
<222> LOCATION: (2)..(2)
<223> OTHER INFORMATION: Xaa = Leu or none
<220> FEATURE:
<221> NAME/KEY: VARIANT
<222> LOCATION: (3)..(3)
<223> OTHER INFORMATION: Xaa = Ile, Val, or none
<220> FEATURE:
<221> NAME/KEY: VARIANT
<222> LOCATION: (4)..(4)
<223> OTHER INFORMATION: Xaa = Tyr or none

<400> SEQUENCE: 105

Xaa Xaa Xaa Xaa Arg Ala Ser Asn Leu Glu Ser
1               5                   10
```

ANTI-TROPHOBLAST CELL SURFACE ANTIGEN 2 (TROP2) ANTIBODIES AND ANTIBODY DRUG CONJUGATES COMPRISING SAME

CROSS REFERENCE TO RELATED APPLICATIONS

The present application is a National Stage of International Application No. PCT/US2020/023421, filed on Mar. 18, 2020, which claims priority of the American Patent Application No. U.S. 62/820,831 filed on Mar. 19, 2019, the contents of which are incorporated herein by reference in their entireties.

SUBMISSION OF SEQUENCE LISTING ON ASCII TEXT FILE

The Sequence Listing is submitted concurrently with the specification as an ASCII formatted text file via EFS-Web, with a file name of "P21416862US-2-SEQ", a creation date of Sep. 6, 2021, and a size of 110 KB. The Sequence Listing filed via EFS-Web is part of the specification and is incorporated in its entirety by reference herein.

BACKGROUND OF THE INVENTION

Trophoblast cell surface antigen 2 (TROP2) is a 36 kDa transmembrane glycoprotein expressed primarily in epithelial cells and was first identified in human trophoblasts. TROP2 has several binding partners, including Claudin 1, Claudin 7, Cyclin D1, protein kinase C (PKC), PIP2, and insulin-like growth factor 1 (IGF-1) (Cubas et al. (2009) *Biochimica et Biophysica Acta.* 1796: 309-314; Vidmar et al. (2013) *Protein Exp and Pur.* 91: 69-76; and Huang et al. (2005) *Clin Cancer Res.* 11: 4357-4364). By binding to these targets, Trop2 affects tight junctions at the epithelial barrier (Shvartsur et al. (2015) *Genes Cancer.* 6: 84-105) increases tumor proliferation (Guerra et al. (2008) *Cancer Res.* 68: 8113-8121) and Raf and NF-kappa activation (Cubas et al. (2009) *Biochimica et Biophysica Acta.* 1796: 309-314; Shvartsur et al. (2015) *Genes Cancer.* 6: 84-105) and suppresses IGF-1R signaling (Lin et al. (2012) *EMBO Mol Med.* 4: 472-485).

Somatic adult tissues show little or no Trop2 expression (Cubas et al. (2009) *Biochimica et Biophysica Acta.* 1796: 309-314; Zhang et al. (1997) *Science.* 276: 1268-1272). By contrast, TROP2 is overexpressed in various cancers (Tsujikawa et al. (1999) *Nat Genet.* 21: 420-423; Fong et al. (2008) *Mod path.* 21:186-191; Muhlmann et al. (2009) *J Clin Path.* 62:152-158; and Wu et al. (2013) *Head & Neck.* 35:1373-1378), and its expression correlates with aggressive tumor behavior (Wang (2011) *Mol Cancer Res.* 9: 1686-1695), cancer progression, and poor prognosis (Wang et al. (2008) *Mol Cancer Ther* 7: 280-285). Accordingly, there is a need for antibody therapy directed against TROP2-expressing cancer cells. The present invention meets this and other needs.

The disclosures of all patent and scientific literature cited herein are expressly incorporated in their entirety by reference.

BRIEF SUMMARY OF THE INVENTION

Provided herein is an anti-Trophoblast cell surface antigen 2 (TROP2) antibody or antigen-binding fragment thereof that specifically binds TROP2. In some embodiments according to (or as applied to) any of the embodiments herein, the antibody specifically binds TROP2 expressed on the surface of a cell.

In some embodiments according to (or as applied to) any of the embodiments herein, the cell is a cancer cell, and wherein the cancer cell is a breast cancer cell, a cervical cancer cell, a colon cancer cell, a colorectal cancer cell, an endometrioid endometrial cancer (EEC) cell, an esophageal cancer cell, a gastric cancer cell, a glioma cell, a lung cancer cell, a Hilar cholangiocarcinoma cell, a squamous cell carcinoma cell of the oral cavity, a small-sized pulmonary adenocarcinoma cell, an ovarian cancer cell, a pancreatic cancer cell, a kidney cancer cell, a prostate cancer cell, an extranodal NK/T-cell lymphoma cell, nasal type (ENKTL), a stomach cancer cell, a thyroid cancer cell, a urinary bladder cancer cell, or a uterine cancer cell.

In some embodiments according to (or as applied to) any of the embodiments herein, the anti-TROP2 antibody or antigen binding fragment comprises: (i) a CDR-H1 comprising $GX_1X_2X_3TX_4YX_5X_6X_7$ (SEQ ID NO: 32), wherein $X_1$ is Y or F; $X_2$ is T or S; $X_3$ is F or L; $X_4$ is D or R; $X_5$ is S or G; $X_6$ is I, M, or V; and $X_7$ is H or N; (ii) a CDR-H2 comprising $WX_1GX_2IX_3X_4X_5X_6GX_7X_8X_9YX_{10}X_{11}X_{12}F$ (SEQ ID NO: 33), wherein $X_1$ is I, L, or M; $X_2$ is V or L; $X_3$ is S or W; $X_4$ is S or T; $X_5$ is Y, F, or G; $X_6$ is Y or no amino acid; $X_7$ is D or N; $X_8$ is A or T; $X_9$ is T, S, N, or D; $X_{10}$ is N or T; $X_{11}$ is Q or A; and $X_{12}$ is K or A; or $X_1X_2X_3X_4IX_5X_6X_7X_8GX_9X_{10}X_{11}YX_{12}X_{13}X_{14}FX_{15}X_{16}$ (SEQ ID NO: 103). wherein: $X_1$ is W or no amino acid; $X_2$ is L, M, I, or no amino acid; $X_3$ is G or no amino acid; $X_4$ is V or L; $X_5$ is S or W; $X_6$ is S or T; $X_7$ is Y, F, or G; $X_8$ is Y or no amino acid; $X_9$ is D or N; $X_{10}$ is A or T; $X_{11}$ is T, S, N, or D; $X_{12}$ is N or T; $X_{13}$ is Q or A; $X_{14}$ is K or A; $X_{15}$ is K, I, or no amino acid; and $X_{16}$ is G, S, or no amino acid; (iii) a CDR-H3 comprising $AX_1X_2X_3X_4X_5X_6X_7X_8X_9X_{10}Y$ (SEQ ID NO: 34), wherein $X_1$ is L or R; $X_2$ is L, Y, R, or E; $X_3$ is G or D; $X_4$ is D, R, or no amino acid; $X_5$ is A, G, N, or Y; $X_6$ is Y or V; $X_7$ is N, D, or G; $X_8$ is Y, Q, S, or E; $X_9$ is F or M; and $X_{10}$ is D or A; (iv) a CDR-L1 comprising $ESVDSYGNX_1FX_2H$ (SEQ ID NO: 35) wherein $X_1$ is N or S; and $X_2$ is M or I; or comprising $X_1X_2X_3ESVDSYGNX_4FX_5H$ (SEQ ID NO: 104), wherein $X_1$ is R or no amino acid; $X_2$ is A, V, or no amino acid; $X_3$ is S or no amino acid; $X_4$ is N or S; and $X_5$ is M or I; (v) a CDR-L2 comprising $X_1LX_2YRASNLES$ (SEQ ID NO: 36) wherein $X_1$ is L or R; and $X_2$ is I or V; or $X_1X_2X_3X_4RASNLES$ (SEQ ID NO: 105), wherein $X_1$ is L, R, or no amino acid; $X_2$ is L or no amino acid; $X_3$ is I, V, or no amino acid; and $X_4$ is Y or no amino acid; and (vi) a CDR-L3 comprising $QQSX_1EDPX_2T$ (SEQ ID NO 37) wherein: $X_1$ is N or Y; and $X_2$ is P, R, or Y.

In some embodiments according to (or as applied to) any of the embodiments herein, the anti-TROP2 antibody or antigen binding fragment comprises:

i) a CDR-H1 comprising the amino acid sequence of any one of SEQ ID NOs: 1-4, or a variant thereof comprising up to about 5 amino acid substitutions; ii) a CDR-H2 comprising the amino acid sequence of any one of SEQ ID NOs: 5-9, 39, 87-91, 95, and 96-101, or a variant thereof comprising up to about 5 amino acid substitutions; iii) a CDR-H3 comprising the amino acid sequence of any one of SEQ ID NOs: 10-13, or a variant thereof comprising up to about 5 amino acid substitutions; iv) a CDR-L1 comprising the amino acid sequence of any one of SEQ ID NOs: 14-16 and 92-94, or a variant thereof comprising up to about 5 amino acid substitutions; v) a CDR-L2 comprising the amino acid sequence of SEQ ID NOs: 17, 18, 38, and 102, or a variant thereof comprising up to about 3 amino acid substitutions; and vi) a CDR-L3 comprising the amino acid sequence of any one of SEQ ID NOs: 19-21, or a variant thereof comprising up to about 5 amino acid substitutions.

In some embodiments according to (or as applied to) any of the embodiments herein, the anti-TROP2 antibody or antigen binding fragment comprises: i) a CDR-H1 comprising the amino acid sequence of any one of SEQ ID NOs: 1-4; ii) a CDR-H2 comprising the amino acid sequence of any one of SEQ ID NOs: 5-9, 39, 87-91, 95, and 96-101; iii) a CDR-H3 comprising the amino acid sequence of any one of SEQ ID NOs: 10-13; iv) a CDR-L1 comprising the amino acid sequence of any one of SEQ ID NOs: 14-16 and 92-94; v) a CDR-L2 comprising the amino acid sequence of SEQ ID NOs: 17, 18, 38, and 102; and vi) a CDR-L3 comprising the amino acid sequence of any one of SEQ ID NOs: 19-21.

In some embodiments according to (or as applied to) any of the embodiments herein, the anti-TROP2 antibody or antigen binding fragment comprises: i) a CDR-H1 comprising the amino acid sequence of SEQ ID NO: 1 or a variant thereof comprising up to 5 amino acid substitutions; ii) a CDR-H2 comprising the amino acid sequence of SEQ ID NO: 5, 87, or 96, or a variant thereof comprising up to 5 amino acid substitutions; iii) a CDR-H3 comprising the amino acid sequence of SEQ ID NO: 10 or a variant thereof comprising up to 5 amino acid substitutions; iv) a CDR-L1 comprising the amino acid sequence of SEQ ID NO: 14 or 92, or a variant thereof comprising up to 5 amino acid substitutions; v) a CDR-L2 comprising the amino acid sequence of SEQ ID NO: 17 or 102, or a variant thereof comprising up to 5 amino acid substitutions; and vi) a CDR-L3 comprising the amino acid sequence of SEQ ID NO: 19 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO: 2 or a variant thereof comprising up to 5 amino acid substitutions; ii) a CDR-H2 comprising the amino acid sequence of SEQ ID NO: 6, 88, or 97, or a variant thereof comprising up to 5 amino acid substitutions; iii) a CDR-H3 comprising the amino acid sequence of SEQ ID NO: 11 or a variant thereof comprising up to 5 amino acid substitutions; iv) a CDR-L1 comprising the amino acid sequence of SEQ ID NO: 15 or 93, or a variant thereof comprising up to 5 amino acid substitutions; v) a CDR-L2 comprising the amino acid sequence of SEQ ID NO: 17 or 102, or a variant thereof comprising up to 5 amino acid substitutions; and vi) a CDR-L3 comprising the amino acid sequence of SEQ ID NO: 20 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO: 3 or a variant thereof comprising up to 5 amino acid substitutions; ii) a CDR-H2 comprising the amino acid sequence of SEQ ID NO: 7, 89, or 98, or a variant thereof comprising up to 5 amino acid substitutions; iii) a CDR-H3 comprising the amino acid sequence of SEQ ID NO: 12 or a variant thereof comprising up to 5 amino acid substitutions; iv) a CDR-L1 comprising the amino acid sequence of SEQ ID NO: 16 or 94, or a variant thereof comprising up to 5 amino acid substitutions; v) a CDR-L2 comprising the amino acid sequence of SEQ ID NO: 18 or 102, or a variant thereof comprising up to 5 amino acid substitutions; and vi) a CDR-L3 comprising the amino acid sequence of SEQ ID NO: 21 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO: 3 or a variant thereof comprising up to 5 amino acid substitutions; ii) a CDR-H2 comprising the amino acid sequence of SEQ ID NO: 8, 90, or 99, or a variant thereof comprising up to 5 amino acid substitutions; iii) a CDR-H3 comprising the amino acid sequence of SEQ ID NO: 12 or a variant thereof comprising up to 5 amino acid substitutions; iv) a CDR-L1 comprising the amino acid sequence of SEQ ID NO: 16 or 94, or a variant thereof comprising up to 5 amino acid substitutions; v) a CDR-L2 comprising the amino acid sequence of SEQ ID NO: 18 or 102, or a variant thereof comprising up to 5 amino acid substitutions; and vi) a CDR-L3 comprising the amino acid sequence of SEQ ID NO: 21 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO: 4 or a variant thereof comprising up to 5 amino acid substitutions; ii) a CDR-H2 comprising the amino acid sequence of SEQ ID NO: 9, 91, or 100, or a variant thereof comprising up to 5 amino acid substitutions; iii) a CDR-H3 comprising the amino acid sequence of SEQ ID NO: 13 or a variant thereof comprising up to 5 amino acid substitutions; iv) a CDR-L1 comprising the amino acid sequence of SEQ ID NO: 16 or 94, or a variant thereof comprising up to 5 amino acid substitutions; v) a CDR-L2 comprising the amino acid sequence of SEQ ID NO: 17 or 102, or a variant thereof comprising up to 5 amino acid substitutions; and vi) a CDR-L3 comprising the amino acid sequence of SEQ ID NO: 21 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO:1 or a variant thereof comprising up to 5 amino acid substitutions; ii) a CDR-H2 comprising the amino acid sequence of SEQ ID NO: 39, 95, or 101, or a variant thereof comprising up to 5 amino acid substitutions; iii) a CDR-H3 comprising the amino acid sequence of SEQ ID NO: 10 or a variant thereof comprising up to 5 amino acid substitutions; iv) a CDR-L1 comprising the amino acid sequence of SEQ ID NO: 14 or 92, or a variant thereof comprising up to 5 amino acid substitutions; v) a CDR-L2 comprising the amino acid sequence of SEQ ID NO: 17 or 102, or a variant thereof comprising up to 5 amino acid substitutions; and vi) a CDR-L3 comprising the amino acid sequence of SEQ ID NO: 19 or a variant thereof comprising up to 5 amino acid substitutions.

In some embodiments according to (or as applied to) any of the embodiments herein, the anti-TROP2 antibody or antigen binding fragment comprises: i) a CDR-H1 comprising the amino acid sequence of SEQ ID NO: 1 or a variant thereof comprising up to 5 amino acid substitutions; ii) a CDR-H2 comprising the amino acid sequence of SEQ ID NO: 39, 95, or 101 or a variant thereof comprising up to 5 amino acid substitutions; iii) a CDR-H3 comprising the amino acid sequence of SEQ ID NO: 10 or a variant thereof comprising up to 5 amino acid substitutions; iv) a CDR-L1 comprising the amino acid sequence of SEQ ID NO: 14 or 92, or a variant thereof comprising up to 5 amino acid substitutions; v) a CDR-L2 comprising the amino acid sequence of SEQ ID NO: 38 or 102, or a variant thereof comprising up to 5 amino acid substitutions; and vi) a CDR-L3 comprising the amino acid sequence of SEQ ID NO: 19 or a variant thereof comprising up to 5 amino acid substitutions.

In some embodiments according to (or as applied to) any of the embodiments herein, the anti-TROP2 antibody or antigen binding fragment comprises: i) a heavy chain variable domain ($V_H$) comprising SEQ ID NO1: 1; SEQ ID NO: 5, 87, or 96; and SEQ ID NO:10, and a light chain variable domain ($V_L$) comprising SEQ ID NO: 14 or 92; SEQ ID NO: 17 or 102; and SEQ ID NO:19; ii) a $V_H$ comprising SEQ ID NO: 2; SEQ ID NO: 6, 88, or 97; and SEQ ID NO: 11, and a $V_L$ comprising SEQ ID NO: 15 or 93; SEQ ID NO: 17 or 102; and SEQ ID NO: 20; iii) a $V_H$ comprising SEQ ID NO: 3; SEQ ID NO: 7, 89, or 98; and SEQ ID NO:12, and a $V_L$ comprising SEQ ID NO: 16 or 94; SEQ ID NO: 18 or 102; and SEQ ID NO: 21; iv) a $V_H$ comprising SEQ ID NO: 3; SEQ ID NO: 8, 90, or 99; and SEQ ID NO: 12, and a $V_L$ comprising SEQ ID NO: 16 or 94; SEQ ID NO: 18 or 102; and SEQ ID NO: 21; v) a $V_H$ comprising SEQ ID NO: 4; SEQ ID NO: 9, 91, or 100; and SEQ ID NO: 13, and a $V_L$ comprising SEQ ID NO: 16 or 94; SEQ ID NO: 17 or 102; and SEQ ID NO: 21; vi) a $V_H$ comprising SEQ ID NO: 1; SEQ ID NO: 39, 95, or 101; and SEQ ID NO: 10, and a $V_L$ comprising SEQ ID NO: 14 or 92; SEQ ID NO: 17 or 102; and SEQ ID NO: 19; or vi) a $V_H$ comprising SEQ ID NO: 1; SEQ ID NO: 39, 95, or 101; and SEQ ID NO: 10, and a $V_L$ comprising SEQ ID NO: 14 or 92; SEQ ID NO: 38 or 102; and SEQ ID NO: 19. In some embodiments according to (or as applied to) any of the embodiments herein, the anti-TROP2 antibody or antigen binding fragment comprises: i) a $V_H$ comprising a CDR-H1, a CDR-H2, and a CDR-H3 of any one of SEQ ID NOs: 22-26 and 40-45 and ii) a $V_L$ comprising domain a CDR-L1, a CDR-L2 and a CDR-L3 of any one of SEQ ID NOs: 27-31 and 46-51.

In some embodiments according to (or as applied to) any of the embodiments herein, the anti-TROP2 antibody or antigen binding fragment comprises: i) a $V_H$ comprising an amino acid sequence having at least about 90% identity to any one of SEQ ID NOs: 22-26 and 40-45; and ii) a $V_L$ comprising an amino acid sequence having at least about 90% identity to any one of SEQ ID NOs: 27-31 and 46-51. In some embodiments according to (or as applied to) any of the embodiments herein, the anti-TROP2 antibody or antigen binding fragment comprises i) a $V_H$ comprising the amino acid sequence of any one of SEQ ID NOs: 22-26 and 40-45; and a $V_L$ comprising the amino acid sequence of any one of SEQ ID NOs: 27-31 and 46-51. In some embodiments according to (or as applied to) any of the embodiments herein, the anti-TROP2 antibody or antigen binding fragment comprises a $V_H$ that comprises the amino acid sequence of SEQ ID NO: 22 and a $V_L$ that comprises the amino acid sequence of SEQ ID NO: 27. In some embodiments according to (or as applied to) any of the embodiments herein, the anti-TROP2 antibody or antigen binding fragment comprises a $V_H$ that comprises the amino acid sequence of SEQ ID NO: 23 and a $V_L$ that comprises the amino acid sequence of SEQ ID NO: 28. In some embodiments according to (or as applied to) any of the embodiments herein, the anti-TROP2 antibody or antigen binding fragment comprises a $V_H$ that comprises the amino acid sequence of SEQ ID NO: 24 and a $V_L$ that comprises the amino acid sequence of SEQ ID NO: 29. In some embodiments according to (or as applied to) any of the embodiments herein, the anti-TROP2 antibody or antigen binding fragment comprises a $V_H$ that comprises the amino acid sequence of SEQ ID NO: 25 and a $V_L$ that comprises the amino acid sequence of SEQ ID NO: 30. In some embodiments according to (or as applied to) any of the embodiments herein, the anti-TROP2 antibody or antigen binding fragment comprises a $V_H$ that comprises the amino acid sequence of SEQ ID NO: 26 and a $V_L$ that comprises the amino acid sequence of SEQ ID NO: 31. In some embodiments according to (or as applied to) any of the embodiments herein, the anti-TROP2 antibody or antigen binding fragment comprises a $V_H$ that comprises the amino acid sequence of SEQ ID NO: 45 and a $V_L$ that comprises the amino acid sequence of SEQ ID NO: 51.

In some embodiments according to (or as applied to) any of the embodiments herein, the anti-TROP2 antibody or antigen binding fragment comprises i) a $V_H$ comprising the amino acid sequence of SEQ ID NO: 40 and a $V_L$ comprising the amino acid sequence of SEQ ID NO: 46; ii) a $V_H$ comprising the amino acid sequence of SEQ ID NO: 40 and a $V_L$ comprising the amino acid sequence of SEQ ID NO: 47; iii) a $V_H$ comprising the amino acid sequence of SEQ ID NO: 40 and a $V_L$ comprising the amino acid sequence of SEQ ID NO: 48; iv) a $V_H$ comprising the amino acid sequence of SEQ ID NO: 40 and a $V_L$ comprising the amino acid sequence of SEQ ID NO: 49; v) a $V_H$ comprising the amino acid sequence of SEQ ID NO: 40 and a $V_L$ comprising the amino acid sequence of SEQ ID NO: 50; vi) a $V_H$ comprising the amino acid sequence of SEQ ID NO: 41 and a $V_L$ comprising the amino acid sequence of SEQ ID NO: 46; vii) a $V_H$ comprising the amino acid sequence of SEQ ID NO: 41 and a $V_L$ comprising the amino acid sequence of SEQ ID NO: 47; viii) a $V_H$ comprising the amino acid sequence of SEQ ID NO: 41 and a $V_L$ comprising the amino acid sequence of SEQ ID NO: 48; ix) a $V_H$ comprising the amino acid sequence of SEQ ID NO: 41 and a $V_L$ comprising the amino acid sequence of SEQ ID NO: 49; x) a $V_H$ comprising the amino acid sequence of SEQ ID NO: 41 and a $V_L$ comprising the amino acid sequence of SEQ ID NO: 50; xi) a $V_H$ comprising the amino acid sequence of SEQ ID NO: 42 and a $V_L$ comprising the amino acid sequence of SEQ ID NO: 46; xii) a Vu comprising the amino acid sequence of SEQ ID NO: 42 and a $V_L$ comprising the amino acid sequence of SEQ ID NO: 47; xiii) a $V_H$ comprising the amino acid sequence of SEQ ID NO: 42 and a $V_L$ comprising the amino acid sequence of SEQ ID NO: 48; xiv) a $V_H$ comprising the amino acid sequence of SEQ ID NO: 42 and a $V_L$ comprising the amino acid sequence of SEQ ID NO: 49; xv) a $V_H$ comprising the amino acid sequence of SEQ ID NO: 42 and a $V_L$ comprising the amino acid sequence of SEQ ID NO: 50; xvi) a $V_H$ comprising the amino acid sequence of SEQ ID NO: 43 and a $V_L$ comprising the amino acid sequence of SEQ ID NO: 46; xvii) a $V_H$ comprising the amino acid sequence of SEQ ID NO: 43 and a $V_L$ comprising the amino acid sequence of SEQ ID NO: 47; xviii) a $V_H$ comprising the amino acid sequence of SEQ ID NO: 43 and a $V_L$ comprising the amino acid sequence of SEQ ID NO: 48; xix) a $V_H$ comprising the amino acid sequence of SEQ ID NO: 43 and a $V_L$ comprising the amino acid sequence of SEQ ID NO: 49; xx) a $V_H$ comprising the amino acid sequence of SEQ ID NO: 43 and a $V_L$ comprising the amino acid sequence of SEQ ID NO: 50; xxi) a $V_H$ comprising the amino acid sequence of SEQ ID NO: 44 and a $V_L$ comprising the amino acid sequence of SEQ ID NO: 46; xxii) a $V_H$ comprising the amino acid sequence of SEQ ID NO: 44 and a $V_L$ comprising the amino acid sequence of SEQ ID NO:

47; xxiii) a $V_H$ comprising the amino acid sequence of SEQ ID NO: 44 and a $V_L$ comprising the amino acid sequence of SEQ ID NO: 48; xxiv) a $V_H$ comprising the amino acid sequence of SEQ ID NO: 44 and a $V_L$ comprising the amino acid sequence of SEQ ID NO: 49; or xxv) a $V_H$ comprising the amino acid sequence of SEQ ID NO: 44 and a $V_L$ comprising the amino acid sequence of SEQ ID NO: 50.

Also provided is an anti-TROP2 antibody or antigen-binding fragment thereof that competes for binding to TROP2 with an anti-TROP2 antibody or antigen binding fragment disclosed herein. Also provided is an anti-TROP2 antibody or antigen-binding fragment thereof that specifically binds the same epitope of TROP2 as an anti-TROP2 antibody or antigen-binding fragment thereof disclosed herein.

In some embodiments according to (or as applied to) any of the embodiments herein, the anti-TROP2 antibody comprises an Fc domain, wherein the antibody is a full length antibody. In some embodiments according to (or as applied to) any of the embodiments herein, the Fc domain is a human IgG Fc domain. In some embodiments according to (or as applied to) any of the embodiments herein, the human IgG Fc domain is an IgG1, IgG2, IgG3, or IgG4 Fc domain. In some embodiments according to (or as applied to) any of the embodiments herein, the human IgG Fc domain is an IgG1 Fc domain. In some embodiments according to (or as applied to) any of the embodiments herein, human IgG1 Fc domain comprises the amino acid sequence of SEQ ID NO: 64 or 65. In some embodiments according to (or as applied to) any of the embodiments herein, the anti-TROP2 antibody is chimeric, human, or humanized. In some embodiments according to (or as applied to) any of the embodiments herein, the antigen-binding fragment is selected from the group consisting of a Fab, a Fab', a F(ab)'2, a Fab'-SH, a single-chain Fv (scFv), an Fv fragment, and a linear antibody.

Provided is a nucleic acid encoding an isolated anti-TROP2 antibody or antigen-binding fragment thereof disclosed herein. Also provided is a vector comprising the nucleic acid according to (or as applied to) any of the embodiments herein. Also provided is a host cells comprising a nucleic acid according to (or as applied to) any of the embodiments herein, or the vector according to (or as applied to) any of the embodiments herein. Also provided is a method of producing an anti-TROP2 antibody or antigen-binding fragment thereof, comprising: a) culturing a host cell according to (or as applied to) any of the embodiments herein under conditions effective to cause expression of the anti-TROP2 antibody or antigen-binding fragment thereof; and b) recovering the anti-TROP2 antibody or antigen-binding fragment thereof expressed by the host cell.

Provided is an antibody-drug conjugate comprising the anti-TROP2 antibody or antigen-binding fragment thereof according to (or as applied to) any of the embodiments herein, specifically conjugated to a conjugate moiety. In some embodiments according to (or as applied to) any of the embodiments herein, the conjugate moiety comprises an active moiety selected from the group consisting of: a moiety that improves a pharmacokinetic property of the anti-TROP2 antibody or antigen-binding fragment, a therapeutic moiety, a diagnostic moiety, and a label. In some embodiments according to (or as applied to) any of the embodiments herein, the active moiety is a therapeutic moiety that comprises toxin. In some embodiments according to (or as applied to) any of the embodiments herein, the toxin is selected from the group consisting of: an auristatin, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides, and conotoxin. In some embodiments according to (or as applied to) any of the embodiments herein, the active moiety is a label, and wherein the label is selected from the group consisting of: a radioisotope, a fluorescent dye, and an enzyme. In some embodiments according to (or as applied to) any of the embodiments herein, the anti-TROP2 antibody or antigen-binding fragment thereof and the conjugate moiety are conjugated via a linker. In some embodiments according to (or as applied to) any of the embodiments herein, the linker is a cleavable linker. In some embodiments according to (or as applied to) any of the embodiments herein, the linker is a non-cleavable linker. In some embodiments according to (or as applied to) any of the embodiments herein, the anti-TROP2 antibody or antigen-binding fragment is conjugated to the conjugate moiety via an endogenous acceptor glutamine residue on the antibody.

Provided is a pharmaceutical composition comprising the conjugate according to (or as applied to) any of the embodiments herein, and a pharmaceutically acceptable carrier. Also provided is a method of treating cancer in an individual, comprising administering to the individual an effective amount of a conjugate according to (or as applied to) any of the embodiments herein, or a pharmaceutical composition according to (or as applied to) any of the embodiments herein. In some embodiments according to (or as applied to) any of the embodiments herein, the cancer is selected from solid tumor, breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, or uterine cancer. In some embodiments according to (or as applied to) any of the embodiments herein, the individual is further administered a therapeutic agent selected from the group consisting of: an anti-neoplastic agent, a chemotherapeutic agent, a growth inhibitory agent and a cytotoxic agent.

Provided is a method of detecting a TROP2 protein in sample from an individual comprising contacting a anti-TROP antibody or antigen binding fragment thereof according to (or as applied to) any of the embodiments herein, or a conjugate according to (or as applied to) to the sample and detecting the anti-TROP2 antibody bound to the TROP2 protein. In some embodiments according to (or as applied to) any of the embodiments herein, the anti-TROP2 antibody or antigen binding fragment thereof is used an immunohistochemistry assay (IHC) or in an ELISA assay.

BRIEF DESCRIPTION OF THE DRAWINGS

FIG. 2 shows the mean tumor volumes as a function of time during treatment with DP002-HC1LC5-ADC, DP002-HC4LC5-ADC, vehicle control, antibody control, or ADC control. FIG. 3 shows the % inhibition of tumor growth as a function of time during treatment with DP002-HC1LC5-ADC, DP002-HC4LC5-ADC, vehicle control, antibody control, or ADC control.

DETAILED DESCRIPTION OF THE INVENTION

Figure 1A:
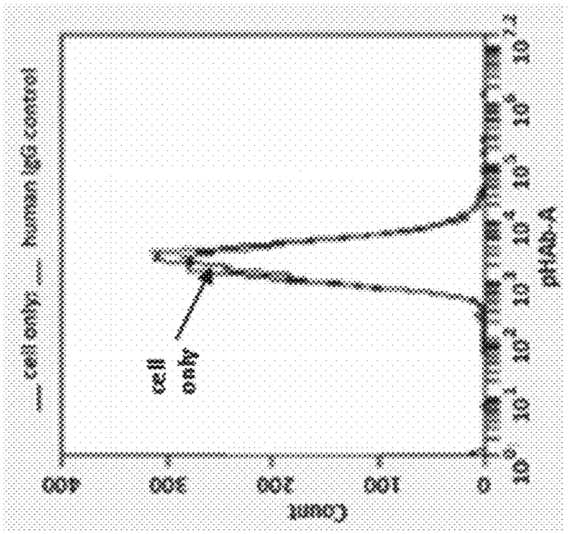
FIG. 1A is a flow cytometry (FACS) image showing that human IgG is not internalized by TROP2-expressing SKBR3 cells.
Figure 1B:
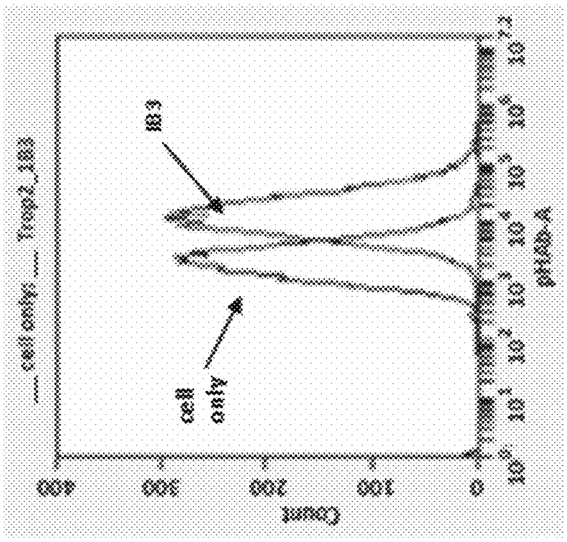
FIG. 1B shows the results of a flow cytometry experiment that was performed to verify that anti-TROP2 antibody 1B3 is internalized by TROP2-expressing SKBR3 cells.
Figure 1C:
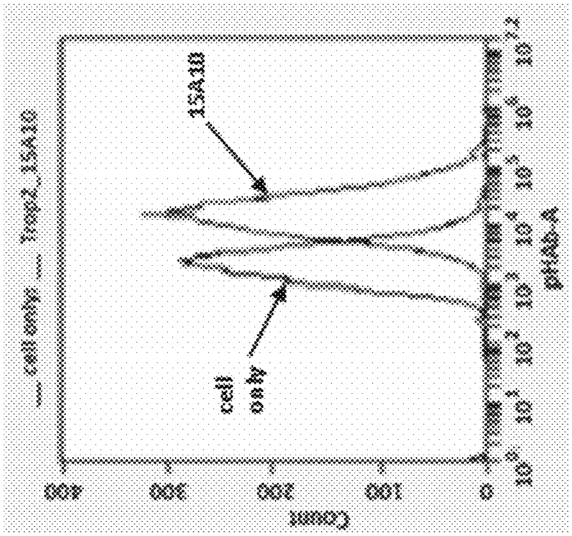
FIG. 1C shows the results of a flow cytometry experiment that was performed to verify that anti-TROP2 antibody 15A10 is internalized by TROP2-expressing SKBR3 cells.
Figure 1D:
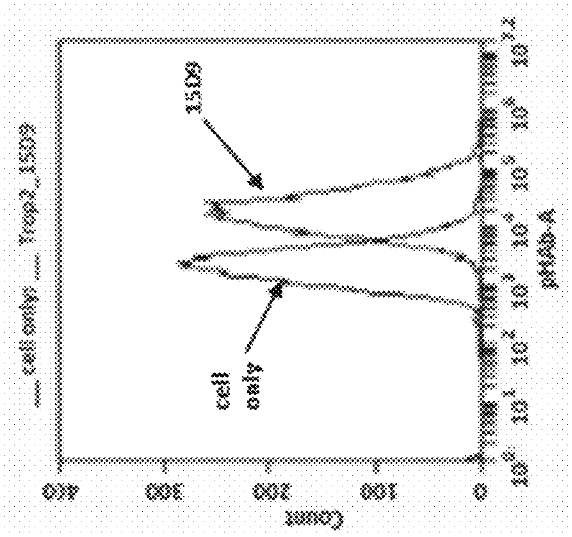
FIG. 1D shows the results of a flow cytometry experiment that was performed to verify that anti-TROP2 antibody 15D9 is internalized by TROP2-expressing SKBR3 cells.
Figure 1E:
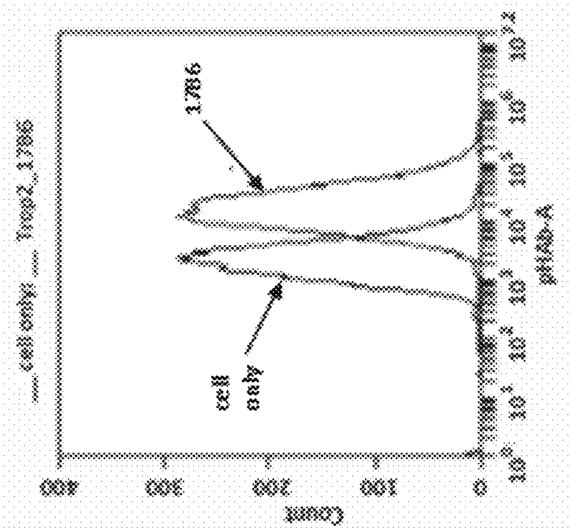
FIG. 1E shows the results of a flow cytometry experiment that was performed to verify that anti-TROP2 antibody 17B6 is internalized by TROP2-expressing SKBR3 cells.
Figure 1F:
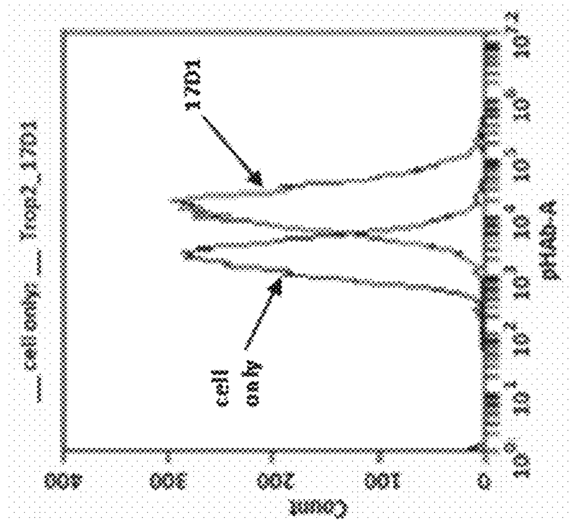
FIG. 1F shows the results of a flow cytometry experiment that was performed to verify that anti-TROP2 antibody 17D1 is internalized by TROP2-expressing SKBR3 cells.

The present disclosure provides anti-Trophoblast Cell Surface Antigen 2 (TROP2) antibodies. Also provided are immunoconjugates, nucleic acids encoding the novel anti-TROP2 antibodies described herein, and compositions (such as pharmaceutical compositions). The present disclosure also provides methods of using novel anti-TROP2 antibodies to detect TROP2 in a sample (such as an in vivo or ex vivo sample), compositions comprising such antibodies for use in treating cancer, and uses of such antibodies in the manufacture of a medicament for the treatment of cancer.

Definitions

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms “a”, “an” and “the” include plural referents unless the content clearly dictates otherwise. Thus, for example, reference to “a molecule” optionally includes a combination of two or more such molecules, and the like.

The term “about” as used herein refers to the usual error range for the respective value readily known to the skilled person in this technical field. Reference to “about” a value or parameter herein includes (and describes) embodiments that are directed to that value or parameter per se.

It is understood that aspects and embodiments of the present disclosure include “comprising,” “consisting,” and “consisting essentially of” aspects and embodiments.

The term “Trophoblast Cell Surface Antigen 2” or “TROP2” (which is also known as Tumor-Associated Calcium Signal Transducer 2 (TACSTD12), EGP1, GA7331/GA733-1, Gelatinous Drop-Like Corneal Dystrophy (GDLD), TTD2, GP50, and M1S1) preferably refers to human TROP2 and, in particular, to a protein comprising the amino acid sequence

```
                                        (SEQ ID NO: 86)
MARGPGLAPP PLRLPLLLLV LAAVTGHTAA QDNCTCPTNK

MTVCSPDGPG GRCQCRALGS GMAVDCSTLT SKCLLLKARM

SAPKNARTLV RPSEHALVDN DGLYDPDCDP EGRFKARQCN

QTSVCWCVNS VGVRRTDKGD LSLRCDELVR THHILIDLRH

RPTAGAFNHS DLDAELRRLF RERYRLHPKF VAAVHYEQPT

IQIELRQNTS QKAAGDVDIG DAAYYFERDI KGESLFQGRG

GLDLRVRGEP LQVERTLIYY LDEIPPKFSM KRLTAGLIAV

IVVVVVALVA GMAVLVITNR RKSGKYKKVE IKELGELRKE

PSL
```

or a variant of said amino acid sequence.

The term “TROP2” also refers to any post translationally modified variants and conformation variants.

As used herein, the term “antibody” may refer to intact (full length) antibodies; antibody fragments (including without limitation Fab, F(ab')2, Fab'-SH, Fv, diabodies, scFv, scFv-Fc, single domain antibodies, single heavy chain antibodies, and single light chain antibodies), provided that they exhibit the desired biological activity (e.g. epitope binding); monoclonal antibodies; polyclonal antibodies; monospecific antibodies; multi-specific antibodies (e.g., bispecific antibodies); and antibody-like proteins, including, but not limited to, e.g., fusion proteins, cysteine engineered antibodies, covalently modified antibodies, and antibody conjugates (such as antibody-drug conjugates or antibodies conjugated to detectable labels).

An “isolated” antibody may refer to an antibody that has been separated and/or recovered from a component of its natural environment, e.g., a host cell or organism. In some embodiments, an antibody is purified to a desired purity by weight (e.g., at least 95%); and/or homogeneity by SDS-PAGE using, for example, staining by silver, Coomassie, etc. In some embodiments, an isolated antibody is obtained following one or more purification steps.

As is known in the art, “native” antibodies refer to typically heterotetrameric complexes including two identical light (L) chains and two identical heavy (H) chains. Variable numbers of disulfide bonds connect the two heavy chains, and one connects each light chain to a heavy chain, in addition to intrachain disulfide bridges. The heavy chains include a variable domain (VH) followed (N-terminus to C-terminus) by three or four constant domains. The light chains include a variable domain (VL) followed by a constant domain (CL). Typically, mammalian light chains fall into one of two categories based on amino acid sequence: kappa and lambda.

A “constant domain” may refer to the more conserved portion of the antibody or fragment, e.g., outside the variable domains. The term may include the CL domain as well as heavy chain constant domains CH1, CH2, CH3 and optionally CH4.

Constant domains of the heavy chain can be assigned to one of 5 major types: IgA, IgD, IgE, IgG, and IgM. Several subtypes exist for many of these major types. The subunit structures and three-dimensional configurations of different classes of immunoglobulins are well known and described generally in, for example, Abbas et al., Cellular and Mol. Immunology, 4th ed. (W. B. Saunders, Co., 2000).

As used herein, the term "antibody variable domain" refers to the portions of the light and heavy chains of an antibody that include the complementary determining regions (CDRs, e.g., CDR L1, CDR L2, CDR L3, CDR H1, CDR H2, and CDR H3) and framework regions (FRs).

The term "variable" refers to the fact that subsequences of the variable domains differ substantially in sequence between antibodies and are critical to the binding specificity of a particular antibody for its antigen. Variability is concentrated in three "hypervariable regions" (HVRs) or "complementarity determining regions" (CDRs) in both VH and VL domains. (The terms "HVR" and "CDR" are used interchangeably herein.) The more conserved portions of variable domains are called the framework regions (FR) in which the CDRs are interspersed. The variable domains of native heavy and light chains each comprise four FR regions connected by three CDRs that form loops (see Kabat et al., Sequences of Proteins of Immunological Interest, Fifth Edition, National Institute of Health, Bethesda, Md. (1991)).

The term "hypervariable region (HVR)" or "complementarity determining region (CDR)" may refer to the subregions of the VH and VL domains characterized by enhanced sequence variability and/or formation of defined loops. These include three CDRs in the VH domain (H1, H2, and H3) and three CDRs in the VL domain (L1, L2, and L3). H3 is believed to be critical in imparting fine binding specificity, with L3 and H3 showing the highest level of diversity. See Johnson and Wu, in Methods in Molecular Biology 248:1-25 (Lo, ed., Human Press, Totowa, N.J., 2003).

A number of CDR/HVR delineations are known. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs/CDRs are noted below. "Framework" or "FR" residues are those variable domain residues other than the HVR/CDR residues.

| Loop | Kabat | Abm | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H31-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

"Extended" HVRs are also known: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH (Kabat numbering).

"Numbering according to Kabat" may refer to the numbering system used for heavy chain variable domains or light chain variable domains of the compilation of antibodies in Kabat et al., supra. The actual linear amino acid sequence may contain fewer or additional amino acids corresponding to a shortening of, or insertion into, a FR or HVR of the variable domain. The Kabat numbering of residues may be determined for a given antibody by alignment at regions of homology of the sequence of the antibody with a "standard" Kabat numbered sequence. Typically, the Kabat numbering is used when referring to a residue in the variable domains (approximately residues 1-107 of the light chain and residues 1-113 of the heavy chain), whereas the EU numbering system or index (e.g., the EU index as in Kabat, numbering according to EU IgG1) is generally used when referring to a residue in the heavy chain constant region.

"Full length" or "intact" antibodies typically include heavy chains with an Fc region, e.g., as opposed to an antibody fragment. Antigen-binding "Fab" fragments with a single antigen binding site may be released from the residual Fc fragment by papain digestion. F(ab')2 fragments include two antigen-binding sites produced by pepsin treatment of an antibody. Antibody fragments will, however, include one or more antibody variable regions.

An "Fv" fragment contains a complete antigen-binding site. A single chain Fv (scFv) can include a VH and a VL domain linked by a peptide linker such that the VH and VL domains associate, e.g., as in an antibody or Fab fragment, such that the HVRs form an antigen binding site. See Pluckthiln, in The Pharmacology of Monoclonal Antibodies, vol. 113, Rosenburg and Moore eds., (Springer-Verlag, New York, 1994), pp. 269-315. In some embodiments, the scFv is fused to an antibody Fc domain (e.g., scFv-Fc). While six HVRs typically comprise an antigen binding site, a single variable domain with three HVRs is still capable of binding an antigen, albeit at a lower affinity. See Hamers-Casterman et al., Nature 363:446-448 (1993); Sheriff et al., Nature Struct. Biol. 3:733-736 (1996). Single domain antibodies (e.g., camelid antibodies) typically include a single, monomeric variable domain for antigen binding. Single heavy chain (VHH) and single light chain antibodies are also known. A Fab' fragment typically includes a few more residues at the C-terminal end than a Fab fragment. A Fab'-SH includes cysteine residues with a free thiol. Various chemical couplings of antibody fragments are known in the art.

A "diabody" includes antibody fragments with two antigen-binding sites. These include a VH and VL domain connected by a linker, which is typically too short to facilitate pairing of domains in the same chain. Diabodies may be bivalent or bispecific. Tribodies and tetrabodies, or other numbers of VH/VL domains are known. See Hudson et al., Nat. Med. 9:129-134 (2003).

As used herein, a "monoclonal" antibody refers to an antibody obtained from a population of substantially homogeneous antibodies, e.g., substantially identical but allowing for minor levels of background mutations and/or modifications. "Monoclonal" denotes the substantially homogeneous character of antibodies, and does not require production of the antibody by any particular method. In some embodiments, a monoclonal antibody is selected by its HVR, VH, and/or VL sequences and/or binding properties, e.g., selected from a pool of clones (e.g., recombinant, hybridoma, or phage-derived). A monoclonal antibody may be engineered to include one or more mutations, e.g., to affect binding affinity or other properties of the antibody, create a humanized or chimeric antibody, improve antibody production and/or homogeneity, engineer a multispecific antibody, resultant antibodies of which are still considered to be monoclonal in nature. A population of monoclonal antibodies may be distinguished from polyclonal antibodies as the individual monoclonal antibodies of the population recognize the same antigenic site. A variety of techniques for production of monoclonal antibodies are known; see, e.g., the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

"Chimeric" antibodies may refer to an antibody with one portion of the heavy and/or light chain from a particular isotype, class, or organism and another portion from another isotype, class, or organism. In some embodiments, the variable region will be from one source or organism, and the constant region will be from another.

"Humanized antibodies" may refer to antibodies with predominantly human sequence and a minimal amount of non-human (e.g., mouse or chicken) sequence. In some embodiments, a humanized antibody has one or more HVR sequences (bearing a binding specificity of interest) from an antibody derived from a non-human (e.g., mouse or chicken) organism grafted onto a human recipient antibody framework (FR). In some embodiments, non-human residues are further grafted onto the human framework (not present in either source or recipient antibodies), e.g., to improve antibody properties. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See Jones et al., Nature 321:522-525 (1986); Riechmann et al., Nature 332:323-329 (1988); and Presta, Curr. Op. Struct. Biol. 2:593-596 (1992).

A "human" antibody may refer to an antibody having an amino acid sequence which corresponds to that of an antibody produced by a human and/or has been made using any of the techniques for making human antibodies as disclosed herein. Human antibodies can be produced using various techniques known in the art, including phage-display libraries. Hoogenboom and Winter, J. Mol. Biol., 227:381 (1991); Marks et al., J. Mol. Biol., 222:581 (1991); preparation of human monoclonal antibodies as described in Cole et al., Monoclonal Antibodies and Cancer Therapy, Alan R. Liss, p. 77 (1985); Boerner et al., J. Immunol., 147(1):86-95 (1991); and by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology) or chickens with human immunoglobulin sequence(s) (see, e.g., WO2012162422, WO2011019844, and WO2013059159).

The term "cytotoxic agent" as used herein may refer to any agent that inhibits cellular proliferation or induces cell death. Cytotoxic agents include, but are not limited to, chemotherapeutic agents; radioactive isotopes; growth inhibitory agents; and toxins such as small molecule toxins or enzymatically active toxins, including fragments and/or variants thereof. Exemplary cytotoxic agents include without limitation metabolic inhibitors, anti-microtubule agents, platinum containing compounds, alkylating agents, proteasome inhibitors, topoisomerase II inhibitors, antimetabolites, topoisomerase I inhibitors, signal transduction pathway inhibitors, non-receptor tyrosine kinase angiogenesis inhibitors, hormones and hormonal analogues, proapoptotic agents, inhibitors of LDH-A, cell cycle inhibitors, HDAC inhibitors, and antibiotic agents.

As used herein, a "label" may include any moiety that serves as a detection agent, e.g., of binding between a labeled antibody of the present disclosure and a macromolecule or cell. Exemplary labels include without limitation fluorescent (e.g., compounds or proteins), radioactive, or enzymatic moieties, as well as affinity purification tags.

The term "detecting" is intended to include determining the presence or absence of a substance or quantifying the amount of a substance (such as TROP2). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of a TROP2 gene product or a TROP2 polypeptide; a change in the levels of a TROP2 polypeptide or amount bound to a target; a change in biological function/activity of a TROP2 polypeptide. In some embodiments, "detecting" may include detecting wild type TROP2 levels (e.g., polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

As used herein, an antibody may be said to "bind" an antigen with an affinity sufficient to render the antibody useful for in vitro and/or in vivo manipulation of the antigen.

As used herein, the term "affinity" or "binding affinity" refers to the strength of the binding interaction between two molecules. Generally, binding affinity refers to the strength of the sum total of non-covalent interactions between a molecule and its binding partner, such as a high affinity SIRP-α D1 variant and CD47. Unless indicated otherwise, binding affinity refers to intrinsic binding affinity, which reflects a 1:1 interaction between members of a binding pair. The binding affinity between two molecules is commonly described by the dissociation constant ($K_d$) or the association constant ($K_a$). Two molecules that have low binding affinity for each other generally bind slowly, tend to dissociate easily, and exhibit a large $K_d$. Two molecules that have high affinity for each other generally bind readily, tend to remain bound longer, and exhibit a small $K_d$. In some embodiments, the $K_d$ of two interacting molecules is determined using known methods and techniques, e.g., surface plasmon resonance (SPR). $K_d$ can be calculated as the ratio of koff/kon.

As used herein, the term "$K_d$ less than" refers to a numerically smaller $K_d$ value and an increasing binding affinity relative to the recited $K_d$ value. As used herein, the term "$K_d$ greater than" refers to a numerically larger $K_d$ value and a decreasing binding affinity relative to the recited $K_d$ value.

As used herein, "treatment" may refer to therapeutic administration of a molecule, compound, formulation, composition, etc. to obtain beneficial or desired therapeutic results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, palliating a pathological symptom or disease state, increasing or improving the quality of life, preventing excessive weight loss, improving prognosis, achieving disease remission and/or prolonging survival. Also encompassed by "treatment" is a reduction of pathological consequence of cancer (such as, for example, tumor volume). The methods provided herein contemplate any one or more of these aspects of treatment.

As used herein, "delaying progression" of a disease may refer to slowing, retarding, deferring, postponing development of, stabilizing, or otherwise hindering the pathological course of the disease. In some embodiments, the term may refer to a delay sufficient to effectively encompass prevention, e.g., in preventing the individual from developing the disease. In some embodiments, e.g., an advanced cancer, delaying progression may include delaying metastasis. One of skill in the art will appreciate that the precise length of delay may depend, e.g., upon the specific disease, condition of the individual, and the like.

The terms "recurrence," "relapse" or "relapsed" refers to the return of a disease or disorder characterized by abnormal TROP2 expression or abnormal TROP2 activity (e.g., a tumor, such as solid tumor, or cancer, such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) resulting from after clinical assessment of the disappearance of disease.

The term "refractory" or "resistant" refers to a disease or disorder characterized by abnormal TROP2 expression or abnormal TROP2 activity (e.g., a tumor, such as solid tumor, or cancer, such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) that has not responded to treatment with a particular agent or combination of agents.

As used herein, the term "effective amount" may refer to an amount of an antibody of the present disclosure or a pharmaceutical composition containing an antibody of the present disclosure that is sufficient and effective in achieving a desired therapeutic effect in treating or delaying progression of a patient having a disease, such as TROP2-expressing tumor or a cancer characterized by abnormal TROP2 expression or activity, e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc. In some embodiments, a therapeutically effective amount will avoid adverse side effects, and/or such side effects will be outweighed by beneficial effects. An effective amount may depend upon the individual being treated, e.g., age, weight, sex, disease state, as well as the ability of the agent to produce a desired response. An effective amount can be administered in one or more administrations. As in the clinical context, an effective amount of a drug, compound, or pharmaceutical composition may or may not be achieved in conjunction with another drug, compound, or pharmaceutical composition, such as another therapeutic agent. Thus, an "effective amount" may also be considered in the context of administering one or more additional therapeutic agents, and a single agent may be considered to be given in an effective amount if, in conjunction with one or more other agents, a desirable result may be or is achieved.

The term "therapeutically effective amount" refers to an amount of an anti-TROP2 antibody drug conjugate ("anti-TROP2 ADC," or simply "ADC") described herein or a composition comprising such anti-TROP2 ADC effective to "treat" a disease or disorder in a mammal (aka patient or subject). In the case of cancer, a therapeutically effective amount of an anti-TROP2 ADC disclosed herein is an amount sufficient to treat, e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc. Treatment with anti-TROP2 ADC or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-TROP2 ADC or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

As used herein, the term "pharmaceutical composition" may refer to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with one or more anti-TROP2 antibodies or anti-TROP2 ADC of the present disclosure. In some embodiments, the pharmaceutical composition is in tablet or capsule form for oral administration or in aqueous form for intravenous or subcutaneous administration, for example by injection.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, the terms "subject," "individual," and "patient" are used interchangeably to refer to a vertebrate, for example, a mammal. Mammals include, but are not limited to, murines, simians, humans, farm animals, sport animals, and pets.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California The ALIGN-2 program should be compiled for use on a UNIX operating system, preferably digital UNIX V4.0D. All sequence comparison parameters are set by the ALIGN-2 program and do not vary.

All references cited herein, including patent applications and publications, are hereby incorporated by reference in their entirety.

Overview

The present disclosure is based on the identification of antibodies that bind Trophoblast Cell Surface Antigen 2 (TROP2). The anti-TROP2 antibodies provided herein may be used in the preparation of anti-TROP2 antibody drug conjugates (anti-TROP2 ADC, or simply "ADC"). Such anti-TROP2 ADC may be in a variety of therapeutic methods. For example, the anti-TROP2 ADC may be used alone or in combination with other agents in treating a disease or disorder characterized by abnormal TROP2 expression or abnormal TROP2 activity, including, but not limited to solid tumor, or cancer, such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc. The antibodies provided herein can also be used diagnostic methods, e.g., in detecting TROP2 in patients or patient samples by, e.g., administering an anti-TROP2 antibody to a patient and detecting the anti-TROP2 antibody bound to TROP2 (e.g., using in vivo or ex vivo methods), or, e.g., by contacting a sample (e.g., ex vivo sample) from a patient with an anti-TROP2 antibody and qualitatively or quantitatively detecting the anti-TROP2 antibody bound to the TROP2 protein in the sample.

Anti-Trophoblast Cell Surface Antigen 2 (TROP2) Antibodies

An anti-TROP2 antibody is an antibody that binds to TROP2 with sufficient affinity and specificity. For example, an anti-TROP2 antibody provided herein (or a biologically active fragment thereof) may be used as a therapeutic agent in targeting and interfering with diseases or conditions associated with aberrant/abnormal TROP2 expression and/or activity. In some, the anti-TROP2 antibody is a chimeric monoclonal antibody. In some embodiments, the anti-TROP2 antibody comprises at least one CDR, a heavy chain variable domain (VH), and/or a light chain variable domain (VL) of an antibody disclosed herein.

In certain embodiments, an anti-TROP2 antibody provided herein (or antigen binding fragment thereof) comprises one, two, three, four, five, or six complementarity determining region (CDR) sequences selected from: (i) a CDR-H1 comprising $GX_1X_2X_3TX_4YX_5X_6X_7$ (SEQ ID NO: 32), wherein $X_1$ is Y or F; $X_2$ is T or S; $X_3$ is F or L; $X_4$ is D or R; $X_5$ is S or G; $X_6$ is I, M, or V; and $X_7$ is H or N; (ii) a CDR-H2 comprising $WX_1GX_2IX_3X_4X_5X_6GX_7X_8X_9YX_{10}X_{11}X_{12}F$ (SEQ ID NO: 33), wherein $X_1$ is I, L, or M; $X_2$ is V or L; $X_3$ is S or W; $X_4$ is S or T; $X_5$ is Y, F, or G; $X_6$ is Y or no amino acid; $X_7$ is D or N; $X_8$ is A or T; $X_9$ is T, S, N, or D; $X_{10}$ is N or T; $X_{11}$ is Q or A; and $X_{12}$ is K or A; (iii) a CDR-H3 comprising $AX_1X_2X_3X_4X_5X_6X_7X_8X_9X_{10}Y$ (SEQ ID NO: 34), wherein $X_1$ is L or R; $X_2$ is L, Y, R, or E; $X_3$ is G or D; $X_4$ is D, R, or no amino acid; $X_5$ is A, G, N, or Y; $X_6$ is Y or V; $X_7$ is N, D, or G; $X_8$ is Y, Q, S, or E; $X_9$ is F or M; and $X_{10}$ is D or A; (iv) a CDR-L1 comprising $ESVDSYGNX_1FX_2H$ (SEQ ID NO: 35) wherein $X_1$ is N or S; and $X_2$ is M or I; (v) a CDR-L2 comprising $X_1LX_2YRASNLES$ (SEQ ID NO: 36) wherein $X_1$ is L or R; and $X_2$ is I or V; and (vi) a CDR-L3 comprising $QQSX_1EDPX_2T$ (SEQ ID NO 37) wherein: $X_1$ is N or Y; and $X_2$ is P, R, or Y.

In certain embodiments, an anti-TROP2 antibody provided herein (or antigen binding fragment thereof) comprises: (i) a CDR-H1 comprising $GX_1X_2X_3TX_4YX_5X_6X_7$ (SEQ ID NO: 32), wherein $X_1$ is Y or F; $X_2$ is T or S; $X_3$ is F or L; $X_4$ is D or R; $X_5$ is S or G; $X_6$ is I, M, or V; and $X_7$ is H or N; (ii) a CDR-H2 comprising $WX_1GX_2IX_3X_4X_5X_6GX_7X_8X_9YX_{10}X_{11}X_{12}F$ (SEQ ID NO: 33), wherein $X_1$ is I, L, or M; $X_2$ is V or L; $X_3$ is S or W; $X_4$ is S or T; $X_5$ is Y, F, or G; $X_6$ is Y or no amino acid; $X_7$ is D or N; $X_8$ is A or T; $X_9$ is T, S, N, or D; $X_{10}$ is N or T; $X_{11}$ is Q or A; and $X_{12}$ is K or A; (iii) a CDR-H3 comprising $AX_1X_2X_3X_4X_5X_6X_7X_8X_9X_{10}Y$ (SEQ ID NO: 34), wherein $X_1$ is L or R; $X_2$ is L, Y, R, or E; $X_3$ is G or D; $X_4$ is D, R, or no amino acid; $X_5$ is A, G, N, or Y; $X_6$ is Y or V; $X_7$ is N, D, or G; $X_8$ is Y, Q, S, or E; $X_9$ is F or M; and $X_{10}$ is D or A; (iv) a CDR-L1 comprising $ESVDSYGNX_1FX_2H$ (SEQ ID NO: 35) wherein $X_1$ is N or S; and $X_2$ is M or I; (v) a CDR-L2 comprising $X_1LX_2YRASNLES$ (SEQ ID NO: 36) wherein $X_1$ is L or R; and $X_2$ is I or V; and (vi) a CDR-L3 comprising $QQSX_1EDPX_2T$ (SEQ ID NO 37) wherein: $X_1$ is N or Y; and $X_2$ is P, R, or Y.

In certain embodiments, an anti-TROP2 antibody provided herein (or antigen binding fragment thereof) comprises one, two, three, four, five, or six complementarity determining region (CDR) sequences selected from: (i) a CDR-H1 comprising $GX_1X_2X_3TX_4YX_5X_6X_7$ (SEQ ID NO: 32), wherein $X_1$ is Y or F; $X_2$ is T or S; $X_3$ is F or L; $X_4$ is D or R; $X_5$ is S or G; $X_6$ is I, M, or V; and $X_7$ is H or N; (ii) a CDR-H2 comprising $X_1X_2X_3X_4IX_5X_6X_7X_8GX_9X_{10}X_{11}YX_{12}X_{13}X_{14}FX_{15}X_{16}$ (SEQ ID NO: 103). wherein: $X_1$ is W or no amino acid; $X_2$ is L, M, I, or no amino acid; $X_3$ is G or no amino acid; $X_4$ is V or L; $X_5$ is S or W; $X_6$ is S or T; $X_7$ is Y, F, or G; $X_8$ is Y or no amino acid; $X_9$ is D or N; $X_{10}$ is A or T; $X_{11}$ is T, S, N, or D; $X_{12}$ is N or T; $X_{13}$ is Q or A; $X_{14}$ is K or A; $X_{15}$ is K, I, or no amino acid; and $X_{16}$ is G, S, or no amino acid; (iii) a CDR-H3 comprising $AX_1X_2X_3X_4X_5X_6X_7X_8X_9X_{10}Y$ (SEQ ID NO: 34), wherein $X_1$ is L or R; $X_2$ is L, Y, R, or E; $X_3$ is G or D; $X_4$ is D, R, or no amino acid; $X_5$ is A, G, N, or Y; $X_6$ is Y or V; $X_7$ is N, D, or G; $X_8$ is Y, Q, S, or E; $X_9$ is F or M; and $X_{10}$ is D or A; (iv) a CDR-L1 comprising $X_1X_2X_3ESVDSYGNX_4FX_5H$ (SEQ ID NO: 104), wherein $X_1$ is R or no amino acid; $X_2$ is A, V, or no amino acid; $X_3$ is S or no amino acid; $X_4$ is N or S; and $X_5$ is M or I; (v) a CDR-L2 comprising $X_1X_2X_3X_4RASNLES$ (SEQ ID NO: 105), wherein $X_1$ is L, R, or no amino acid; $X_2$ is L or no amino acid; $X_3$ is I, V, or no amino acid; and $X_4$ is Y or no amino acid; and (vi) a CDR-L3 comprising $QQSX_1EDPX_2T$ (SEQ ID NO 37) wherein: $X_1$ is N or Y; and $X_2$ is P, R, or Y.

In certain embodiments, an anti-TROP2 antibody provided herein (or antigen binding fragment thereof) comprises: (i) a CDR-H1 comprising $GX_1X_2X_3TX_4YX_5X_6X_7$ (SEQ ID NO: 32), wherein $X_1$ is Y or F; $X_2$ is T or S; $X_3$ is F or L; $X_4$ is D or R; $X_5$ is S or G; $X_6$ is I, M, or V; and $X_7$ is H or N; (ii) a CDR-H2 comprising $X_1X_2X_3X_4IX_5X_6X_7X_8GX_9X_{10}X_{11}YX_{12}X_{13}X_{14}FX_{15}X_{16}$ (SEQ ID NO: 103). wherein: $X_1$ is W or no amino acid; $X_2$ is L, M, I, or no amino acid; $X_3$ is G or no amino acid; $X_4$ is V or L; $X_5$ is S or W; $X_6$ is S or T; $X_7$ is Y, F, or G; $X_8$ is Y or no amino acid; $X_9$ is D or N; $X_{10}$ is A or T; $X_{11}$ is T, S, N, or D; $X_{12}$ is N or T; $X_{13}$ is Q or A; $X_{14}$ is K or A; $X_{15}$ is K, I, or no amino acid; and $X_{16}$ is G, S, or no amino acid; (iii) a CDR-H3 comprising $AX_1X_2X_3X_4X_5X_6X_7X_8X_9X_{10}Y$ (SEQ ID NO: 34), wherein $X_1$ is L or R; $X_2$ is L, Y, R, or E; $X_3$ is G or D; $X_4$ is D, R, or no amino acid; $X_5$ is A, G, N, or Y; $X_6$ is Y or V; $X_7$ is N, D, or G; $X_8$ is Y, Q, S, or E; $X_9$ is F or M; and $X_{10}$ is D or A; (iv) a CDR-L1 comprising $X_1X_2X_3ESVDSYGNX_4FX_5H$ (SEQ ID NO: 104), wherein $X_1$ is R or no amino acid; $X_2$ is A, V, or no amino acid; $X_3$ is S or no amino acid; $X_4$ is N or S; and $X_5$ is M or I; (v) a CDR-L2 comprising $X_1X_2X_3X_4RASNLES$ (SEQ ID NO: 105), wherein $X_1$ is L, R, or no amino acid; $X_2$ is L or no amino acid; $X_3$ is I, V, or no amino acid; and $X_4$ is Y or no amino acid; and (vi) a CDR-L3 comprising $QQSX_1EDPX_2T$ (SEQ ID NO 37) wherein: $X_1$ is N or Y; and $X_2$ is P, R, or Y.

In certain embodiments, provided is an anti-TROP2 antibody (or antigen-binding fragment thereof) that specifically binds anti-TROP2 and competes for binding to anti-TROP2 with a second anti-TROP2 antibody that comprises: (i) a CDR-H1 comprising the amino acid sequence of any one of SEQ ID NOs: 1-4; (ii) a CDR-H2 comprising the amino acid sequence of any one of SEQ ID NOs: 5-9, 39, 87-91, 95, and 96-101; (iii) a CDR-H3 comprising the amino acid sequence of any one of SEQ ID NOs: 10-13; (iv) a CDR-L1 comprising the amino acid sequence of any one of SEQ ID NOs: 14-16 and 92-94; (v) a CDR-L2 comprising the amino acid sequence of SEQ ID NOs: 17, 18, 38, and 102; and (vi) a CDR-L3 comprising the amino acid sequence of any one of SEQ ID NOs: 19-21.

In certain embodiments, provided is an anti-TROP2 antibody (or antigen-binding fragment thereof) that specifically binds to the same epitope of TROP2 as a second anti-TROP2 antibody that comprises (i) a CDR-H1 comprising the amino acid sequence of any one of SEQ ID NOs: 1-4; (ii) a CDR-H2 comprising the amino acid sequence of any one of SEQ ID NOs: 5-9, 39, 87-91, 95, and 96-101; (iii) a CDR-H3 comprising the amino acid sequence of any one of SEQ ID NOs: 10-13; (iv) a CDR-L1 comprising the amino acid sequence of any one of SEQ ID NOs: 14-16 and 92-94; (v) a CDR-L2 comprising the amino acid sequence of SEQ ID NOs: 17, 18, 38, and 102; and (vi) a CDR-L3 comprising the amino acid sequence of any one of SEQ ID NOs: 19-21.

In certain embodiments, the anti-TROP2 antibody (or antigen binding fragment thereof) comprises one, two, three, four, five, or six complementarity determining region (CDR) sequences selected from: (i) a CDR-H1 comprising an amino acid sequence set forth in any one of SEQ ID NOs: 1-4 or a variant thereof comprising up to about 5 (such as about any of 1, 2, 3, 4, or 5) amino acid substitutions; (ii) a CDR-H2 comprising an amino acid sequence set forth in any one of SEQ ID NOs: 5-9, 39, 87-91, 95, and 96-101 or a variant thereof comprising up to about 5 (such as about any of 1, 2, 3, 4, or 5) amino acid substitutions (iii) a CDR-H3 comprising an amino acid sequence set forth in any one of SEQ ID NOs: 10-13 or a variant thereof comprising up to about 5 (such as about any of 1, 2, 3, 4, or 5) amino acid substitutions; (iv) a CDR-L1 comprising an amino acid sequence set forth in any one of SEQ ID NOs: 14-16 and 92-94, or a variant thereof comprising up to about 5 (such as about any of 1, 2, 3, 4, or 5) amino acid substitutions; (v) a CDR-L2 comprising an amino acid sequence set forth in any one of SEQ ID NOs: 17, 18, 38, and 102 or a variant thereof comprising up to about 5 (such as about any of 1, 2, 3, 4, or 5) amino acid substitutions; and (vi) a CDR-L3 comprising an amino acid sequence set forth in any one of SEQ ID NOs:

19-21 or a variant thereof comprising up to about 5 (such as about any of 1, 2, 3, 4, or 5) amino acid substitutions.

In certain embodiments, the anti-TROP2 antibody (or antigen binding fragment thereof) comprises a CDR-H3 comprising an amino acid sequence set forth in any one of SEQ ID NOs: 10-13 and/or a CDR-L3 comprising an amino acid sequence set forth in any one of SEQ ID NOs: 19-21.

In certain embodiments, the anti-TROP2 antibody (or antigen binding fragment thereof) comprises one, two, three, four, five, or six complementarity determining region (CDR) sequences selected from: (i) a CDR-H1 comprising an amino acid sequence set forth in any one of SEQ ID NOs: 1-4; (ii) a CDR-H2 comprising an amino acid sequence set forth in any one of SEQ ID NOs: 5-9, 39, 87-91, 95, and 96-101; (iii) a CDR-H3 comprising an amino acid sequence set forth in any one of SEQ ID NOs: 10-13; (iv) a CDR-L1 comprising an amino acid sequence set forth in any one of SEQ ID NOs: 14-16 and 92-94; (v) a CDR-L2 comprising an amino acid sequence set forth in any one of SEQ ID NOs: 17, 18, 38, and 102; and (vi) a CDR-L3 comprising an amino acid sequence set forth in any one of SEQ ID NOs: 19-21.

In certain embodiments, the anti-TROP2 antibody (or antigen binding fragment thereof) comprises: (i) a CDR-H1 comprising an amino acid sequence set forth in any one of SEQ ID NOs: 1-4; (ii) a CDR-H2 comprising an amino acid sequence set forth in any one of SEQ ID NOs: 5-9, 39, 87-91, 95, and 96-101; (iii) a CDR-H3 comprising an amino acid sequence set forth in any one of SEQ ID NOs: 10-13; (iv) a CDR-L1 comprising an amino acid sequence set forth in any one of SEQ ID NOs: 14-16 and 92-94; (v) a CDR-L2 comprising an amino acid sequence set forth in any one of SEQ ID NOs: 17, 18, 38, and 102; and (vi) a CDR-L3 comprising an amino acid sequence set forth in any one of SEQ ID NOs: 19-21.

The amino acid sequences of SEQ ID NOs: 1-21, 38-39, 87-95, and are provided in Table 1 below.

TABLE 1

| | | | |
|---|---|---|---|
| GYTFTDYSIN (SEQ ID NO: 1) | GFSLTRYGVH (SEQ ID NO: 2) | GYTFTDYSIH (SEQ ID NO: 3) | GYTFTDYGMN (SEQ ID NO: 4) |
| WIGVISTYYG DASYNQKF (SEQ ID NO: 5) | WLGVIWSGGN TDYNAAF (SEQ ID NO: 6) | WIGVISSYYG DATYNQKF (SEQ ID NO: 7) | WIGLISTYYG DATYTQKF (SEQ ID NO: 8) |
| WIGVISTFYG DANYNQKF (SEQ ID NO: 9) | ARYGDGYNQFDY (SEQ ID NO: 10) | AREDRYVGEFAY (SEQ ID NO: 11) | ALLGAYNYFDY (SEQ ID NO: 12) |
| ARRGNYDSMDY (SEQ ID NO: 13) | ESVDSYGNNFMH (SEQ ID NO: 14) | ESVDSYGNSFIH (SEQ ID NO: 15) | ESVDSYGNSFMH (SEQ ID NO: 16) |
| LLIYRASNLES (SEQ ID NO: 17) | LLVYRASNLES (SEQ ID NO: 18) | QQSYEDPYT (SEQ ID NO: 19) | QQSNEDPRT (SEQ ID NO: 20) |
| QQSYEDPPT (SEQ ID NO: 21) | RLIYRASNLES (SEQ ID NO: 38) | WMGVISTYYG DASYNQKF (SEQ ID NO: 39) | WIGVISTYYG DASYNQKFKG (SEQ ID NO: 87) |
| WLGVIWSGGN TDYNAAFIS (SEQ ID NO: 88) | WIGVISSYYG DATYNQKFKG (SEQ ID NO: 89) | WIGLISTYYG DATYTQKFKG (SEQ ID NO: 90) | WIGVISTFYG DANYNQKFKG (SEQ ID NO: 91) |
| RVSESVDSYG NNFMH (SEQ ID NO: 92) | RASESVDSYG NSFIH (SEQ ID NO: 93) | RASESVDSYG NSFMH (SEQ ID NO: 94) | WMGVISTYYG DASYNQKFKG (SEQ ID NO: 95) |
| VISTYYGDAS YNQKFKG (SEQ ID NO: 96) | VIWSGGNTDY NAAFIS (SEQ ID NO: 97) | VISSYYGDAT YNQKFKG (SEQ ID NO: 98) | LISTYYGDAT YTQKFKG (SEQ ID NO: 99) |
| VISTFYGDAN YNQKFKG (SEQ ID NO: 100) | VISTYYGDAS YNQKFKG (SEQ ID NO: 101) | RASNLES (SEQ ID NO: 102) | |

In some embodiments, the anti-TROP2 antibody (or antigen binding fragment thereof) comprises a heavy chain variable domain (VH) comprising an amino acid sequence that has at least about 95%, 96%, 97%, 98%, 99%, or 100% sequence identity to an amino acid sequence set forth in any one of SEQ ID NOs: 22-26 and 40-45 and/or a light chain variable domain (VL) comprising an amino acid sequence that has at least about 95%, 96%, 97%, 98%, 99%, or 100% sequence identity to an amino acid sequence set forth in any one of SEQ ID NOs: 27-31 and 46-51. The amino acid sequences of SEQ ID NOs: 22-31 and 40-51 are provided in Table 2 below:

TABLE 2

(SEQ ID NO: 22)
QVQLQQSGAELVRPGVSVKISCKGSGYTFTDYSINWVKQSHAKSLEWIGV
ISTYYGDASYNQKFKGKATMTVDKSSSTAYMELARLTSEDSAIYYCARYG
DGYNQFDYWGQGTTLTVSS (SEQ ID NO: 23)
EVQLEQSGPGLVQPSQSLSITCTVSGFSLTRYGVHWVRQSPGRSLEWLGV
IWSGGNTDYNAAFISRLTITKDNSKSQVFFKMNSLQPNDTGVYYCAREDR
YVGEFAYWGQGTLVTVSA (SEQ ID NO: 24)
QVQLQQSGAELVRPGVSVKISCKGSGYTFTDYSIHWVKQSHAKSLEWIGV
ISSYYGDATYNQKFKGKATMTVDKSSSTAYMELARLTSEDSAIYYCALLG
AYNYFDYWGQGTTLTVSS (SEQ ID NO: 25)
QVQLQQSGAELVRPGVSVKISCKGSGYTFTDYSIHWVKQSHAKSLEWIGL
ISTYYGDATYTQKFKGKATMTVDKSSSTAYMELARLTSEDSAIYYCALLG
AYNYFDYWGQGTTLTVSS (SEQ ID NO: 26)
QVQLQQSGAELVRPGVSVKISCKGSGYTFTDYGMNWVKQSHAKSLEWIGV
ISTFYGDANYNQKFKGKATMTVDKSSSTAYMELARLTSEDSAIYYCARRG
NYDSMDYWGQGTSVTVSS (SEQ ID NO: 40)
QVQLVQSGAEVKKPGASVKVSCKASGYTFTDYSINWVRQAPGQGLEWMGV
ISTYYGDASYNQKFKGRVTMTTDTSTSTAYMELRSLRSDDTAVYYCARYG
DGYNQFDYWGQGTMVTVSS (SEQ ID NO: 41)
QVQLVQSGAEVKKPGASVKVSCKASGYTFTDYSINWVRQAPGQGLEWMGV
ISTYYGDASYNQKFKGRVTMTRDTSTSTVYMELSSLRSEDTAVYYCARYG
DGYNQFDYWGQGTLVTVSS (SEQ ID NO: 42)
QVQLVQSGAEVKKPGASVKVSCKASGYTFTDYSINWVRQAPGQRLEWMGV
ISTYYGDASYNQKFKGRVTITRDTSASTAYMELSSLRSEDTAVYYCARYG
DGYNQFDYWGQGTLVTVSS (SEQ ID NO: 43)
QVQLVQSGAEVKKPGSSVKVSCKASGYTFTDYSINWVRQAPGQGLEWMGV
ISTYYGDASYNQKFKGRVTITADESTSTAYMELSSLRSEDTAVYYCARYG
DGYNQFDYWGQGTLVTVSS (SEQ ID NO: 44)
EVQLVQSGAEVKKPGESLKISCKGSGYTFTDYSINWVRQMPGKGLEWMGV
ISTYYGDASYNQKFKGQVTISADKSISTAYLQWSSLKASDTAMYYCARYG
DGYNQFDYWGQGTLVTVSS (SEQ ID NO: 45)
QVQLQQSGAELVRPGVSVKISCKGSGYTFTDYSINWVKQSHAKSLEWIGV
ISTYYGDASYNQKFKGKATMTVDKSSSTAYMELARLTSEDSAIYYCARYG
DGYNQFDYWGQGTTLTVSS (SEQ ID NO: 27)
DIVLTQSPASLAVSLGQRATISCRVSESVDSYGNNFMHWYQQKPGQPPKL
LIYRASNLESGVPARFSGSGSGTDFTLTINPMEADDVATYYCQQSYEDPY
TFGGGTKLEIK (SEQ ID NO: 28)
DIVLTQSTASLAVSLGQRATISCRASESVDSYGNSFIHWYQQKPGQPPKL
LIYRASNLESGIPARFSGSGSRTDFTLTINPVEADDVATYYCQQSNEDPR
TFGGGTKLEIK

TABLE 2-continued (SEQ ID NO: 29)
DIVLTQSPASLAVSLGQRATISCRASESVDSYGNSFMHWYQQKPGQPPKL
LVYRASNLESGIPARFSGSGSRTDFTLTINPVEADDVATYYCQQSYEDPP
TFGGGTKLEIK (SEQ ID NO: 30)
DIVLTQSPASLAVSLGQRATISCRASESVDSYGNSFMHWYQQKPGQPPKL
LVYRASNLESGIPARFSGSGSRTDFTLTINPVEADDIATYYCQQSYEDPP
TFGGGTKLEIK (SEQ ID NO: 31)
DIVLTQSPVFLAVSLGQRATISCRASESVDSYGNSFMHWYQQKPGQPPKL
LIYRASNLESGIPARFSGSGSRTDFTLTINPVEADDVETYYCQQSYEDPP
TFGGGTKLEIE (SEQ ID NO: 46)
DIVMTQSPDSLAVSLGERATINCRVSESVDSYGNNFMHWYQQKPGQPPKL
LIYRASNLESGVPDRFSGSGSGTDFTLTISSLQAEDVAVYYCQQSYEDPY
TFGQGTKLEIK (SEQ ID NO: 47)
DVVMTQSPLSLPVTLGQPASISCRVSESVDSYGNNFMHWFQQRPGQSPRR
LIYRASNLESGVPDRFSGSGSGTDFTLKISRVEAEDVGVYYCQQSYEDPY
TFGGGTKVEIK (SEQ ID NO: 48)
DIVMTQSPLSLPVTPGEPASISCRVSESVDSYGNNFMHWYLQKPGQSPQL
LIYRASNLESGVPDRFSGSGSGTDFTLKISRVEAEDVGVYYCQQSYEDPY
TFGGGTKVEIK (SEQ ID NO: 49)
EIVLTQSPATLSLSPGERATLSCRVSESVDSYGNNFMHWYQQKPGQAPRL
LIYRASNLESGIPARFSGSGSGTDFTLTISSLEPEDFAVYYCQQSYEDPY
TFGGGTKVEIK (SEQ ID NO: 50)
DIQMTQSPSSLSASVGDRVTITCRVSESVDSYGNNFMHWYQQKPGKAPKL
LIYRASNLESGVPSRFSGSGSGTDFTFTISSLQPEDIATYYCQQSYEDPY
TFGGGTKLEIK (SEQ ID NO: 51)
DIVLTQSPASLAVSLGQRATISCRVSESVDSYGNNFMHWYQQKPGQPPKL
LIYRASNLESGVPARFSGSGSGTDFTLTINPMEADDVATYYCQQSYEDPY
TFGGGTKLEIK In some embodiments, the anti-TROP2 antibody (or antigen binding fragment thereof) comprises one, two, or three CDRs of a heavy chain variable domain (VH) comprising an amino acid sequence that has at least about 95%, 96%, 97%, 98%, 99%, or 100% sequence identity to an amino acid sequence set forth in any one of SEQ ID NOs: 22-26 and 40-45 or one, two, or three CDRs of a light chain variable domain (VL) comprising an amino acid sequence that has at least about 95%, 96%, 97%, 98%, 99%, or 100% sequence identity to an amino acid sequence set forth in any one of SEQ ID NOs: 27-3 land 46-51.

In some embodiments, the anti-TROP2 antibody is a full length antibody that comprises a heavy chain comprising the amino acid sequence of any one of SEQ ID NOs: 52-57 and a light chain comprising the amino acid sequence of any one of 58-63. In some embodiments, the heavy chain comprises SEQ ID NO: 57 and the light chain comprises SEQ ID NO: 63. In some embodiments, the heavy chain comprises SEQ ID NO: 52 and the light chain comprises SEQ ID NO: 58. In some embodiments, the heavy chain comprises SEQ ID NO: 52 and the light chain comprises SEQ ID NO: 59. In some embodiments, the heavy chain comprises SEQ ID NO: 52 and the light chain comprises SEQ ID NO: 60. In some embodiments, the heavy chain comprises SEQ ID NO: 52 and the light chain comprises SEQ ID NO: 61. In some embodiments, the heavy chain comprises SEQ ID NO: 52 and the light chain comprises SEQ ID NO: 62. In some embodiments, the heavy chain comprises SEQ ID NO: 53 and the light chain comprises SEQ ID NO: 58. In some embodiments, the heavy chain comprises SEQ ID NO: 53 and the light chain comprises SEQ ID NO: 59. In some embodiments, the heavy chain comprises SEQ ID NO: 53 and the light chain comprises SEQ ID NO: 60. In some embodiments, the heavy chain comprises SEQ ID NO: 53 and the light chain comprises SEQ ID NO: 61. In some embodiments, the heavy chain comprises SEQ ID NO: 53 and the light chain comprises SEQ ID NO: 62. In some embodiments, the heavy chain comprises SEQ ID NO: 54 and the light chain comprises SEQ ID NO: 58. In some embodiments, the heavy chain comprises SEQ ID NO: 54 and the light chain comprises SEQ ID NO: 59. In some embodiments, the heavy chain comprises SEQ ID NO: 54 and the light chain comprises SEQ ID NO: 60. In some embodiments, the heavy chain comprises SEQ ID NO: 54 and the light chain comprises SEQ ID NO: 61. In some embodiments, the heavy chain comprises SEQ ID NO: 54 and the light chain comprises SEQ ID NO: 62. In some embodiments, the heavy chain comprises SEQ ID NO: 55 and the light chain comprises SEQ ID NO: 58. In some embodiments, the heavy chain comprises SEQ ID NO: 55 and the light chain comprises SEQ ID NO: 59 In some embodiments, the heavy chain comprises SEQ ID NO: 55 and the light chain comprises SEQ ID NO: 60. In some embodiments, the heavy chain comprises SEQ ID NO: 55 and the light chain comprises SEQ ID NO: 61. In some embodiments, the heavy chain comprises SEQ ID NO: 55 and the light chain comprises SEQ ID NO: 62. In some embodiments, the heavy chain comprises SEQ ID NO: 56 and the light chain comprises SEQ ID NO: 58. In some embodiments, the heavy chain comprises SEQ ID NO: 56 and the light chain comprises SEQ ID NO: 59. In some embodiments, the heavy chain comprises SEQ ID NO: 56 and the light chain comprises SEQ ID NO: 60. In some embodiments, the heavy chain comprises SEQ ID NO: 56 and the light chain comprises SEQ ID NO: 61. In some embodiments, the heavy chain comprises SEQ ID NO: 56 and the light chain comprises SEQ ID NO: 62. The amino acid sequences of SEQ ID NOs: 52-63 are provided in Table 4 below.

TABLE 4

(SEQ ID NO: 52)
QVQLVQSGAEVKKPGASVKVSCKASGYTFTDYSINWVRQAPGQGLEWMGV
ISTYYGDASYNQKFKGRVTMTTDTSTSTAYMELRSLRSDDTAVYYCARYG
DGYNQFDYWGQGTMVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 53)
QVQLVQSGAEVKKPGASVKVSCKASGYTFTDYSINWVRQAPGQGLEWMGV
ISTYYGDASYNQKFKGRVTMTRDTSTSTVYMELSSLRSEDTAVYYCARYG
DGYNQFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 54)
QVQLVQSGAEVKKPGASVKVSCKASGYTFTDYSINWVRQAPGQRLEWMGV
ISTYYGDASYNQKFKGRVTITRDTSASTAYMELSSLRSEDTAVYYCARYG
DGYNQFDYWGQGTLVTVSSASTKGPSVFPLAPSSKSTSGGTAALGCLVKD

TABLE 4-continued

YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 55)
QVQLVQSGAEVKKPGSSVKVSCKASGYTFTDYSINWVRQAPGQGLEWMGV
ISTYYGDASYNQKFKGRVTITADESTSTAYMELSSLRSEDTAVYYCARYG
DGYNQFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 56)
EVQLVQSGAEVKKPGESLKISCKGSGYTFTDYSINWVRQMPGKGLEWMGV
ISTYYGDASYNQKFKGQVTISADKSISTAYLQWSSLKASDTAMYYCARYG
DGYNQFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 57)
QVQLQQSGAELVRPGVSVKISCKGSGYTFTDYSINWVKQSHAKSLEWIGV
ISTYYGDASYNQKFKGKATMTVDKSSSTAYMELARLTSEDSAIYYCARYG
DGYNQFDYWGQGTTLTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 58)
DIVMTQSPDSLAVSLGERATINCRVSESVDSYGNNFMHWYQQKPGQPPKL
LIYRASNLESGVPDRFSGSGSGTDFTLTISSLQAEDVAVYYCQQSYEDPY
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (SEQ ID NO: 59)
DVVMTQSPLSLPVTLGQPASISCRVSESVDSYGNNFMHWFQQRPGQSPRR
LIYRASNLESGVPDRFSGSGSGTDFTLKISRVEAEDVGVYYCQQSYEDPY
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (SEQ ID NO: 60)
DIVMTQSPLSLPVTPGEPASISCRVSESVDSYGNNFMHWYLQKPGQSPQL
LIYRASNLESGVPDRFSGSGSGTDFTLKISRVEAEDVGVYYCQQSYEDPY
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (SEQ ID NO: 61)
EIVLTQSPATLSLSPGERATLSCRVSESVDSYGNNFMHWYQQKPGQAPRL
LIYRASNLESGIPARFSGSGSGTDFTLTISSLEPEDFAVYYCQQSYEDPY
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (SEQ ID NO: 62)
DIQMTQSPSSLSASVGDRVTITCRVSESVDSYGNNFMHWYQQKPGKAPKL
LIYRASNLESGVPSRFSGSGSGTDFTFTISSLQPEDIATYYCQQSYEDPY
TFGGGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC (SEQ ID NO: 63)
DIVLTQSPASLAVSLGQRATISCRVSESVDSYGNNFMHWYQQKPGQPPKL
LIYRASNLESGVPARFSGSGSGTDFTLTINPMEADDVATYYCQQSYEDPY

TABLE 4-continued

| |
|---|
| TFGGGTKLEIKRTVAAPSVFIFPPSDEQLKSGTASVVCLLNNFYPREAKV<br>QWKVDNALQSGNSQESVTEQDSKDSTYSLSSTLTLSKADYEKHKVYACEV<br>THQGLSSPVTKSFNRGEC |

In certain embodiments, provided is an anti-TROP2 antibody (or antigen-binding fragment thereof) that specifically binds anti-TROP2 and competes for binding to anti-TROP2 with a second anti-TROP2 antibody that comprises a heavy chain comprising a VH set forth in any one of SEQ ID NO: 22-26 and 40-45 and a light chain comprising a VL set forth in any one of SEQ ID NOs: 27-31 and 46-51.

In certain embodiments, provided is an anti-TROP2 antibody (or antigen-binding fragment thereof) that specifically binds to the same epitope of TROP2 as a second anti-TROP2 antibody that antibody that comprises a heavy chain comprising a $V_H$ set forth in any one of SEQ ID NO: 22-26 and 40-45 and a light chain comprising a $V_L$ set forth in any one of SEQ ID NOs: 27-31 and 46-51.

In certain embodiments, the anti-TROP2 antibody (or antigen binding fragment thereof) comprises: (i) a CDR-H1 comprising GYTFTDYSIN (SEQ ID NO: 1) or a variant thereof comprising up to about 5 (such as about any of 1, 2, 3, 4, or 5) amino acid substitutions; (ii) a CDR-H2 comprising WIGVISTYYGDASYNQKF (SEQ ID NO: 5), WIGVISTYYGDASYNQKFKG (SEQ ID NO: 87) or VISTYYGDASYNQKFKG (SEQ ID NO: 96), or a variant of any one of SEQ ID NOs: 5, 87, and 96 comprising up to about 5 (such as about any of 1, 2, 3, 4, or 5) amino acid substitutions; (iii) a CDR-H3 comprising ARYGDGYNQFDY (SEQ ID NO: 10) or a variant thereof comprising up to about 5 (such as about any of 1, 2, 3, 4, or 5) amino acid substitutions; (iv) a CDR-L1 comprising ESVDSYGNNFMH (SEQ ID NO: 14) or RVSESVDSYGNNFMH (SEQ ID NO: 92) or a variant of SEQ ID NO: 14 or 92 comprising up to about 5 (such as about any of 1, 2, 3, 4, or 5) amino acid substitutions; (v) a CDR-L2 comprising LLIYRASNLES (SEQ ID NO: 17) or RASNLES (SEQ ID NO: 102) or a variant of SEQ ID NO: 17 or 102 comprising up to about 5 (such as about any of 1, 2, 3, 4, or 5) amino acid substitutions; and (vi) a CDR-L3 comprising QQSYEDPYT (SEQ ID NO: 19) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ARYGDGYNQFDY (SEQ ID NO: 10) and/or a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1), (ii) a CDR-H2 comprising WIGVISTYYGDASYNQKF (SEQ ID NO: 5), WIGVISTYYGDASYNQKFKG (SEQ ID NO: 87), or VISTYYGDASYNQKFKG (SEQ ID NO: 96), (iii) a CDR-H3 comprising ARYGDGYNQFDY (SEQ ID NO: 10); (iv) a CDR-L1 comprising ESVDSYGNNFMH (SEQ ID NO: 14) or RVSESVDSYGNNFMH (SEQ ID NO: 92), (v) a CDR-L2 comprising LLIYRASNLES (SEQ ID NO: 17) or RASNLES (SEQ ID NO: 102), and (vi) a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1), (ii) a CDR-H2 comprising VISTYYGDASYNQKFKG (SEQ ID NO: 96), (iii) a CDR-H3 comprising ARYGDGYNQFDY (SEQ ID NO: 10); (iv) a CDR-L1 comprising RVSESVDSYGNNFMH (SEQ ID NO: 92), (v) a RASNLES (SEQ ID NO: 102), and (vi) a CDR-L3 comprising QQSYEDPYT (SEQ ID NO: 19). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 22 and/or a VL domain comprising an amino acid sequence that has at least about 95%, 96%, 97%, 98%, 99%, or 100% sequence identity to SEQ ID NO: 27. In some embodiments, the anti-TROP2 antibody (or antigen binding fragment thereof) comprises 3 CDRs of a VH domain comprising SEQ ID NO: 22 and/or 3 CDRs of a VL domain comprising SEQ ID NO: 27. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 22 and a VL domain comprising SEQ ID NO: 27

In certain embodiments, the anti-TROP2 antibody (or antigen binding fragment thereof) comprises: (i) a CDR-H1 comprising GFSLTRYGVH (SEQ ID NO: 2) or a variant thereof comprising up to about 5 (such as about any of 1, 2, 3, 4, or 5) amino acid substitutions, (ii) a CDR-H2 comprising WLGVIWSGGNTDYNAAF (SEQ ID NO: 6), WLGVIWSGGNTDYNAAFIS (SEQ ID NO: 88), VIWSGGNTDYNAAFIS (SEQ ID NO: 97) or a variant of any one of SEQ ID NOs: 6, 88, and 97 comprising up to about 5 (such as about any of 1, 2, 3, 4, or 5) amino acid substitutions, (iii) a CDR-H3 comprising AREDRYVGEFAY (SEQ ID NO: 11) or a variant thereof comprising up to about 5 (such as about any of 1, 2, 3, 4, or 5) amino acid substitutions, (iv) a CDR-L1 comprising ESVDSYGNSFIH (SEQ ID NO: 15), RASESVDSYGNSFIH (SEQ ID NO: 93), or a variant of SEQ ID NO: 15 or 93 comprising up to about 5 (such as about any of 1, 2, 3, 4, or 5) amino acid substitutions, (v) a CDR-L2 comprising LLIYRASNLES (SEQ ID NO: 17), RASNLES (SEQ ID NO: 102) or a variant of SEQ ID NO: 17 or 102 comprising up to about 5 (such as about any of 1, 2, 3, 4, or 5) amino acid substitutions, and (vi) a CDR-L3 comprising QQSNEDPRT (SEQ ID NO: 20) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising AREDRYVGEFAY (SEQ ID NO: 11) and/or a CDR-L3 comprising QQSNEDPRT (SEQ ID NO: 20). In certain embodiments, the anti-TROP2 antibody (or antigen binding fragment thereof) comprises: (i) a CDR-H1 comprising GFSLTRYGVH (SEQ ID NO: 2), (ii) a CDR-H2 comprising WLGVIWSGGNTDYNAAF (SEQ ID NO: 6), WLGVIWSGGNTDYNAAFIS (SEQ ID NO: 88), or VIWSGGNTDYNAAFIS (SEQ ID NO: 97) (iii) a CDR-H3 comprising AREDRYVGEFAY (SEQ ID NO: 11); (iv) a CDR-L1 comprising ESVDSYGNSFIH (SEQ ID NO: 15) or RASESVDSYGNSFIH (SEQ ID NO: 93); (v) a CDR-L2 comprising LLIYRASNLES (SEQ ID NO: 17) or RASNLES (SEQ ID NO: 102), and (vi) a CDR-L3 comprising QQSNEDPRT (SEQ ID NO: 20). In certain embodiments, the anti-TROP2 antibody (or antigen binding fragment thereof) comprises: (i) a CDR-H1 comprising GFSLTRYGVH (SEQ ID NO: 2), (ii) a CDR-H2 comprising VIWSGGNTDYNAAFIS (SEQ ID NO: 97) (iii) a CDR-H3 comprising AREDRYVGEFAY (SEQ ID NO: 11); (iv) a CDR-L1 comprising RASESVDSYGNSFIH (SEQ ID NO: 93); (v) a CDR-L2 comprising RASNLES (SEQ ID NO:

102), and (vi) a CDR-L3 comprising QQSNEDPRT (SEQ ID NO: 20). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 23 and/or a VL domain comprising an amino acid sequence that has at least about 95%, 96%, 97%, 98%, 99%, or 100% sequence identity to SEQ ID NO: 28. In some embodiments, the anti-TROP2 antibody (or antigen binding fragment thereof) comprises 3 CDRs of a VH domain comprising SEQ ID NO: 23 and/or 3 CDRs of a VL domain comprising SEQ ID NO: 28. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 23 and a VL domain comprising SEQ ID NO: 28.

In certain embodiments, the anti-TROP2 antibody (or antigen binding fragment thereof) comprises: (i) a CDR-H1 comprising GYTFTDYSIH (SEQ ID NO: 3) or a variant thereof comprising up to about 5 (such as about any of 1, 2, 3, 4, or 5) amino acid substitutions, (ii) a CDR-H2 comprising WIGVISSYYGDATYNQKF (SEQ ID NO: 7), WIGVISSYYGDATYNQKFKG (SEQ ID NO: 89), VISSYYGDATYNQKFKG (SEQ ID NO: 98), or a variant of any one of SEQ ID NOs: 7, 89, and 98 comprising up to about 5 (such as about any of 1, 2, 3, 4, or 5) amino acid substitutions, (iii) a CDR-H3 comprising ALLGAYNYFDY (SEQ ID NO: 12) or a variant thereof comprising up to about 5 (such as about any of 1, 2, 3, 4, or 5) amino acid substitutions, (iv) a CDR-L1 comprising ESVDSYGNSFMH (SEQ ID NO: 16), RASESVDSYGNSFMH (SEQ ID NO: 94) or a variant of SEQ ID NO: 16 or 94 comprising up to about 5 (such as about any of 1, 2, 3, 4, or 5) amino acid substitutions, (v) a CDR-L2 comprising LLVYRASNLES (SEQ ID NO: 18), RASNLES (SEQ ID NO: 102), or a variant of SEQ ID NO: 18 or 102 comprising up to about 5 (such as about any of 1, 2, 3, 4, or 5) amino acid substitutions, and (vi) a CDR-L3 comprising QQSYEDPPT (SEQ ID NO: 21) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ALLGAYNYFDY (SEQ ID NO: 12) and/or a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYSIH (SEQ ID NO: 3); (ii) a CDR-H2 comprising WIGVISSYYGDATYNQKF (SEQ ID NO: 7), WIGVISSYYGDATYNQKFKG (SEQ ID NO: 89), or VISSYYGDATYNQKFKG (SEQ ID NO: 98); (iii) a CDR-H3 comprising ALLGAYNYFDY (SEQ ID NO: 12); (iv) a CDR-L1 comprising ESVDSYGNSFMH (SEQ ID NO: 16) or RASESVDSYGNSFMH (SEQ ID NO: 94); (v) a CDR-L2 comprising LLVYRASNLES (SEQ ID NO: 18) or RASNLES (SEQ ID NO: 102); and (vi) a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYSIH (SEQ ID NO: 3); (ii) a CDR-H2 comprising VISSYYGDATYNQKFKG (SEQ ID NO: 98); (iii) a CDR-H3 comprising ALLGAYNYFDY (SEQ ID NO: 12); (iv) a CDR-L1 comprising RASESVDSYGNSFMH (SEQ ID NO: 94); (v) a CDR-L2 comprising RASNLES (SEQ ID NO: 102); and (vi) a CDR-L3 comprising QQSYEDPPT (SEQ ID NO: 21). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 24 and/or a VL domain comprising an amino acid sequence that has at least about 95%, 96%, 97%, 98%, 99%, or 100% sequence identity to SEQ ID NO: 29. In some embodiments, the anti-TROP2 antibody (or antigen binding fragment thereof) comprises 3 CDRs of a VH domain comprising SEQ ID NO: 24 and/or 3 CDRs of a VL domain comprising SEQ ID NO: 29. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 24 and a VL domain comprising SEQ ID NO: 29.

In certain embodiments, the anti-TROP2 antibody (or antigen binding fragment thereof) comprises: (i) a CDR-H1 comprising GYTFTDYSIH (SEQ ID NO: 3) or a variant thereof comprising up to about 5 (such as about any of 1, 2, 3, 4, or 5) amino acid substitutions, (ii) a CDR-H2 comprising WIGLISTYYGDATYTQKF (SEQ ID NO: 8), WIGLISTYYGDATYTQKFKG (SEQ ID NO: 90), LISTYYGDATYTQKFKG (SEQ ID NO: 99), or a variant of any one of SEQ ID NOs: 8, 90, and 99 comprising up to about 5 (such as about any of 1, 2, 3, 4, or 5) amino acid substitutions, (iii) a CDR-H3 comprising ALLGAYNYFDY (SEQ ID NO: 12) or a variant thereof comprising up to about 5 (such as about any of 1, 2, 3, 4, or 5) amino acid substitutions, (iv) a CDR-L1 comprising ESVDSYGNSFMH (SEQ ID NO: 16), RASESVDSYGNSFMH (SEQ ID NO: 94), or a variant of SEQ ID NO: 16 or 94 comprising up to about 5 (such as about any of 1, 2, 3, 4, or 5) amino acid substitutions, (v) a CDR-L2 comprising LLVYRASNLES (SEQ ID NO: 18), RASNLES (SEQ ID NO: 102), or a variant of SEQ ID NO: 18 or 102 comprising up to about 5 (such as about any of 1, 2, 3, 4, or 5) amino acid substitutions, and (vi) a CDR-L3 comprising QQSYEDPPT (SEQ ID NO: 21) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ALLGAYNYFDY (SEQ ID NO: 12) and/or a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYSIH (SEQ ID NO: 3), (ii) a CDR-H2 comprising WIGLISTYYGDATYTQKF (SEQ ID NO: 8), WIGLISTYYGDATYTQKFKG (SEQ ID NO: 90), or LISTYYGDATYTQKFKG (SEQ ID NO: 99), (iii) a CDR-H3 comprising ALLGAYNYFDY (SEQ ID NO: 12); (iv) a CDR-L1 comprising ESVDSYGNSFMH (SEQ ID NO: 16) or RASESVDSYGNSFMH (SEQ ID NO: 94), (v) a CDR-L2 comprising LLVYRASNLES (SEQ ID NO: 18) or RASNLES (SEQ ID NO: 102), and (vi) a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYSIH (SEQ ID NO: 3), (ii) a CDR-H2 comprising LISTYYGDATYTQKFKG (SEQ ID NO: 99), (iii) a CDR-H3 comprising ALLGAYNYFDY (SEQ ID NO: 12); (iv) a CDR-L1 comprising RASESVDSYGNSFMH (SEQ ID NO: 94), (v) a CDR-L2 comprising RASNLES (SEQ ID NO:

102), and (vi) a CDR-L3 comprising QQSYEDPPT (SEQ ID NO: 21). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 25 and/or a VL domain comprising an amino acid sequence that has at least about 95%, 96%, 97%, 98%, 99%, or 100% sequence identity to SEQ ID NO: 30. In some embodiments, the anti-TROP2 antibody (or antigen binding fragment thereof) comprises 3 CDRs of a VH domain comprising SEQ ID NO: 25 and/or 3 CDRs of a VL domain comprising SEQ ID NO: 30. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 25 and a VL domain comprising SEQ ID NO: 30.

In certain embodiments, the anti-TROP2 antibody (or antigen binding fragment thereof) comprises: (i) a CDR-H1 comprising GYTFTDYGMN (SEQ ID NO: 4) or a variant thereof comprising up to about 5 (such as about any of 1, 2, 3, 4, or 5) amino acid substitutions, (ii) a CDR-H2 comprising WIGVISTFYGDANYNQKF (SEQ ID NO: 9), WIGVISTFYGDANYNQKFKG (SEQ ID NO: 91), VISTFYGDANYNQKFKG (SEQ ID NO: 100) or a variant of any one of SEQ ID NOs: 9, 91, and 100 comprising up to about 5 (such as about any of 1, 2, 3, 4, or 5) amino acid substitutions, (iii) a CDR-H3 comprising ARRGNYDSMDY (SEQ ID NO: 13) or a variant thereof comprising up to about 5 (such as about any of 1, 2, 3, 4, or 5) amino acid substitutions, (iv) a CDR-L1 comprising ESVDSYGNSFMH (SEQ ID NO: 16), RASESVDSYGNSFMH (SEQ ID NO: 94) or a variant of SEQ ID NO: 16 or 94 comprising up to about 5 (such as about any of 1, 2, 3, 4, or 5) amino acid substitutions, (v) a CDR-L2 comprising LLIYRASNLES (SEQ ID NO: 17), RASNLES (SEQ ID NO: 102) or a variant of SEQ ID NO: 17 or 102 comprising up to about 5 (such as about any of 1, 2, 3, 4, or 5) amino acid substitutions, and (vi) a CDR-L3 comprising QQSYEDPPT (SEQ ID NO: 21) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ARRGNYDSMDY (SEQ ID NO: 13) and/or a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYGMN (SEQ ID NO: 4); (ii) a CDR-H2 comprising WIGVISTFYGDANYNQKF (SEQ ID NO: 9), WIGVISTFYGDANYNQKFKG (SEQ ID NO: 91), or VISTFYGDANYNQKFKG (SEQ ID NO: 100); (iii) a CDR-H3 comprising ARRGNYDSMDY (SEQ ID NO: 13); (iv) a CDR-L1 comprising ESVDSYGNSFMH (SEQ ID NO: 16) or RASESVDSYGNSFMH (SEQ ID NO: 94); (v) a CDR-L2 comprising LLIYRASNLES (SEQ ID NO: 17) or RASNLES (SEQ ID NO: 102), and (vi) a CDR-L3 comprising QQSYEDPPT (SEQ ID NO: 21). In certain embodiments, the anti-TROP2 antibody (or antigen binding fragment thereof) comprises: (i) a CDR-H1 comprising GYTFTDYGMN (SEQ ID NO: 4); (ii) a CDR-H2 comprising VISTFYGDANYNQKFKG (SEQ ID NO: 100); (iii) a CDR-H3 comprising ARRGNYDSMDY (SEQ ID NO: 13); (iv) a CDR-L1 comprising RASESVDSYGNSFMH (SEQ ID NO: 94); (v) a CDR-L2 comprising RASNLES (SEQ ID NO: 102), and (vi) a CDR-L3 comprising QQSYEDPPT (SEQ ID NO: 21). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 26 and/or a VL domain comprising an amino acid sequence that has at least about 95%, 96%, 97%, 98%, 99%, or 100% sequence identity to SEQ ID NO: 31. In some embodiments, the anti-TROP2 antibody (or antigen binding fragment thereof) comprises 3 CDRs of a VH domain comprising SEQ ID NO: 26 and/or 3 CDRs of a VL domain comprising SEQ ID NO: 31. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 26 and a VL domain comprising SEQ ID NO: 31.

In certain embodiments, the anti-TROP2 antibody (or antigen binding fragment thereof) comprises: (i) a CDR-H1 comprising GYTFTDYSIN (SEQ ID NO: 1) or a variant thereof comprising up to about 5 (such as about any of 1, 2, 3, 4, or 5) amino acid substitutions, (ii) a CDR-H2 comprising WIGVISTYYGDASYNQKF (SEQ ID NO: 5), WIGVISTYYGDASYNQKFKG (SEQ ID NO: 87), VISTYYGDASYNQKFKG (SEQ ID NO: 96) or a variant of any one of SEQ ID NOs: 5, 87, and 96 comprising up to about 5 (such as about any of 1, 2, 3, 4, or 5) amino acid substitutions, (iii) a CDR-H3 comprising ARYGDGYNQFDY (SEQ ID NO: 10) or a variant thereof comprising up to about 5 (such as about any of 1, 2, 3, 4, or 5) amino acid substitutions, (iv) a CDR-L1 comprising ESVDSYGNNFMH (SEQ ID NO: 14), RVSESVDSYGNNFMH (SEQ ID NO: 92), or a variant of SEQ ID NO: 14 or 92 comprising up to about 5 (such as about any of 1, 2, 3, 4, or 5) amino acid substitutions, (v) a CDR-L2 comprising LLIYRASNLES (SEQ ID NO: 17), RASNLES (SEQ ID NO: 102) or a variant of SEQ ID NO: 17 or 102 comprising up to about 5 (such as about any of 1, 2, 3, 4, or 5) amino acid substitutions, and (vi) a CDR-L3 comprising QQSYEDPYT (SEQ ID NO: 19) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ARYGDGYNQFDY (SEQ ID NO: 10) and/or a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising WIGVISTYYGDASYNQKF (SEQ ID NO: 5), WIGVISTYYGDASYNQKFKG (SEQ ID NO: 87), or VISTYYGDASYNQKFKG (SEQ ID NO: 96); (iii) a CDR-H3 comprising ARYGDGYNQFDY (SEQ ID NO: 10); (iv) a CDR-L1 comprising ESVDSYGNNFMH (SEQ ID NO: 14) or RVSESVDSYGNNFMH (SEQ ID NO: 92); (v) a CDR-L2 comprising LLIYRASNLES (SEQ ID NO: 17) or RASNLES (SEQ ID NO: 102); and (vi) a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising VISTYYGDASYNQKFKG (SEQ ID NO: 96); (iii) a CDR-H3 comprising ARYGDGYNQFDY (SEQ ID NO: 10); (iv) a CDR-L1 comprising RVSESVDSYGNNFMH (SEQ ID NO: 92); (v) a CDR-L2 comprising RASNLES (SEQ ID NO: 102); and (vi) a CDR-L3 comprising QQSYEDPYT (SEQ ID NO: 19). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 45 and/or a VL domain comprising an amino acid sequence that has at least about 95%, 96%, 97%, 98%, 99%, or 100% sequence identity to SEQ ID NO: 51. In some embodiments, the anti-TROP2 antibody (or antigen binding fragment thereof) comprises 3 CDRs of a VH domain comprising SEQ ID NO: 45 and/or 3 CDRs of a VL domain comprising SEQ ID NO: 51. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 45 and a VL domain comprising SEQ ID NO: 51. In some embodiments, the anti-TROP2 antibody comprises a heavy chain comprising the amino acid sequence 57 and/or a light chain comprising the amino acid sequence 63.

In certain embodiments, the anti-TROP2 antibody (or antigen binding fragment thereof) comprises: (i) a CDR-H1 comprising GYTFTDYSIN (SEQ ID NO: 1) or a variant thereof comprising up to about 5 (such as about any of 1, 2, 3, 4, or 5) amino acid substitutions, (ii) a CDR-H2 comprising WMGVISTYYGDASYNQKF (SEQ ID NO: 39), WMGVISTYYGDASYNQKFKG (SEQ ID NO: 95), VISTYYGDASYNQKFKG (SEQ ID NO: 101) or a variant of any one of SEQ ID NOs: 39, 95, and 101 comprising up to about 5 (such as about any of 1, 2, 3, 4, or 5) amino acid substitutions, (iii) a CDR-H3 comprising ARYGDGYNQFDY (SEQ ID NO: 10) or a variant thereof comprising up to about 5 (such as about any of 1, 2, 3, 4, or 5) amino acid substitutions, (iv) a CDR-L1 comprising ESVDSYGNNFMH (SEQ ID NO: 14), RVSESVDSYGNNFMH (SEQ ID NO: 92) or a variant of SEQ ID NO: 14 or 92 comprising up to about 5 (such as about any of 1, 2, 3, 4, or 5) amino acid substitutions, (v) a CDR-L2 comprising LLIYRASNLES (SEQ ID NO: 17), RASNLES (SEQ ID NO: 102) or a variant of SEQ ID NO: 17 or 102 comprising up to about 5 (such as about any of 1, 2, 3, 4, or 5) amino acid substitutions, and (vi) a CDR-L3 comprising QQSYEDPYT (SEQ ID NO: 19) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ARYGDGYNQFDY (SEQ ID NO: 10) and/or a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising WMGVISTYYGDASYNQKF (SEQ ID NO: 39), WMGVISTYYGDASYNQKFKG (SEQ ID NO: 95), or VISTYYGDASYNQKFKG (SEQ ID NO: 101); (iii) a CDR-H3 comprising ARYGDGYNQFDY (SEQ ID NO: 10); (iv) a CDR-L1 comprising ESVDSYGNNFMH (SEQ ID NO: 14) or RVSESVDSYGNNFMH (SEQ ID NO: 92); (v) a CDR-L2 comprising LLIYRASNLES (SEQ ID NO: 17) or RASNLES (SEQ ID NO:102); and (vi) a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising VISTYYGDASYNQKFKG (SEQ ID NO: 101); (iii) a CDR-H3 comprising ARYGDGYNQFDY (SEQ ID NO: 10); (iv) a CDR-L1 comprising RVSESVDSYGNNFMH (SEQ ID NO: 92); (v) a CDR-L2 comprising RASNLES (SEQ ID NO:102); and (vi) a CDR-L3 comprising QQSYEDPYT (SEQ ID NO: 19). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 40 and/or a VL domain comprising an amino acid sequence that has at least about 95%, 96%, 97%, 98%, 99%, or 100% sequence identity to SEQ ID NO: 46. In some embodiments, the anti-TROP2 antibody (or antigen binding fragment thereof) comprises 3 CDRs of a VH domain comprising SEQ ID NO: 40 and/or 3 CDRs of a VL domain comprising SEQ ID NO: 46. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 40 and a VL domain comprising SEQ ID NO: 46. In some embodiments, the anti-TROP2 antibody comprises a heavy chain comprising the amino acid sequence of SEQ ID NO: 52 and/or a light chain comprising the amino acid sequence of SEQ ID NO: 58. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 40 and/or a VL domain comprising an amino acid sequence that has at least about 95%, 96%, 97%, 98%, 99%, or 100% sequence identity to SEQ ID NO: 48. In some embodiments, the anti-TROP2 antibody (or antigen binding fragment thereof) comprises 3 CDRs of a VH domain comprising SEQ ID NO: 40 and/or 3 CDRs of a VL domain comprising SEQ ID NO: 48. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 40 and a VL domain comprising SEQ ID NO: 48. In some embodiments, the anti-TROP2 antibody comprises a heavy chain comprising the amino acid sequence of SEQ ID NO: 52 and/or a light chain comprising the amino acid sequence of SEQ ID NO: 60. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 40 and/or a VL domain comprising an amino acid sequence that has at least about 95%, 96%, 97%, 98%, 99%, or 100% sequence identity to SEQ ID NO: 49. In some embodiments, the anti-TROP2 antibody (or antigen binding fragment thereof) comprises 3 CDRs of a VH domain comprising SEQ ID NO: 40 and/or 3 CDRs of a VL domain comprising SEQ ID NO: 49. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 40 and a VL domain comprising SEQ ID NO: 49. In some embodiments, the anti-TROP2 antibody comprises a heavy chain comprising the amino acid sequence of SEQ ID NO: 52 and/or a light chain comprising the amino acid sequence of SEQ ID NO: 61. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 40 and/or a VL domain comprising an amino acid sequence that has at least about 95%, 96%, 97%, 98%, 99%, or 100% sequence identity to SEQ ID NO: 50. In some embodiments, the anti-TROP2 antibody (or antigen binding fragment thereof) comprises 3 CDRs of a VH domain comprising SEQ ID NO: 40 and/or 3 CDRs of a VL domain comprising SEQ ID NO: 50. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 40 and a VL domain comprising SEQ ID NO: 50. In some embodiments, the anti-TROP2 antibody comprises a heavy chain comprising the amino acid sequence of SEQ ID NO: 52 and/or a light chain comprising the amino acid sequence of SEQ ID NO: 62. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 41 and/or a VL domain comprising an amino acid sequence that has at least about 95%, 96%, 97%, 98%, 99%, or 100% sequence identity to SEQ ID NO: 46. In some embodiments, the anti-TROP2 antibody (or antigen binding fragment thereof) comprises 3 CDRs of a VH domain comprising SEQ ID NO: 41 and/or 3 CDRs of a VL domain comprising SEQ ID NO: 46. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 41 and a VL domain comprising SEQ ID NO: 46. In some embodiments, the anti-TROP2 antibody comprises a heavy chain comprising the amino acid sequence of SEQ ID NO: 53 and/or a light chain comprising the amino acid sequence of SEQ ID NO: 58. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 41 and/or a VL domain comprising an amino acid sequence that has at least about 95%, 96%, 97%, 98%, 99%, or 100% sequence identity to SEQ ID NO: 48. In some embodiments, the anti-TROP2 antibody (or antigen binding fragment thereof) comprises 3 CDRs of a VH domain comprising SEQ ID NO: 41 and/or 3 CDRs of a VL domain comprising SEQ ID NO: 48. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 41 and a VL domain comprising SEQ ID NO: 48. In some embodiments, the anti-TROP2 antibody comprises a heavy chain comprising the amino acid sequence of SEQ ID NO: 53 and/or a light chain comprising the amino acid sequence of SEQ ID NO: 60. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 41 and/or a VL domain comprising an amino acid sequence that has at least about 95%, 96%, 97%, 98%, 99%, or 100% sequence identity to SEQ ID NO: 49. In some embodiments, the anti-TROP2 antibody (or antigen binding fragment thereof) comprises 3 CDRs of a VH domain comprising SEQ ID NO: 41 and/or 3 CDRs of a VL domain comprising SEQ ID NO: 49. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 41 and a VL domain comprising SEQ ID NO: 49. In some embodiments, the anti-TROP2 antibody comprises a heavy chain comprising the amino acid sequence of SEQ ID NO: 53 and/or a light chain comprising the amino acid sequence of SEQ ID NO: 61. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 41 and/or a VL domain comprising an amino acid sequence that has at least about 95%, 96%, 97%, 98%, 99%, or 100% sequence identity to SEQ ID NO: 50. In some embodiments, the anti-TROP2 antibody (or antigen binding fragment thereof) comprises 3 CDRs of a VH domain comprising SEQ ID NO: 41 and/or 3 CDRs of a VL domain comprising SEQ ID NO: 50. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 41 and a VL domain comprising SEQ ID NO: 50. In some embodiments, the anti-TROP2 antibody comprises a heavy chain comprising the amino acid sequence of SEQ ID NO: 53 and/or a light chain comprising the amino acid sequence of SEQ ID NO: 62. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 42 and/or a VL domain comprising an amino acid sequence that has at least about 95%, 96%, 97%, 98%, 99%, or 100% sequence identity to SEQ ID NO: 46. In some embodiments, the anti-TROP2 antibody (or antigen binding fragment thereof) comprise 3 CDRs s of a VH domain comprising SEQ ID NO: 42 and/or 3 CDRs of a VL domain comprising SEQ ID NO: 46. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 42 and a VL domain comprising SEQ ID NO: 46. In some embodiments, the anti-TROP2 antibody comprises a heavy chain comprising the amino acid sequence of SEQ ID NO: 54 and/or a light chain comprising the amino acid sequence of SEQ ID NO: 58. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 42 and/or a VL domain comprising an amino acid sequence that has at least about 95%, 96%, 97%, 98%, 99%, or 100% sequence identity to SEQ ID NO: 48. In some embodiments, the anti-TROP2 antibody (or antigen binding fragment thereof) comprises 3 CDRs of a VH domain comprising SEQ ID NO: 42 and/or 3 CDRs of a VL domain comprising SEQ ID NO: 48. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 42 and a VL domain comprising SEQ ID NO: 48. In some embodiments, the anti-TROP2 antibody comprises a heavy chain comprising the amino acid sequence of SEQ ID NO: 54 and/or a light chain comprising the amino acid sequence of SEQ ID NO: 60. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 42 and/or a VL domain comprising an amino acid sequence that has at least about 95%, 96%, 97%, 98%, 99%, or 100% sequence identity to SEQ ID NO: 49. In some embodiments, the anti-TROP2 antibody (or antigen binding fragment thereof) comprises 3 CDRs of a VH domain comprising SEQ ID NO: 42 and/or 3 CDRs of a VL domain comprising SEQ ID NO: 49. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 42 and a VL domain comprising SEQ ID NO: 49. In some embodiments, the anti-TROP2 antibody comprises a heavy chain comprising the amino acid sequence of SEQ ID NO: 54 and/or a light chain comprising the amino acid sequence of SEQ ID NO: 61. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 42 and/or a VL domain comprising an amino acid sequence that has at least about 95%, 96%, 97%, 98%, 99%, or 100% sequence identity to SEQ ID NO: 50. In some embodiments, the anti-TROP2 antibody (or antigen binding fragment thereof) comprises 3 CDRs of a VH domain comprising SEQ ID NO: 42 and/or 3 CDRs of a VL domain comprising SEQ ID NO: 50. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 42 and a VL domain comprising SEQ ID NO: 50. In some embodiments, the anti-TROP2 antibody comprises a heavy chain comprising the amino acid sequence of SEQ ID NO: 54 and/or a light chain comprising the amino acid sequence of SEQ ID NO: 62. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 43 and/or a VL domain comprising an amino acid sequence that has at least about 95%, 96%, 97%, 98%, 99%, or 100% sequence identity to SEQ ID NO: 46. In some embodiments, the anti-TROP2 antibody (or antigen binding fragment thereof) comprises 3 CDRs of a VH domain comprising SEQ ID NO: 43 and/or 3 CDRs of a VL domain comprising SEQ ID NO: 46. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 43 and a VL domain comprising SEQ ID NO: 46. In some embodiments, the anti-TROP2 antibody comprises a heavy chain comprising the amino acid sequence of SEQ ID NO: 55 and/or a light chain comprising the amino acid sequence of SEQ ID NO: 58. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 43 and/or a VL domain comprising an amino acid sequence that has at least about 95%, 96%, 97%, 98%, 99%, or 100% sequence identity to SEQ ID NO: 48. In some embodiments, the anti-TROP2 antibody (or antigen binding fragment thereof) comprises 3 CDRs of a VH domain comprising SEQ ID NO: 43 and/or 3 CDRs of a VL domain comprising SEQ ID NO: 48. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 43 and a VL domain comprising SEQ ID NO: 48. In some embodiments, the anti-TROP2 antibody comprises a heavy chain comprising the amino acid sequence of SEQ ID NO: 55 and/or a light chain comprising the amino acid sequence of SEQ ID NO: 60. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 43 and/or a VL domain comprising an amino acid sequence that has at least about 95%, 96%, 97%, 98%, 99%, or 100% sequence identity to SEQ ID NO: 49. In some embodiments, the anti-TROP2 antibody (or antigen binding fragment thereof) comprises 3 CDRs of a VH domain comprising SEQ ID NO: 43 and/or 3 CDRs of a VL domain comprising SEQ ID NO: 49. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 43 and a VL domain comprising SEQ ID NO: 49. In some embodiments, the anti-TROP2 antibody comprises a heavy chain comprising the amino acid sequence of SEQ ID NO: 55 and/or a light chain comprising the amino acid sequence of SEQ ID NO: 61. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 43 and/or a VL domain comprising an amino acid sequence that has at least about 95%, 96%, 97%, 98%, 99%, or 100% sequence identity to SEQ ID NO: 50. In some embodiments, the anti-TROP2 antibody (or antigen binding fragment thereof) comprises 3 CDRs of a VH domain comprising SEQ ID NO: 43 and/or 3 CDRs of a VL domain comprising SEQ ID NO: 50. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 43 and a VL domain comprising SEQ ID NO: 50. In some embodiments, the anti-TROP2 antibody comprises a heavy chain comprising the amino acid sequence of SEQ ID NO: 55 and/or a light chain comprising the amino acid sequence of SEQ ID NO: 62. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 44 and/or a VL domain comprising an amino acid sequence that has at least about 95%, 96%, 97%, 98%, 99%, or 100% sequence identity to SEQ ID NO: 46. In some embodiments, the anti-TROP2 antibody (or antigen binding fragment thereof) comprises 3 CDRs of a VH domain comprising SEQ ID NO: 44 and/or 3 CDRs of a VL domain comprising SEQ ID NO: 46. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 44 and a VL domain comprising SEQ ID NO: 46. In some embodiments, the anti-TROP2 antibody comprises a heavy chain comprising the amino acid sequence of SEQ ID NO: 56 and/or a light chain comprising the amino acid sequence of SEQ ID NO: 58. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 44 and/or a VL domain comprising an amino acid sequence that has at least about 95%, 96%, 97%, 98%, 99%, or 100% sequence identity to SEQ ID NO: 48. In some embodiments, the anti-TROP2 antibody (or antigen binding fragment thereof) comprises 3 CDRs of a VH domain comprising SEQ ID NO: 44 and/or 3 CDRs of a VL domain comprising SEQ ID NO: 48. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 44 and a VL domain comprising SEQ ID NO: 48. In some embodiments, the anti-TROP2 antibody comprises a heavy chain comprising the amino acid sequence of SEQ ID NO: 56 and/or a light chain comprising the amino acid sequence of SEQ ID NO: 60. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 44 and/or a VL domain comprising an amino acid sequence that has at least about 95%, 96%, 97%, 98%, 99%, or 100% sequence identity to SEQ ID NO: 49. In some embodiments, the anti-TROP2 antibody (or antigen binding fragment thereof) comprises 3 CDRs of a VH domain comprising SEQ ID NO: 44 and/or 3 CDRs of a VL domain comprising SEQ ID NO: 49. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 44 and a VL domain comprising SEQ ID NO: 49. In some embodiments, the anti-TROP2 antibody comprises a heavy chain comprising the amino acid sequence of SEQ ID NO: 56 and/or a light chain comprising the amino acid sequence of SEQ ID NO: 61. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 44 and/or a VL domain comprising an amino acid sequence that has at least about 95%, 96%, 97%, 98%, 99%, or 100% sequence identity to SEQ ID NO: 50. In some embodiments, the anti-TROP2 antibody (or antigen binding fragment thereof) comprises 3 CDRs of a VH domain comprising SEQ ID NO: 44 and/or 3 CDRs of a VL domain comprising SEQ ID NO: 50. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 44 and a VL domain comprising SEQ ID NO: 50. In some embodiments, the anti-TROP2 antibody comprises a heavy chain comprising the amino acid sequence of SEQ ID NO: 56 and/or a light chain comprising the amino acid sequence of SEQ ID NO: 62.

In certain embodiments, the anti-TROP2 antibody (or antigen binding fragment thereof) comprises: (i) a CDR-H1 comprising GYTFTDYSIN (SEQ ID NO: 1) or a variant thereof comprising up to about 5 (such as about any of 1, 2, 3, 4, or 5) amino acid substitutions, (ii) a CDR-H2 comprising WMGVISTYYGDASYNQKF (SEQ ID NO: 39), WMGVISTYYGDASYNQKFKG (SEQ ID NO: 95), VISTYYGDASYNQKFKG (SEQ ID NO: 101) or a variant of any one of SEQ ID NOs: 39, 95, and 101 comprising up to about 5 (such as about any of 1, 2, 3, 4, or 5) amino acid substitutions, (iii) a CDR-H3 comprising ARYGDGYNQFDY (SEQ ID NO: 10) or a variant thereof comprising up to about 5 (such as about any of 1, 2, 3, 4, or 5) amino acid substitutions, (iv) a CDR-L1 comprising ESVDSYGNNFMH (SEQ ID NO: 14), RVSESVDSYGNNFMH (SEQ ID NO: 92) or a variant of SEQ ID NO: 14 or 92 comprising up to about 5 (such as about any of 1, 2, 3, 4, or 5) amino acid substitutions, (v) a CDR-L2 comprising RLIYRASNLES (SEQ ID NO: 38), RASNLES (SEQ ID NO: 102) or a variant of SEQ ID NO: 38 or 102 comprising up to about 5 (such as about any of 1, 2, 3, 4, or 5) amino acid substitutions, and (vi) a CDR-L3 comprising QQSYEDPYT (SEQ ID NO: 19) or a variant thereof comprising up to about 5 (such as about any of 1, 2, 3, 4, or 5) amino acid substitutions. In certain embodiments, the anti-TROP2 antibody (or antigen binding fragment thereof) comprises a CDR-H3 comprising ARYGDGYNQFDY (SEQ ID NO: 10) and/or a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising WMGVISTYYGDASYNQKF (SEQ ID NO: 39), WMGVISTYYGDASYNQKFKG (SEQ ID NO: 95), or VISTYYGDASYNQKFKG (SEQ ID NO: 101); (iii) a CDR-H3 comprising ARYGDGYNQFDY (SEQ ID NO: 10); (iv) a CDR-L1 comprising ESVDSYGNNFMH (SEQ ID NO: 14) or RVSESVDSYGNNFMH (SEQ ID NO: 92); (v) a CDR-L2 comprising RLIYRASNLES (SEQ ID NO: 38) or RASNLES (SEQ ID NO: 102) and (vi) a CDR-L3 comprising QQSYEDPYT (SEQ ID NO: 19). In certain embodiments, the anti-TROP2 antibody (or antigen binding fragment thereof) comprises: (i) a CDR-H1 comprising GYTFTDYSIN (SEQ ID NO: 1); (ii) a CDR-H2 comprising VISTYYGDASYNQKFKG (SEQ ID NO: 101); (iii) a CDR-H3 comprising ARYGDGYNQFDY (SEQ ID NO: 10); (iv) a CDR-L1 comprising RVSESVDSYGNNFMH (SEQ ID NO: 92); (v) a CDR-L2 comprising RASNLES (SEQ ID NO: 102) and (vi) a CDR-L3 comprising QQSYEDPYT (SEQ ID NO: 19). In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 40 and/or a VL domain comprising an amino acid sequence that has at least about 95%, 96%, 97%, 98%, 99%, or 100% sequence identity to SEQ ID NO: 47. In some embodiments, the anti-TROP2 antibody (or antigen binding fragment thereof) comprises 3 CDRs of a VH domain comprising SEQ ID NO: 40 and/or 3 CDRs of a VL domain comprising SEQ ID NO: 47. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 40 and a VL domain comprising SEQ ID NO: 47. In some embodiments, the anti-TROP2 antibody comprises a heavy chain comprising the amino acid sequence of SEQ ID NO: 52 and/or a light chain comprising the amino acid sequence of SEQ ID NO: 59. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 41 and/or a VL domain comprising an amino acid sequence that has at least about 95%, 96%, 97%, 98%, 99%, or 100% sequence identity to SEQ ID NO: 47. In some embodiments, the anti-TROP2 antibody (or antigen binding fragment thereof) comprises 3 CDRs of a VH domain comprising SEQ ID NO: 41 and/or 3 CDRs of a VL domain comprising SEQ ID NO: 47. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 41 and a VL domain comprising SEQ ID NO: 47. In some embodiments, the anti-TROP2 antibody comprises a heavy chain comprising the amino acid sequence of SEQ ID NO: 53 and/or a light chain comprising the amino acid sequence of SEQ ID NO: 59. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 42 and/or a VL domain comprising an amino acid sequence that has at least about 95%, 96%, 97%, 98%, 99%, or 100% sequence identity to SEQ ID NO: 47. In some embodiments, the anti-TROP2 antibody (or antigen binding fragment thereof) comprises 3 CDRs of a VH domain comprising SEQ ID NO: 42 and/or 3 CDRs of a VL domain comprising SEQ ID NO: 47. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 42 and a VL domain comprising SEQ ID NO: 47. In some embodiments, the anti-TROP2 antibody comprises a heavy chain comprising the amino acid sequence of SEQ ID NO: 54 and/or a light chain comprising the amino acid sequence of SEQ ID NO: 59. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 43 and/or a VL domain comprising an amino acid sequence that has at least about 95%, 96%, 97%, 98%, 99%, or 100% sequence identity to SEQ ID NO: 47. In some embodiments, the anti-TROP2 antibody (or antigen binding fragment thereof) comprises 3 CDRs of a VH domain comprising SEQ ID NO: 43 and/or 3 CDRs of a VL domain comprising SEQ ID NO: 47. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 43 and a VL domain comprising SEQ ID NO: 47. In some embodiments, the anti-TROP2 antibody comprises a heavy chain comprising the amino acid sequence of SEQ ID NO: 55 and/or a light chain comprising the amino acid sequence of SEQ ID NO: 59. In some embodiments, the anti-TROP2 antibody (or antigen binding fragment thereof) comprises a VH domain comprising an amino acid sequence that has at least about 95%, 96%, 97%, 98%, 99%, or 100% sequence identity to SEQ ID NO: 44 and/or a VL domain comprising an amino acid sequence that has at least about 95%, 96%, 97%, 98%, 99%, or 100% sequence identity to SEQ ID NO: 47. In some embodiments, the anti-TROP2 antibody (or antigen binding fragment thereof) comprises 3 CDRs of a VH domain comprising SEQ ID NO: 44 and/or 3 CDRs of a VL domain comprising SEQ ID NO: 47. In some embodiments, the 3 CDRs of the VH domain are CDRs according to Kabat, Chothia, AbM or Contact numbering scheme and/or the 3 CDRs of the VL domain are CDRs according to Kabat, Chothia, AbM or Contact numbering scheme. In some embodiments, the anti-TROP2 antibody (or antigen binding fragment thereof) comprises a VH domain comprising SEQ ID NO: 44 and a VL domain comprising SEQ ID NO: 47. In some embodiments, the anti-TROP2 antibody comprises a heavy chain comprising the amino acid sequence of SEQ ID NO: 56 and/or a light chain comprising the amino acid sequence of SEQ ID NO: 59.

In some embodiments, provided are amino acid sequence variants of the anti-TROP2 antibodies described herein ("anti-TROP2 antibody variants"). For example, it may be desirable to improve the binding affinity and/or other biological properties of an anti-TROP2 antibody. Amino acid sequence variants of an anti-TROP2 antibody may be prepared by introducing appropriate modifications into the nucleotide sequence encoding the antibody agent, or by peptide synthesis. Such modifications include, for example, deletions from, and/or insertions into and/or substitutions of residues within the amino acid sequences of the antibody agent. Any combination of deletion, insertion, and substitution can be made to arrive at the final construct, provided that the final construct possesses the desired characteristics, e.g., antigen-binding.

In some embodiments, an anti-TROP2 antibody variants having one or more amino acid substitutions are provided, e.g., the anti-TROP2 antibody variant discussed above. Sites of interest for substitutional mutagenesis include the HVRs and FRs. Amino acid substitutions may be introduced into an antibody agent of interest and the products screened for a desired activity, e.g., retained/improved antigen binding, decreased immunogenicity, or improved ADCC or CDC.

An exemplary substitutional variant is an affinity matured antibody agent, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody agent variants with the desired affinity. Another method to introduce diversity involves CDR-directed approaches, in which several HVR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more CDRs so long as such alterations do not substantially reduce the ability of the antibody agent to bind antigen. For example, conservative alterations (e.g., conservative substitutions as provided herein) that do not substantially reduce binding affinity may be made in HVRs. Such alterations may be outside of CDR "hotspots" or SDRs. In some embodiments of the variant VH and VL sequences provided above, each CDR either is unaltered, or contains no more than one, two, three, four, or five amino acid substitutions.

A useful method for identification of residues or regions of an antibody agent that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody agent with antigen is affected. Further substitutions may be introduced at the amino acid locations demonstrating functional sensitivity to the initial substitutions. Alternatively, or additionally, a crystal structure of an antigen-antibody agent complex can be determined to identify contact points between the antibody agent and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody agent with an N-terminal methionyl residue. Other insertional variants of the antibody agent molecule include the fusion to the N- or C-terminus of the antibody agent to an enzyme (e.g. for ADEPT) or a polypeptide which increases the serum half-life of the antibody agent.

In certain embodiments, the amino acid substitution(s) in an anti-TROP2 antibody variant are conservative amino acid substitution(s). In certain embodiments, the amino acid substitution(s) in an anti-TROP2 antibody variant are non-conservative amino acid substitution(s). In certain embodiments, the amino acid substitutions do not substantially reduce the ability of the antibody to bind antigen. For example, conservative alterations (e.g., conservative substitutions as provided herein) that do not substantially reduce TROP2 binding affinity may be made. The binding affinity of anti-TROP2 antibodies to TROP2 may be assessed using methods known in the art, including, without limitation, immunohistochemical (IHC) assays (e.g., ELISAs) and surface plasmon resonance (SPR).

Conservative substitutions are shown in Table 4 under the heading of "conservative substitutions." More substantial changes are provided in Table 4 under the heading of "exemplary substitutions," and as further described below in reference to amino acid side chain classes. Amino acid substitutions may be introduced into an antibody of interest and the products screened for a desired activity, e.g., retained/improved TROP2 binding.

TABLE 4

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments, the anti-TROP2 antibody cross-reacts with at least one allelic variant of the TROP2 protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring TROP2 (or fragments thereof). In some embodiments, the anti-TROP2 antibody does not cross-react with any allelic variant of the TROP2 protein (or fragments thereof).

In some embodiments, the anti-TROP2 antibody (or antibody variant) binds to (e.g., cross-reacts with) TROP2 proteins from at least two different species. In some embodiments, for example, the anti-TROP2 antibody (or antibody variant) binds to a human TROP2 protein (or fragments thereof) and a TROP2 protein (or fragments thereof) from a mouse, rat, or non-human primate (such as a cynomolgous or rhesus monkey). In some embodiments, the anti-TROP2 antibody may be completely specific for human TROP2 and may not exhibit species or other types of non-human cross-reactivity.

In some embodiments, the anti-TROP2 antibody agent specifically recognizes TROP2 expressed on the cell surface of a cancer cell (such as solid tumor). In some embodiments, the anti-TROP2 antibody agent specifically recognizes TROP2 expressed on the surface tumor cells or on cancerous tissue (e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.). In some embodiments, the anti-TROP2 antibody agent specifically recognizes TROP2 expressed on the cell surface of one or more of cancer cell lines, including, but not limited to, e.g., MDA-MB-468 and HCC38.

In some embodiments, binding of a TROP2 antibody provided herein to the surface of a cell (such as a cancer cell) that expressed TROP2 induces internalization of the anti-TROP2 antibody.

In some embodiments, the $K_d$ of the binding between the anti-TROP2 antibody and a non-target protein is greater than the $K_d$ of the binding between the anti-TROP2 antibody and TROP2. In some embodiments, the non-target protein is not TROP2. In some embodiments, the $K_d$ of the binding of the anti-TROP2 antibody to a non-target protein can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times greater than the $K_d$ of the binding between the anti-TROP2 antibody and TROP2.

The TROP2 antibody that binds specifically to TROP2 can be of any of the various types of antibodies as defined above, but is, in certain embodiments, a human, humanized, chimeric antibody. In some embodiments, the anti-TROP2 antibody is a human antibody. In some embodiments, the anti-TROP2 is a humanized antibody or comprises a human antibody constant domain (e.g., a human Fc domain, such as a human IgG Fc domain, e.g., a human IgG1, a human IgG2, a human IgG3, or a human IgG4 Fc domain). Non-human anti-TROP2 antibodies, as well as anti-TROP2 antibody comprising non-human constant regions are also contemplated. In some embodiments, non-human anti-TROP2 antibodies comprise CDR sequences from an anti-TROP2 antibody as described herein and non-human framework sequences. Non-human framework sequences include, in some embodiments, any sequence that can be used for generating synthetic heavy and/or light chain variable regions using one or more CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-TROP2 antibody includes an anti-TROP2 antibody generated by grafting one or more CDR sequences as described herein onto a non-human framework sequence (e.g., a mouse or chicken framework sequence).

In certain embodiments, the anti-TROP2 antibody comprises an Fc domain of a human IgG, e.g., human IgG1, human IgG2, human IgG3 or human IgG4. In some embodiments, the anti-TROP2 antibody comprises an Fc domain of a human IgG1, as set forth in SEQ ID NO: 64 or SEQ ID NO: 65. (See Table 5 below)

TABLE 5

| |
|---|
| (SEQ ID NO: 64) |
| ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK |
| (SEQ ID NO: 65) |
| ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG |

In certain embodiments, the Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function, including, but not limited to those described elsewhere herein. For example, WO 00/42072 and Shields et al. *J Biol. Chem.* 9(2): 6591-6604 (2001) describes antibody variants with improved or diminished binding to FcRs. The contents of those publications are specifically incorporated herein by reference. The antibody can be in the form of a Fab, Fab', a F(ab)'2, single-chain Fv (scFv), an Fv fragment; a diabody and a linear antibody. Also, the antibody can be a multispecific antibody that binds to TROP2, but also binds one or more other targets and inhibits their function. The antibody can be conjugated to a therapeutic agent (e.g., cytotoxic agent, a radioisotope and a chemotherapeutic agent) or a label for detecting TROP2 in patient samples or in vivo by imaging (e.g., radioisotope, fluorescent dye and enzyme). Other modifications include the conjugation of toxins to anti-TROP2 antibodies provided herein.

Nucleic Acids Encoding Anti-TROP2 Antibodies

Nucleic acid molecules encoding the anti-TROP2 antibodies described herein are also contemplated. In some embodiments, there is provided a nucleic acid (or a set of nucleic acids) encoding an anti-TROP2 antibody, including any of the anti-TROP2 antibodies described herein. In some embodiments, the nucleic acid (or a set of nucleic acids) encoding an anti-TROP2 antibody described herein may further comprises a nucleic acid sequence encoding a peptide tag (such as protein purification tag, e.g., His-tag, HA tag). In some embodiments, the nucleic acid (or set of nucleic acids) encoding an anti-TROP2 antibody comprises a leader sequence. Exemplary nucleic acid sequences are provided below in Table 6.

Also contemplated here are host cells comprising an anti-TROP2 antibody (such as an anti-TROP2 described herein), nucleic acids encoding the polypeptide components of anti-TROP2 antibody (such as an anti-TROP2 described herein), and vector (such as expression vectors) comprising nucleic acid(s) encoding the polypeptide components of an anti-TROP2 antibody described herein.

The present application also includes variants to these nucleic acid sequences. For example, the variants include nucleotide sequences that hybridize to the nucleic acid sequences encoding an anti-TROP2 antibody described herein under at least moderately stringent hybridization conditions.

In some embodiments, the heavy chain of an anti-TROP antibody provided herein is encoded by a nucleic acid comprising a sequence having at least 80%, 85%, 90%, 95%, 96%, 97%, 98%, 99%, 995.% or 100% identity to any one of SEQ ID NOs: 66-71. Additionally or alternatively, in some embodiments, the light chain of an anti-TROP antibody provided herein is encoded by a nucleic acid comprising a sequence having at least 80%, 85%, 90%, 95%, 96%, 97%, 98%, 99%, more than 99% or 100% identity to any one of SEQ ID NOs: 72-76. The sequences of SEQ ID NO: 66-76 are provided in Table 6 below:

TABLE 6

(SEQ ID NO: 66)

CAGGTGCAGCTGGTGCAGTCTGGAGCAGAGGTGAAGAAGCCAGGAGCAAGCGTGAAGGTGTCCTGCAAGGCCTC
TGGCTACACCTTCACAGACTATAGCATCAACTGGGTGAGGCAGGCACCTGGACAGGGACTGGAGTGGATGGGCG
TGATCAGCACATACTATGGCGACGCCTCCTACAATCAGAAGTTTAAGGGCCGCGTGACCATGACCACAGATACC
TCTACAAGCACCGCCTATATGGAGCTGCGGTCCCTGAGATCTGACGATACAGCCGTGTACTATTGTGCCCGGTA
CGGCGACGGCTATAACCAGTTCGATTACTGGGGCCAGGGCACAATGGTGACCGTGAGCTCCGCTAGCACCAAGG
GCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTGGTGACCGTGCCCTCCAGCAGCTTGGGCACCC
AGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCC
CTGTCTCCGGGTAAATGA (SEQ ID NO: 67)

CAGGTGCAGCTGGTGCAGTCTGGAGCAGAGGTGAAGAAGCCAGGAGCAAGCGTGAAGGTGTCCTGCAAGGCCTC
TGGCTACACCTTCACAGACTATAGCATCAACTGGGTGCGGCAGGCACCTGGACAGGGACTGGAGTGGATGGGCG
TGATCAGCACATACTATGGCGACGCCTCCTACAATCAGAAGTTTAAGGGCCGGGTGACCATGACAAGAGATACC
TCCACATCTACCGTGTATATGGAGCTGAGCTCCCTGAGGTCCGAGGATACCGCCGTGTACTATTGTGCCCGCTA
CGGCGACGGCTATAACCAGTTCGATTACTGGGGCCAGGGCACACTGGTGACCGTGTCTAGCGCTAGCACCAAGG
GCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTGGTGACCGTGCCCTCCAGCAGCTTGGGCACCC
AGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCC
CTGTCTCCGGGTAAATGA (SEQ ID NO: 68)

CAGGTGCAGCTGGTGCAGTCTGGAGCAGAGGTGAAGAAGCCAGGAGCAAGCGTGAAGGTGTCCTGCAAGGCCTC
TGGCTACACCTTCACAGACTATAGCATCAACTGGGTGAGGCAGGCACCTGGACAGCGCCTGGAGTGGATGGGCG
TGATCAGCACCTACTATGGCGACGCCTCCTACAATCAGAAGTTTAAGGGCCGGGTGACCATCACAAGAGATACC
TCCGCCTCTACAGCCTATATGGAGCTGAGCTCCCTGCGGTCCGAGGATACAGCCGTGTACTATTGTGCCAGATA
CGGCGACGGCTATAACCAGTTCGATTACTGGGGCCAGGGCACCCTGGTGACAGTGTCTAGCGCTAGCACCAAGG
GCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTGGTGACCGTGCCCTCCAGCAGCTTGGGCACCC

TABLE 6-continued

AGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCC
CTGTCTCCGGGTAAATGA (SEQ ID NO: 69)
CAGGTGCAGCTGGTGCAGAGCGGAGCAGAGGTGAAGAAGCCAGGAAGCTCCGTGAAGGTGTCTTGCAAGGCCAG
CGGCTACACCTTCACAGACTATTCCATCAACTGGGTGAGGCAGGCACCTGGACAGGGACTGGAGTGGATGGGCG
TGATCTCCACCTACTATGGCGACGCCTCTTACAATCAGAAGTTTAAGGGCCGGGTGACCATCACAGCCGATGAG
AGCACCTCCACAGCCTATATGGAGCTGTCTAGCCTGCGGTCTGAGGATACAGCCGTGTACTATTGTGCCAGATA
CGGCGACGGCTATAACCAGTTCGATTACTGGGGCCAGGGCACCCTGGTGACAGTGTCCTCTGCTAGCACCAAGG
GCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTGGTGACCGTGCCCTCCAGCAGCTTGGGCACCC
AGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCC
CTGTCTCCGGGTAAATGA (SEQ ID NO: 70)
GAGGTGCAGCTGGTGCAGTCCGGAGCAGAGGTGAAGAAGCCAGGCGAGAGCCTGAAGATCTCCTGCAAGGGCTC
TGGCTACACCTTCACAGACTATTCTATCAACTGGGTGCGGCAGATGCCTGGCAAGGGACTGGAGTGGATGGGCG
TGATCAGCACCTACTATGGCGACGCCTCCTACAATCAGAAGTTTAAGGGCCAGGTGACCATCTCTGCCGATAAG
TCCATCTCTACAGCCTATCTGCAGTGGAGCTCCCTGAAGGCCAGCGATACAGCCATGTACTATTGTGCCAGATA
CGGCGACGGCTATAACCAGTTCGATTACTGGGGCCAGGGCACCCTGGTGACAGTGTCTAGCGCTAGCACCAAGG
GCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTGGTGACCGTGCCCTCCAGCAGCTTGGGCACCC
AGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCC
AAAACCCAAGGACACCCTCATGATCTCCCGGACCCCTGAGGTCACATGCGTGGTGGTGGACGTGAGCCACGAAG
ACCCTGAGGTCAAGTTCAACTGGTACGTGGACGGCGTGGAGGTGCATAATGCCAAGACAAAGCCGCGGGAGGAG
CAGTACAACAGCACGTACCGTGTGGTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCATCTCCAAAGCCAAAGGGCAGCCCC
GAGAACCACAGGTGTACACCCTGCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCC
CTGTCTCCGGGTAAATGA (SEQ ID NO: 71)
GACATCGTGATGACCCAGTCCCCTGATTCTCTGGCCGTGTCTCTGGGAGAGAGGGCAACAATCAACTGCAGAGT
GTCTGAGAGCGTGGACAGCTACGGCAACAATTTCATGCACTGGTATCAGCAGAAGCCAGGCCAGCCCCCTAAGC
TGCTGATCTACAGGGCAAGCAATCTGGAGTCCGGAGTGCCAGACCGGTTCTCCGGATCTGGAAGCGGAACCGAC
TTCACCCTGACAATCAGCTCCCTGCAGGCAGAGGACGTGGCCGTGTACTATTGTCAGCAGTCCTACGAGGATCC
CTATACCTTTGGCCAGGGCACAAAGCTGGAGATCAAGCGAACGGTGGCTGCACCATCTGTCTTCATCTTCCCGC
CATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAGTGTTAG (SEQ ID NO: 72)
GACGTGGTCATGACCCAGTCCCCCCTGTCTCTGCCTGTGACACTGGGACAGCCAGCAAGCATCTCCTGCAGGGT
GTCTGAGAGCGTGGATTCCTACGGCAACAATTTCATGCACTGGTTTCAGCAGAGGCCAGGCCAGTCTCCCCGGA
GACTGATCTATAGGGCAAGCAACCTGGAGTCCGGAGTGCCTGACCGGTTCTCCGGATCTGGAAGCGGAACCGAC
TTCACCCTGAAGATCTCTAGGGTGGAGGCAGAGGACGTGGGCGTGTACTATTGTCAGCAGAGCTACGAGGATCC
ATATACCTTCGGCGGCGGCACAAAGGTGGAGATCAAGCGAACGGTGGCTGCACCATCTGTCTTCATCTTCCCGC
CATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAGTGTTAG (SEQ ID NO: 73)
GACATCGTGATGACCCAGTCCCCTCTGTCTCTGCCAGTGACACCTGGAGAGCCAGCAAGCATCTCCTGCAGGGT
GTCTGAGAGCGTGGATTCCTACGGCAACAATTTCATGCACTGGTATCTGCAGAAGCCCGGCCAGTCTCCTCAGC
TGCTGATCTACAGGGCAAGCAACCTGGAGTCCGGAGTGCCAGACAGATTCTCCGGATCTGGAAGCGGAACCGAC

TABLE 6-continued

TTCACCCTGAAGATCTCTAGGGTGGAGGCAGAGGACGTGGGCGTGTACTATTGTCAGCAGAGCTACGAGGATCC
CTATACCTTTGGCGGCGGCACAAAGGTGGAGATCAAGCGAACGGTGGCTGCACCATCTGTCTTCATCTTCCCGC
CATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAGTGTTAG (SEQ ID NO: 74)
GAGATCGTGCTGACCCAGTCCCCAGCCACACTGTCTCTGAGCCCAGGAGAGAGGGCCACCCTGTCTTGCCGCGT
GTCCGAGTCTGTGGATAGCTACGGCAACAATTTCATGCACTGGTATCAGCAGAAGCCAGGACAGGCACCTAGGC
TGCTGATCTACAGAGCAAGCAACCTGGAGTCCGGAATCCCAGCACGGTTCAGCGGATCCGGCTCTGGCACAGAC
TTTACCCTGACAATCAGCTCCCTGGAGCCTGAGGATTTCGCCGTGTACTATTGTCAGCAGTCTTACGAGGACCC
ATATACCTTTGGCGGCGGCACAAAGGTGGAGATCAAGCGAACGGTGGCTGCACCATCTGTCTTCATCTTCCCGC
CATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAGTGTTAG (SEQ ID NO: 75)
GATATCCAGATGACCCAGTCTCCTAGCTCCCTGTCCGCCTCTGTGGGCGATAGGGTGACCATCACATGCAGAGT
GAGCGAGTCCGTGGACTCCTACGGCAACAATTTCATGCACTGGTATCAGCAGAAGCCCGGCAAGGCCCCTAAGC
TGCTGATCTACAGGGCCTCTAACCTGGAGAGCGGAGTGCCATCCCGGTTTTCTGGAAGCGGATCCGGAACCGAC
TTCACCTTTACAATCTCTAGCCTGCAGCCAGAGGATATCGCCACATACTATTGTCAGCAGAGCTACGAGGACCC
CTATACCTTCGGCGGCGGCACAAAGCTGGAGATCAAGCGAACGGTGGCTGCACCATCTGTCTTCATCTTCCCGC
CATCTGATGAGCAGTTGAAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGACAGCAA
GGACAGCACCTACAGCCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAGTGTTAG (SEQ ID NO: 76)
ATGGGCTGGAGCTGGATCCTGCTGTTCCTCCTGAGCGTGACAGCAGGAGTGCACAGCCAGGTGCAGCTGGTGCA
GTCTGGAGCAGAGGTGAAGAAGCCAGGAGCAAGCGTGAAGGTGTCCTGCAAGGCCTCTGGCTACACCTTCACAG
ACTATAGCATCAACTGGGTGAGGCAGGCACCTGGACAGGGACTGGAGTGGATGGGCGTGATCAGCACATACTAT
GGCGACGCCTCCTACAATCAGAAGTTTAAGGGCCGCGTGACCATGACCACAGATACCTCTACAAGCACCGCCTA
TATGGAGCTGCGGTCCCTGAGATCTGACGATACAGCCGTGTACTATTGTGCCCGGTACGGCGACGGCTATAACC
AGTTCGATTACTGGGGCCAGGGCACAATGGTGACCGTGAGCTCCGCTAGCACCAAGGGCCCATCGGTCTTCCCC
CTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATG
A (SEQ ID NO: 77)
ATGGGCTGGAGCTGGATCCTGCTGTTCCTCCTGAGCGTGACAGCAGGAGTGCACAGCCAGGTGCAGCTGGTGCA
GTCTGGAGCAGAGGTGAAGAAGCCAGGAGCAAGCGTGAAGGTGTCCTGCAAGGCCTCTGGCTACACCTTCACAG
ACTATAGCATCAACTGGGTGCGGCAGGCACCTGGACAGGGACTGGAGTGGATGGGCGTGATCAGCACATACTAT
GGCGACGCCTCCTACAATCAGAAGTTTAAGGGCCGGGTGACCATGACAAGAGATACCTCCACATCTACCGTGTA
TATGGAGCTGAGCTCCCTGAGGTCCGAGGATACCGCCGTGTACTATTGTGCCCGCTACGGCGACGGCTATAACC
AGTTCGATTACTGGGGCCAGGGCACACTGGTGACCGTGTCTAGCGCTAGCACCAAGGGCCCATCGGTCTTCCCC
CTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATG
A (SEQ ID NO: 78)
ATGGGCTGGAGCTGGATCCTGCTGTTCCTCCTGAGCGTGACAGCAGGAGTGCACAGCCAGGTGCAGCTGGTGCA
GTCTGGAGCAGAGGTGAAGAAGCCAGGAGCAAGCGTGAAGGTGTCCTGCAAGGCCTCTGGCTACACCTTCACAG
ACTATAGCATCAACTGGGTGAGGCAGGCACCTGGACAGCGCCTGGAGTGGATGGGCGTGATCAGCACCTACTAT
GGCGACGCCTCCTACAATCAGAAGTTTAAGGGCCGGGTGACCATCACAAGAGATACCTCCGCCTCTACAGCCTA
TATGGAGCTGAGCTCCCTGCGGTCCGAGGATACAGCCGTGTACTATTGTGCCAGATACGGCGACGGCTATAACC
AGTTCGATTACTGGGGCCAGGGCACCCTGGTGACAGTGTCTAGCGCTAGCACCAAGGGCCCATCGGTCTTCCCC

TABLE 6-continued

CTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATG
A (SEQ ID NO: 79)
ATGGGCTGGAGCTGGATCCTGCTGTTCCTCCTGAGCGTGACAGCAGGAGTGCACAGCCAGGTGCAGCTGGTGCA
GAGCGGAGCAGAGGTGAAGAAGCCAGGAAGCTCCGTGAAGGTGTCTTGCAAGGCCAGCGGCTACACCTTCACAG
ACTATTCCATCAACTGGGTGAGGCAGGCACCTGGACAGGGACTGGAGTGGATGGGCGTGATCTCCACCTACTAT
GGCGACGCCTCTTACAATCAGAAGTTTAAGGGCCGGGTGACCATCACAGCCGATGAGAGCACCTCCACAGCCTA
TATGGAGCTGTCTAGCCTGCGGTCTGAGGATACAGCCGTGTACTATTGTGCCAGATACGGCGACGGCTATAACC
AGTTCGATTACTGGGGCCAGGGCACCCTGGTGACAGTGTCCTCTGCTAGCACCAAGGGCCCATCGGTCTTCCCC
CTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATG
A (SEQ ID NO: 80)
ATGGGCTGGAGCTGGATCCTGCTGTTCCTCCTGAGCGTGACAGCAGGAGTGCACAGCGAGGTGCAGCTGGTGCA
GTCCGGAGCAGAGGTGAAGAAGCCAGGCGAGAGCCTGAAGATCTCCTGCAAGGGCTCTGGCTACACCTTCACAG
ACTATTCTATCAACTGGGTGCGGCAGATGCCTGGCAAGGGACTGGAGTGGATGGGCGTGATCAGCACCTACTAT
GGCGACGCCTCCTACAATCAGAAGTTTAAGGGCCAGGTGACCATCTCTGCCGATAAGTCCATCTCTACAGCCTA
TCTGCAGTGGAGCTCCCTGAAGGCCAGCGATACAGCCATGTACTATTGTGCCAGATACGGCGACGGCTATAACC
AGTTCGATTACTGGGGCCAGGGCACCCTGGTGACAGTGTCTAGCGCTAGCACCAAGGGCCCATCGGTCTTCCCC
CTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTGACAAAACTCACACATG
CCCACCGTGCCCAGCACCTGAACTCCTGGGGGGACCGTCAGTCTTCCTCTTCCCCCCAAAACCCAAGGACACCC
TCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATG
A (SEQ ID NO: 81)
ATGGGCTGGAGCTGGATCCTGCTGTTCCTCCTGAGCGTGACAGCAGGAGTGCACAGCGACATCGTGATGACCCA
GTCCCCTGATTCTCTGGCCGTGTCTCTGGGAGAGAGGGCAACAATCAACTGCAGAGTGTCTGAGAGCGTGGACA
GCTACGGCAACAATTTCATGCACTGGTATCAGCAGAAGCCAGGCCAGCCCCCTAAGCTGCTGATCTACAGGGCA
AGCAATCTGGAGTCCGGAGTGCCAGACCGGTTCTCCGGATCTGGAAGCGGAACCGACTTCACCCTGACAATCAG
CTCCCTGCAGGCAGAGGACGTGGCCGTGTACTATTGTCAGCAGTCCTACGAGGATCCCTATACCTTTGGCCAGG
GCACAAAGCTGGAGATCAAGCGAACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG (SEQ ID NO: 82)
ATGGGCTGGAGCTGGATCCTGCTGTTCCTCCTGAGCGTGACAGCAGGAGTGCACAGCGACGTGGTCATGACCCA
GTCCCCCCTGTCTCTGCCTGTGACACTGGGACAGCCAGCAAGCATCTCCTGCAGGGTGTCTGAGAGCGTGGATT
CCTACGGCAACAATTTCATGCACTGGTTTCAGCAGAGGCCAGGCCAGTCTCCCCGGAGACTGATCTATAGGGCA
AGCAACCTGGAGTCCGGAGTGCCTGACCGGTTCTCCGGATCTGGAAGCGGAACCGACTTCACCCTGAAGATCTC
TAGGGTGGAGGCAGAGGACGTGGGCGTGTACTATTGTCAGCAGAGCTACGAGGATCCATATACCTTCGGCGGCG
GCACAAAGGTGGAGATCAAGCGAACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC

TABLE 6-continued

```
TCAGCAGCACCCTGACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG

                                                                (SEQ ID NO: 83)
ATGGGCTGGAGCTGGATCCTGCTGTTCCTCCTGAGCGTGACAGCAGGAGTGCACAGCGACATCGTGATGACCCA
GTCCCCTCTGTCTCTGCCAGTGACACCTGGAGAGCCAGCAAGCATCTCCTGCAGGGTGTCTGAGAGCGTGGATT
CCTACGGCAACAATTTCATGCACTGGTATCTGCAGAAGCCCGGCCAGTCTCCTCAGCTGCTGATCTACAGGGCA
AGCAACCTGGAGTCCGGAGTGCCAGACAGATTCTCCGGATCTGGAAGCGGAACCGACTTCACCCTGAAGATCTC
TAGGGTGGAGGCAGAGGACGTGGGCGTGTACTATTGTCAGCAGAGCTACGAGGATCCCTATACCTTTGGCGGCG
GCACAAAGGTGGAGATCAAGCGAACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG

                                                                (SEQ ID NO: 84)
ATGGGCTGGAGCTGGATCCTGCTGTTCCTCCTGAGCGTGACAGCAGGAGTGCACAGCGAGATCGTGCTGACCCA
GTCCCCAGCCACACTGTCTCTGAGCCCAGGAGAGAGGGCCACCCTGTCTTGCCGCGTGTCCGAGTCTGTGGATA
GCTACGGCAACAATTTCATGCACTGGTATCAGCAGAAGCCAGGACAGGCACCTAGGCTGCTGATCTACAGAGCA
AGCAACCTGGAGTCCGGAATCCCAGCACGGTTCAGCGGATCCGGCTCTGGCACAGACTTTACCCTGACAATCAG
CTCCCTGGAGCCTGAGGATTTCGCCGTGTACTATTGTCAGCAGTCTTACGAGGACCCATATACCTTTGGCGGCG
GCACAAAGGTGGAGATCAAGCGAACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG

                                                                (SEQ ID NO: 85)
ATGGGCTGGAGCTGGATCCTGCTGTTCCTCCTGAGCGTGACAGCAGGAGTGCACAGCGATATCCAGATGACCCA
GTCTCCTAGCTCCCTGTCCGCCTCTGTGGGCGATAGGGTGACCATCACATGCAGAGTGAGCGAGTCCGTGGACT
CCTACGGCAACAATTTCATGCACTGGTATCAGCAGAAGCCCGGCAAGGCCCCTAAGCTGCTGATCTACAGGGCC
TCTAACCTGGAGAGCGGAGTGCCATCCCGGTTTTCTGGAAGCGGATCCGGAACCGACTTCACCTTTACAATCTC
TAGCCTGCAGCCAGAGGATATCGCCACATACTATTGTCAGCAGAGCTACGAGGACCCCTATACCTTCGGCGGCG
GCACAAAGCTGGAGATCAAGCGAACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAG
GGCCTGAGCTCGCCCGTCACAAAGAGCTTCAACAGGGGAGAGTGTTAG
```

Also provided are vectors in which a nucleic acid described herein is inserted.

In brief summary, the expression of an anti-TROP2 antibody by a natural or synthetic nucleic acid encoding the anti-TROP2 antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the nucleic acid(s) encoding the anti-TROP2 antibody is inducible. In some embodiments, the nucleic acid(s) encoding the anti-TROP2 antibody agent is operably linked to an inducible promoter, including any inducible promoter described herein.

Methods of Antibody Production

An antibody of the present disclosure may be produced by any means known in the art. Exemplary techniques for antibody production are described below; however these exemplary techniques are provided for illustrative purposes only and are not intended to be limiting. In addition, exemplary antibody properties contemplated for use with the antibodies described herein are further described.

To prepare an antigen, the antigen may be purified or otherwise obtained from a natural source, or it may be expressed using recombinant techniques. In some embodiments, the antigen may be used as a soluble protein. In some embodiments, the antigen may be conjugate to another polypeptide or other moiety, e.g., to increase its immunogenicity. For example, an antigen described herein may be coupled with an Fc region. In some embodiments, a cell expressing the antigen on its cell surface may be used as the antigen.

Polyclonal antibodies can be raised in an animal by multiple subcutaneous (sc) or intraperitoneal (ip) injections of the antigen and an adjuvant. For example, descriptions of chicken immunization are described herein. In some embodiments, the antigen is conjugated with an immunogenic protein, e.g., keyhole limpet hemocyanin, serum albumin, bovine thyroglobulin, or soybean trypsin inhibitor using a bifunctional or derivatizing agent. Exemplary methods for immunization of chickens are provided herein. Relevant methods suitable for a variety of other organisms, such as mammals, are well known in the art.

As described supra, monoclonal antibodies may be produced by a variety of methods. In some embodiments, a monoclonal antibody of the present disclosure is made using the hybridoma method first described by Kohler et al., *Nature,* 256:495 (1975), and further described in Hongo et al., *Hybridoma,* 14 (3): 253-260 (1995); Harlow et al., *Antibodies: A Laboratory Manual*, (Cold Spring Harbor Laboratory Press, 2nd ed. 1988); and Hammerling et al., in: *Monoclonal Antibodies and T-Cell Hybridomas* 563-681 (Elsevier, N.Y., 1981). Human hybridoma technology (Trioma technology) is described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005). A culture medium in which hybridoma cells are grown may be screened for the presence of an antibody of interest, e.g., by in vitro binding assay, immunoprecipitation, ELISA, RIA, etc.; and the binding affinity may be determined, e.g., by Scatchard analysis. A hybridoma that produces an antibody with desired binding properties can be subcloned and grown using known culture techniques, grown in vivo as ascites tumors in an animal, and the like.

In some embodiments, a monoclonal antibody is made using a library method, such as a phage display library. See, e.g., Hoogenboom et al. in *Methods in Molecular Biology* 178:1-37 (O'Brien et al., ed., Human Press, Totowa, NJ, 2001). In some embodiments, repertoires of VH and VL genes are cloned by polymerase chain reaction (PCR) and recombined randomly in phage libraries, which are then screened for antigen-binding phage, e.g., as described in Winter et al., *Ann. Rev. Immunol.,* 12: 433-455 (1994). Phage typically display antibody fragments, either as single-chain Fv (scFv) fragments or as Fab fragments. Alternatively, the naive repertoire can be cloned (e.g., from human) to provide a single source of antibodies to a wide range of non-self and also self-antigens without any immunization as described by Griffiths et al., *EMBO* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992).

In some embodiments, an antibody of the present disclosure is a chicken antibody. Chicken antibodies can be produced using various techniques known in the art; see, e.g., U.S. Pat. Nos. 6,143,559; 8,592,644; and 9,380,769.

In some embodiments, an antibody of the present disclosure is a chimeric antibody. See, e.g., U.S. Pat. No. 4,816,567 and Morrison et al., *Proc. Natl. Acad. Sci. USA,* 81:6851-6855 (1984). In some embodiments, a chimeric antibody comprises a non-human variable region (e.g., a variable region derived from a chicken, mouse, rat, hamster, rabbit, or non-human primate, such as a monkey) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. A non-human antibody can be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody (e.g., a chicken antibody), and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR or CDR residues are derived), e.g., to restore or improve antibody specificity or affinity. Humanized antibodies and methods of making them are reviewed, e.g., in Almagro and Fransson, *Front. Biosci.* 13:1619-1633 (2008). Methods of humanizing a chicken antibody have also been described, e.g., in WO2005014653.

Human framework regions useful for humanization include but are not limited to: framework regions selected using the "best-fit" method; framework regions derived from the consensus sequence of human antibodies of a particular subgroup of light or heavy chain variable regions; human somatically mutated framework regions or human germline framework regions; and framework regions derived from screening FR libraries. See, e.g., Sims et al. *J. Immunol.* 151:2296 (1993); Carter et al. *Proc. Natl. Acad. Sci. USA,* 89:4285 (1992); Presta et al. *J. Immunol.,* 151:2623 (1993); Almagro and Fransson, *Front. Biosci.* 13:1619-1633 (2008); and Baca et al., *J. Biol. Chem.* 272:10678-10684 (1997).

In some embodiments, an antibody of the present disclosure is a human antibody. Human antibodies can be produced using various techniques known in the art. In some embodiments, the human antibody is produced by a non-human animal, such as the genetically engineered chickens (see, e.g., U.S. Pat. Nos. 8,592,644; and 9,380,769) and/or mice described herein. Human antibodies are described generally in Lonberg, *Curr. Opin. Immunol.* 20:450-459 (2008).

In some embodiments, an antibody of the present disclosure is an antibody fragment, including without limitation a Fab, F(ab')2, Fab'-SH, Fv, or scFv fragment, or a single domain, single heavy chain, or single light chain antibody. Antibody fragments can be generated, e.g., by enzymatic digestion or by recombinant techniques. In some embodiments, Proteolytic digestion of an intact antibody is used to generate an antibody fragment, e.g., as described in Morimoto et al., *Journal of Biochemical and Biophysical Methods* 24:107-117 (1992) and Brennan et al., *Science,* 229:81 (1985). In some embodiments, an antibody fragment is produced by a recombinant host cell. For example, Fab, Fv and ScFv antibody fragments are expressed by and secreted from *E. coli*. Antibody fragments can alternatively be isolated from an antibody phage library.

Fab'-SH fragments can be directly recovered from *E. coli* and chemically coupled to form $F(ab')_2$ fragments. See Carter et al., *Bio/Technology* 10:163-167 (1992). F(ab') 2 fragments can also be isolated directly from a recombinant host cell culture. Fab and F(ab') 2 fragment with increased in vivo half-life comprising salvage receptor binding epitope residues are described in U.S. Pat. No. 5,869,046.

In some embodiments, an antibody is a single chain Fv fragment (scFv). See WO 93/16185 and U.S. Pat. Nos. 5,571,894 and 5,587,458. scFv fusion proteins can be constructed to produce a fusion of an effector protein at either the amino or the carboxy terminus of an scFv. The antibody fragment may also be a "linear antibody", e.g., as described in U.S. Pat. No. 5,641,870, for example. Such linear antibodies may be monospecific or bispecific.

In some embodiments, an antibody of the present disclosure is a multispecific antibody. Multispecific antibodies possess binding specificities against more than one antigen (e.g., having two, three, or more binding specificities). In some embodiments, the antibody is a bispecific antibody. In some embodiments, a bispecific antibody comprises two different binding specificities for the same antigen (e.g., having different binding affinity and/or specific epitope of the same antigen). In some embodiments, a bispecific antibody comprises binding specificities for two distinct antigens. In some embodiments, the bispecific antibody is a full-length or intact antibody. In some embodiments, the bispecific antibody is an antibody fragment of the present disclosure.

Various methods are known in the art for generating and purifying a bispecific antibody. Numerous approaches have been described. One approach is the "knobs-into-holes" or "protuberance-into-cavity" approach (see, e.g., U.S. Pat. No. 5,731,168). In some embodiments, heterodimerization of Fc domain monomers is promoted by introducing different, but compatible, substitutions in the two Fc domain monomers, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain monomer and involved in the dimerization of two Fc domain monomers. In some embodiments, a hole in one CH3 antibody constant domain is created to accommodate a knob in another CH3 antibody constant domain, such that the knob and hole amino acids act to promote or favor the heterodimerization of the two Fc domain monomers. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain monomer includes the knob mutation T366W and the other Fc domain monomer includes hole mutations T366S, L358A, and Y407V. Examples of knob-into-hole amino acid pairs include, but are not limited to, those shown in Table 5.

TABLE 5

| Knob-into-Hole Amino Acid Mutations | | | | | | | | |
|---|---|---|---|---|---|---|---|---|
| Fc domain 1 | Y407T | Y407A | F405A | T394S | T366S L358A Y407V | T394W Y407T | T394S Y407A | T366W T394S |
| Fc domain 2 | T366Y | T366W | T394W | F405W | T366W | T366Y F405A | T366W F405W | F405W Y407A |

Another approach uses antibody variable domains with the desired binding specificities (antibody-antigen combining sites) fused to immunoglobulin constant domain sequences, e.g., with an immunoglobulin heavy chain constant domain, comprising at least part of the hinge, CH2, and CH3 regions. In some embodiments, the bispecific antibody has a hybrid immunoglobulin heavy chain with a first binding specificity in one arm and a hybrid immunoglobulin heavy chain-light chain pair (providing a second binding specificity) in the other arm. See WO 94/04690. Another approach uses cross-linking (see, e.g., U.S. Pat. No. 4,676,980) to produce a heteroconjugate antibody. In some embodiments, bispecific antibodies can be prepared using chemical linkage (see, e.g., Brennan et al., Science, 229: 81 (1985)) to proteolytically cleave an intact antibody into $F(ab')_2$ fragments that are reduced in the presence of a dithiol complexing agent and converted to thionitrobenzoate (TNB) derivatives, one of which is reconverted to the Fab'-thiol by reduction and mixed with the other Fab'-TNB derivative to form the bispecific antibody. In some embodiments, Fab'-SH fragments are chemically coupled. In some embodiments, bispecific antibody fragments are produced in cell culture using leucine zippers, as in Kostelny et al., *J. Immunol.,* 148(5):1547-1553 (1992). For other bispecific antibody formats, see, e.g., Spiess, C. et al. (2015) *Mol. Immunol.* 67:95-106.

In some embodiments, an antibody of the present disclosure is a diabody. See, e.g., Hollinger et al., *Proc. Natl. Acad. Sci. USA,* 90:6444-6448 (1993). In a diabody, the $V_H$ and $V_L$ domains of one fragment pair with complementary $V_L$ and $V_H$ domains of another fragment, thus forming two antigen-binding sites. Another strategy for making bispecific antibody fragments by the use of single-chain Fv (sFv) dimers has also been reported. See Gruber et al, *J. Immunol,* 152:5368 (1994).

In some embodiments, an antibody of the present disclosure is a single-domain antibody. A single-domain antibody refers to a single polypeptide chain comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1). In one embodiment, a single-domain antibody includes all or a portion of the heavy chain variable domain of an antibody. Camelid antibodies are also known.

Antibodies can be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An antibody of the present disclosure can be produced recombinantly as a fusion polypeptide with a heterologous polypeptide, e.g., a signal sequence or other polypeptide having a specific cleavage site at the N-terminus of the mature protein or polypeptide. The heterologous signal sequence selected can be one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from alkaline phosphatase, penicillinase, 1pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, etc. In mammalian cell expression, mammalian signal sequences as well as viral secretory leaders, for example, the herpes simplex gD signal, are available.

Both expression and cloning vectors contain a nucleic acid sequence that enables the vector to replicate in one or more selected host cells, e.g., to allow the vector to replicate independently of the host chromosomal DNA. This sequence can include origins of replication or autonomously replicating sequences. Such sequences are well known for a variety of bacteria, yeast, and viruses. Generally, the origin of replication component is not needed for mammalian expression vectors (the SV40 origin may be used because it contains the early promoter).

Expression and cloning vectors can contain a selection gene or selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media. Examples of dominant selection use the drugs neomycin, mycophenolic acid and hygromycin. Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, and the like. For example, a Chinese hamster ovary (CHO) cell line deficient in endogenous DHFR activity transformed with the DHFR gene is identified by culturing the transformants in a culture medium containing methotrexate (Mtx), a competitive antagonist of DHFR.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoter sequences are known for eukaryotes. Yeast promoters are well known in the art and can include inducible promoters/enhancers regulated by growth conditions. Virtually all eukaryotic genes have an AT-rich region located approximately 25 to 30 bases upstream from the site where transcription is initiated. Examples include without limitation the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Antibody transcription from vectors in mammalian host cells can be controlled, for example, by promoters obtained from the genomes of viruses. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Alternatively, the Rous Sarcoma Virus long terminal repeat can be used as the promoter.

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus.

Expression vectors used in eukaryotic host cells (yeast, fungi, insect, plant, animal, human, or nucleated cells from other multicellular organisms) will also contain sequences necessary for the termination of transcription and for stabilizing the mRNA.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, etc. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006).

Plant cell cultures of cotton, corn, potato, soybean, petunia, tomato, duckweed (*Leninaceae*), alfalfa (*M. truncatula*), and tobacco can also be utilized as hosts.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified.

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

The host cells of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of skill in the art.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli.*

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps.

Glycosylation Variants

In some embodiments, an anti-TROP2 antibody provided herein is altered to increase or decrease the extent to which the anti-TROP2 antibody is glycosylated. Addition or deletion of glycosylation sites to an anti-TROP2 antibody may be conveniently accomplished by altering the amino acid sequence of the anti-TROP2 antibody or polypeptide portion thereof such that one or more glycosylation sites is created or removed.

Where the anti-TROP2 antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-TROP2 antibody of the invention may be made in order to create anti-TROP2 antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody agent therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-TROP2 antibody variants are provided comprising an Fc region wherein a carbohydrate structure attached to the Fc region has reduced fucose or lacks fucose, which may improve ADCC function. Specifically, anti-TROP2 antibodies are contemplated herein that have reduced fucose relative to the amount of fucose on the same anti-TROP2 antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-TROP2 antibody is one wherein less than about 50%, 40%, 30%, 20%, 10%, or 5% of the N-linked glycans thereon comprise fucose. For example, the amount of fucose in such an anti-TROP2 antibody may be from 1% to 80%, from 1% to 65%, from 5% to 65% or from 20% to 40%. In some embodiments, the anti-TROP2 antibody is one wherein none of the N-linked glycans thereon comprise fucose, i.e., wherein the anti-TROP2 antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody agent variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such asa-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Also provided are anti-TROP2 antibody variants with bisected oligosaccharides, e.g., in which a biantennary oligosaccharide attached to the Fc region of the anti-TROP2 antibody is bisected by GlcNAc. Such anti-TROP2 antibody variants may have reduced fucosylation and/or improved ADCC function. Examples of such antibody agent variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Anti-TROP2 antibody variants with at least one galactose residue in the oligosaccharide attached to the Fc region are also provided. Such anti-TROP2 antibody variants may have improved CDC function. Such antibody agent variants are described, e.g., in WO 1997/30087 (Patel et al.); WO 1998/58964 (Raju, S.); and WO 1999/22764 (Raju, S.).

In some embodiments, the anti-TROP2 antibody variants comprising an Fc region are capable of binding to an FcγRIII In some embodiments, the anti-TROP2 antibody variants comprising an Fc region have ADCC activity in the presence of human effector cells (e.g., T cell) or have increased ADCC activity in the presence of human effector cells compared to the otherwise same anti-TROP2 antibody comprising a human wild-type IgG1Fc region.

Cysteine Engineered Variants

In some embodiments, it may be desirable to create cysteine engineered anti-TROP2 antibodies in which one or more amino acid residues are substituted with cysteine residues. In some embodiments, the substituted residues occur at accessible sites of the anti-TROP2 antibody. By substituting those residues with cysteine, reactive thiol groups are thereby positioned at accessible sites of the anti-TROP2 antibody and may be used to conjugate the anti-TROP2 antibody to other moieties, such as drug moieties or linker-drug moieties, to create an anti-TROP22 immunoconjugate, as described further herein. Cysteine engineered anti-TROP2 antibodies may be generated as described, e.g., in U.S. Pat. No. 7,521,541.

Effector Function Engineering

It may be desirable to modify an anti-TROP2 antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.,* 176: 1191-1195 (1992) and Shapes, *J. Immunol.,* 148: 2918-2922 (1992). Homodimeric antibodies with enhanced anti-tumor activity can also be prepared using heterobifunctional cross-linkers as described in Wolff et al., *Cancer Research,* 53: 2560-2565 (1993). Alternatively, an antibody can be engineered to comprise usual Fc regions and can thereby have enhanced complement lysis and ADCC capabilities. See, Stevenson et al., *Anti-Cancer Drug* Design3: 219-230 (1989).

Mutations or alterations in the Fc region sequences can be made to improve FcR binding (e.g., binding to FcγR, FcRn). In some embodiments, an anti-TROP2 antibody provided herein comprises at least one altered effector function, e.g., altered ADCC, CDC, and/or FcRn binding compared to a native IgG or a parent antibody. In some embodiments, the effector function of the antibody comprising the mutation or alteration is increased relative to the parent antibody. In some embodiments, the effector function of the antibody comprising the mutation or alteration is decreased relative to the parent antibody. Examples of several useful specific mutations are described in, e.g., Shields, R L et al. (2001) *JBC* 276(6)6591-6604; Presta, L. G., (2002) *Biochemical Society Transactions* 30(4):487-490; and WO 00/42072.

In some embodiments, an anti-TROP2 antibody provided herein comprises an Fc receptor mutation, e.g., a substitution mutation at least one position of the Fc region. Such substitution mutation(s) may be made to amino acid positions in the Fc domain that include, but are not limited to, e.g., 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439, wherein the numbering of the residues in the Fc region is according to the EU numbering system. In some embodiments, the Fc receptor mutation is a D265A substitution. In some embodiments, the Fc receptor mutation is a N297A substitution. Additional suitable mutations are well known in the art. Exemplary mutations are set forth in, e.g., U.S. Pat. No. 7,332,581.

Multispecific Antibodies

Multispecific antibodies are monoclonal, preferably human or humanized, antibodies that have binding specificities for two or more different antigens (e.g., bispecific antibodies have binding specificities for at least two antigens). For example, one of the binding specificities can be for the TROP2 protein, the other one can be for any other antigen. According to one preferred embodiment, the other antigen is a cell-surface protein or receptor or receptor subunit. Thus, according to one embodiment, a bispecific antibody of this invention can bind both TROP2 and, e.g., a second cell surface receptor.

Suitable methods for making bispecific antibodies are well known in the art. For example, the recombinant production of bispecific antibodies is based on the co-expression of two immunoglobulin heavy-chain/light-chain pairs, where the two heavy chains have different specificities. Milstein and Cuello, *Nature,* 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO,* 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH 1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology,* 121: 210 (1986).

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *PNAS USA,* 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al. *J. Immunol.* 147: 60 (1991).

Chimeric Molecules

An anti-TROP2 antibody provided herein (or an antigen-binding fragment thereof) may also be modified form a chimeric molecule comprising the antibody fused to another, heterologous polypeptide or amino acid sequence.

In one embodiment, such a chimeric molecule comprises a fusion of an anti-TROP2 antibody provided herein (or an antigen-binding fragment thereof) with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of an anti-TROP2 antibody provided herein (or an antigen-binding fragment thereof) with a tag polypeptide which provides an epitope to which an anti-tag antibody can selectively bind. The epitope tag is generally placed at the amino- or carboxyl-terminus of a polypeptide. The presence of such epitope-tagged forms of an anti-TROP2 antibody provided herein (or an antigen-binding fragment thereof) can be detected using an antibody against the tag polypeptide. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

Immunoconjugates and Covalent Modifications

The invention also pertains to immunoconjugates such as antibody drug conjugates or "ADC") comprising an anti-TROP2 antibody described herein (or an antigen-binding fragment thereof) conjugated to second moiety or "active moiety." In some embodiments, the second moiety (e.g., "active moiety") is a therapeutic agent. In some embodiments, the therapeutic agent is or comprises a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides, and conotoxin. A variety of radionuclides are available for the production of radioconjugated antibodies. Examples include $^{212}$Bi, $^{131}$I, $^{131}$In, $^{90}$Y and $^{186}$Re. Exemplary chemotherapeutic agents useful in the generation of such immunoconjugates are described elsewhere herein.

In certain embodiments, an anti-TROP2 antibody provided herein (or an antigen-binding fragment thereof) is conjugated to maytansine, a maytansinoid, an auristatin, or calicheamicin. In certain embodiments, an anti-TROP2 antibody provided herein (or an antigen-binding fragment thereof) is conjugated to the maytansinoid DM1. In certain embodiments, an anti-TROP2 antibody provided herein (or an antigen-binding fragment thereof) is conjugated to monomethyl auristatin E (MMAE). In certain embodiments, an anti-TROP2 antibody provided herein (or an antigen-binding fragment thereof) is conjugated to monomethyl auristatin F (MMAF).

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Also provided are heteroconjugate antibodies comprising an anti-TROP2 antibody described herein covalently joined to at least one other antibody. Heteroconjugate antibodies have, for example, been proposed to target immune-system cells to unwanted cells (U.S. Pat. No. 4,676,980), and for treatment of HIV infection. Heteroconjugate antibodies comprising an anti-TROP2 antibody described herein can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Also provided is an anti-TROP2 antibody comprising at least one covalent modification. One type of covalent modification includes reacting targeted amino acid residues of an anti-TROP2 with an organic derivatizing agent that is capable of reacting with selected side chains or the N- or C-terminal residues of the antibody. Commonly used crosslinking agents include, but are not limited to, e.g., 1,1-bis (diazoacetyl)-2-phenylethane, glutaraldehyde, N-hydroxysuccinimide esters, for example, esters with 4-azidosalicylic acid, homobifunctional imidoesters, including di succinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification comprises linking an anti-TROP2 antibody provided herein (or an antigen-binding fragment thereof) to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

In some embodiment, provided herein is an anti-TROP2 antibody or antigen binding fragment thereof (e.g., as described elsewhere herein) conjugated to a conjugate moiety (such as a moiety that improves a pharmacokinetic property of the anti-TROP2 antibody or fragment thereof, a drug, a toxin (such as described elsewhere herein) therapeutic moiety, diagnostic moiety, or a label). In some embodiments, anti-TROP2 antibody or antigen binding fragment thereof is conjugated to the conjugate moiety via a linker. In some embodiments, the linker is a cleavable linker. In some embodiments, the linker is a non-cleavable linker. In some embodiments, the anti-TROP2 antibody of fragment thereof is conjugated to the conjugate moiety via an endogenous acceptor glutamine residue on the antibody or fragment thereof. In some embodiments, the anti-TROP2 antibody or fragment thereof comprises an Fc region, and the endogenous acceptor glutamine residue is on the Fc region. Further details regarding antibodies conjugated to conjugate moieties in such manner are provided in WO2015/191882 and US20170106096, the contents of which are expressly incorporated herein by reference in their entirety.

Exemplary Methods of Producing Anti-TROP2 Antibody Drug Conjugates

In some embodiments, an anti-TROP2 antibody provided herein (or an antigen-binding fragment thereof) is attached to a conjugate moiety (e.g., "active moiety") according to a method described in WO 2015/191883, the contents of which are incorporated herein by reference in their entirety. The methods described in WO 2015/191883 permit the efficient attachment of a conjugate moiety (such as a drug) to an intact, unmodified anti-TROP2 antibody (e.g., an anti-TROP2 antibody with an unaltered glycosylation configuration) in a site-specific and stoichiometric fashion. Conjugation is accomplished either by using a wildtype transglutaminase under a specific reaction condition to attach the conjugate moiety (e.g., drug) to the anti-TROP2 antibody and/or by using an engineered transglutaminase that is specifically designed to carry out site-specific conjugation at an endogenous glutamine residue in the Fc region of the anti-TROP2 antibody. Such methods allow for the production of a homogeneous site-specific and stoichiometric anti-TROP2 antibody drug conjugate which would offer superior pharmacokinetic profile, broad therapeutic index, and optimal potency. Moreover, such methods allow conjugation of a drug to an intact anti-TROP2 antibody without introducing mutations and/or deglycosylating the antibody, thus minimizing immunogenicity that may result from introducing mutations into the antibody Fc region. As the glycans on the intact anti-TROP2 antibody, when present, protect the antibody from degradation, anti-TROP2 antibody drug conjugates produced according to a method described in WO 2015/191883 may also exhibit greater stability (e.g., longer serum half-life) as compared to an anti-TROP2 antibody drug conjugate produced using another method.

Methods of Treatment

An anti-TROP2 antibody drug conjugate (i.e., an anti-TROP2 ADC or simply "ADC") described herein may be administered to subjects (e.g., mammals such as humans) to treat or delay progression of a disease or disorder involving abnormal TROP2 activity or expression, including, for example, solid tumor, or cancer, such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc. In certain embodiments, provided is an anti-TROP2 ADC described herein for use in the manufacture of a medicament for the treatment of solid tumor or cancer solid tumor or cancer (e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) in a subject (such as a mammal, e.g., a human). In certain embodiments, provided is an anti-TROP2 ADC described herein for use in treating solid tumor or cancer (e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) in a subject (such as a mammal, e.g., a human). In certain embodiments, provided is a pharmaceutical composition comprising an anti-TROP2 ADC described herein for use in treating solid tumor or cancer (e.g., breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) in a subject (such as a mammal, e.g., a human). In some embodiments, TROP2-expressing tumors are treated.

In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a TROP2-expressing tumor (such as solid tumor) or cancer (such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.). In certain embodiments, the subject has been diagnosed with a TROP2-expressing tumor (such as solid tumor) or cancer (such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) and/or a disease associated with abnormal TROP2 expression or activity.

In certain embodiments, the subject to whom an anti-TROP2 ADC described herein is administered relapsed following treatment with sacituzumab govitecan (IMMU-132) or its biosimilar. In certain embodiments, the subject to whom an anti-TROP2 ADC described herein is administered has progressed on sacituzumab govitecan (IMMU-132) or its biosimilar. In certain embodiments, the subject to whom anti-TROP2 ADC described herein is administered is refractory to sacituzumab govitecan (IMMU-132) or its biosimilar. Further details regarding sacituzumab govitecan (IMMU-132) are provided in, e.g., Cardillo et al. (2015) *Bioconjug Chem.* 26(5): 919-31. In certain embodiments, the subject to whom an anti-TROP2 ADC described herein is administered relapsed following treatment with DS-1062a or its biosimilar. In certain embodiments, the subject to whom an anti-TROP2 ADC described herein is administered has progressed on DS-1062a or its biosimilar. In certain embodiments, the subject to whom an anti-TROP2 ADC described herein is administered is refractory to DS-1062a or its biosimilar. Further details regarding DS-1062a are provided in US 2018/0094073.

Many diagnostic methods for TROP2-expressing tumors (such as solid tumor) or cancer (such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) or other disease associated with abnormal TROP2 activity and the clinical delineation of those diseases are known in the art. Such methods include, but are not limited to, e.g., immunohistochemistry, PCR, fluorescent in situ hybridization (FISH).

An anti-TROP2 ADC described herein may be administered using any suitable route including, e.g., intravenous, intramuscular, or subcutaneous. In some embodiments, anti-TROP2 ADC described herein is administered in combination with a second, third, or fourth agent (including, e.g., an antineoplastic agent, a growth inhibitory agent, a cytotoxic agent, or a chemotherapeutic agent) to treat the diseases or disorders associated with abnormal TROP2 activity. Such agents include, but are not limited to, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4 (infusional fluorouracil, leucovorin, and oxaliplatin, afatinib, gemcitabine, capecitabine, pemetrexed, tivantinib, everolimus, CpG-ODN, rapamycin, eribulin, vinorelbine, lenalidomide, vemurafenib, endostatin, lapatinib, PX-866, Imprime PGG, and irlotinib. In some embodiments, an anti-TROP2 antibody provided herein (or an antigen-binding fragment thereof) is conjugated to an antineoplastic agent, a growth inhibitory agent, a cytotoxic agent, or a chemotherapeutic agent.

In certain embodiments, an anti-TROP2 ADC provided herein is administered in combination with one or more additional therapies, such as radiation therapy, surgery, chemotherapy, and/or targeted therapy. In certain embodiments, an anti-TROP2 ADC provided herein is administered in combination with chemotherapy.

Depending on the indication to be treated and factors relevant to the dosing that a physician of skill in the field would be familiar with, the antibodies provided herein will be administered at a dosage that is efficacious for the treatment of that indication while minimizing toxicity and side effects.

Therapeutic or prophylactic efficacy can be monitored by periodic assessment of subjects receiving treatment. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of an anti-TROP2 ADC provided herein, by multiple bolus administrations of an anti-TROP2 ADC provided herein provided herein, or by continuous infusion administration of an anti-TROP2 ADC provided herein provided herein.

Cancer treatments can be evaluated by, e.g., but not limited to, tumor regression, tumor weight or size shrinkage, time to progression, rate of remission, duration of survival, progression free survival, overall response rate, overall survival, duration of response, disease control rate, clinical benefit rate, quality of life, amount or level of TROP2 expression, and/or level of TROP2 activity. Approaches to determining efficacy of the therapy can be employed, including for example, measurement of response through, e.g., RECIST (Response Evaluation in Solid Tumors) criteria (see, e.g., Eisenhauer et al. (2009) "New response evaluation in solid tumors: Revised RECIST guideline (version 1.1)." *Eur J. Cancer.* 45: 228-247.

Pharmaceutical Formulations

The anti-TROP2 antibody drug conjugates provided herein provided herein can be formulated with pharmaceutically acceptable carriers or excipients so that they are suitable for administration to a subject in need thereof (e.g., a mammal such as a human). Suitable formulations of the antibodies are obtained by mixing an antibody (or fragment thereof) having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Pharmaceutically acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The anti-TROP2 antibody drug conjugates provided herein can also be formulated as immunoliposomes. Liposomes containing the antibody are prepared by methods known in the art, such as described in Epstein et al., *PNAS USA,* 82: 3688 (1985); Hwang et al., *PNAS USA,* 77: 4030

(1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. An anti-neoplastic agent, a growth inhibitory agent, or a chemotherapeutic agent (such as doxorubicin) is optionally also contained within the liposome. See, Gabizon et al., *J. National Cancer Inst.,* 81(19): 1484 (1989).

A pharmaceutical formulation comprising an anti-TROP2 ADC provided herein may also contain more than one active compound as necessary for the particular indication being treated, preferably those with complementary activities that do not adversely affect each other. For example, it may be desirable to provide an anti-neoplastic agent, a growth inhibitory agent, a cytotoxic agent, or a chemotherapeutic agent in addition to an anti-TROP2 ADC provided herein. Such molecules are suitably present in combination in amounts that are effective for the purpose intended. The effective amount of such other agents depends on the amount of antibody present in the formulation, the type of disease or disorder or treatment, and other factors discussed above. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

In some embodiments, an antibody of the present disclosure is lyophilized. Such lyophilized formulations may be reconstituted with a suitable diluent to a high protein concentration, and the reconstituted formulation may be administered to a mammal (such as a human).

In certain embodiments, the pharmaceutical formulations to be used for in vivo administration are sterile. This is readily accomplished by, e.g., filtering a solution comprising an anti-TROP2 ADC provided herein through sterile filtration membranes.

Methods of Diagnosis and Imaging Using Anti-TROP2 Antibodies

Labeled anti-TROP2 antibodies, fragments thereof, and derivatives and analogs thereof, which specifically bind to a TROP2 polypeptide can be used for diagnostic purposes to detect, diagnose, or monitor diseases and/or disorders associated with the expression, aberrant expression and/or activity of TROP2. For example, the anti-TROP2 antibodies (or fragments thereof) provided herein can be used in in situ, in vivo, ex vivo, and in vitro diagnostic assays or imaging assays. Methods for detecting expression of a TROP polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression. Such assays can be performed in vivo or ex vivo, e.g., using a sample obtained from a patient.

Also provided herein are methods of diagnosing a disease or disorder associated with expression or aberrant expression of TROP2 in an animal (e.g., a mammal such as a human). In some embodiments, the methods comprise detecting TROP2 polypeptides in the mammal. In certain embodiments, diagnosis comprises: (a) administering an effective amount of a labeled anti-TROP2 antibody (or fragment thereof) to a mammal (b) waiting for an interval of time following the administration step to permit the labeled anti-TROP2 antibody (or fragment thereof) to preferentially concentrate at sites in the subject where TROP2 is expressed (and/or for unbound labeled molecule to be cleared to background level); (d) detecting an amount or level of labeled anti-TROP2 antibody in the subject, and (e) comparing the amount or level of labeled anti-TROP2 antibody in the subject to a level or amount of anti-TROP2 antibody in a healthy control subject. If the amount or level of the labeled anti-TROP2 antibody in the subject exceeds the amount or level of anti-TROP2 antibody in a healthy control subject, this may indicate that the subject has a disease or disorder associated with expression or aberrant expression of TROP2.

Anti-TROP2 antibodies (or fragments thereof) provided herein can be used to assay amounts or levels of TROP2 in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other antibody-based methods useful for detecting TROP2 expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}I$, $^{125}I$, $^{123}I$, $^{121}I$) carbon ($^{14}C$), sulfur $^{35}S$), tritium ($^{3}H$), indium ($^{115m}In$, $^{113m}In$, $^{112}In$, $^{111}In$), and technetium ($^{99}Tc$, $^{99m}Tc$), thallium $^{201}Ti$), gallium ($^{68}Ga$, $^{67}Ga$), palladium ($^{103}Pd$), molybdenum ($^{99}Mo$), xenon ($^{133}Xe$), fluorine ($^{18}F$) $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{97}Ru$; luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

In some embodiments, TROP2 overexpression is measured by determining an amount of shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the can be evaluated, e.g., by external scanning for radioactivity or by analyzing a sample (e.g., a biopsy or other biological sample) taken from a mammal previously exposed to the antibody.

Articles of Manufacture and Kits

Provided is an article of manufacture comprising materials useful for the treatment of TROP2-expressing tumor (such as solid tumor) or cancer, such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc. In certain embodiments, the article of manufacture or kit comprises a container containing one or more of the anti-TROP2 antibody drug conjugates or the compositions described herein. In certain embodiments, the article of manufacture or kit comprises a container containing nucleic acids(s) encoding one (or more) of the anti-TROP2 antibodies or the compositions described herein. In some embodiments, the kit includes a cell of cell line that produces an anti-TROP2 antibody as described herein. In some embodiments, the kit includes one or more positive controls, for example TROP2 (or fragments thereof) or $TROP2^{+}$ cells. In some embodiments, the kit includes negative controls, for example a surface or solution that is substantially free of TROP2.

In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing TROP2-expressing tumor (such as solid tumor) or cancer (e.g. breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.) and may have a sterile access port (for example the container may be an intravenous solution bag or a vial having a stopper pierceable by a hypodermic injection needle). At least one agent in the composition is an anti-TROP2 antibody drug conjugate described herein. The label or package insert indicates that the composition is used for treating a TROP2-expressing tumor (such as solid tumor) or cancer (such as breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, and uterine cancer, etc.).

Moreover, the article of manufacture or kit may comprise (a) a first container with a composition contained therein, wherein the composition comprises an anti-TROP2 antibody drug conjugate described herein; and (b) a second container with a composition contained therein, wherein the composition comprises a further cytotoxic or otherwise therapeutic agent. In some embodiments, the therapeutic agent is an immunotherapeutic agent, as described herein. Additionally, the article of manufacture may further comprise an additional container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of TROP2 in patients, optionally in combination with the articles of manufacture. For isolation and purification of TROP2, the kit can contain an anti-TROP2 antibody (or fragment thereof) provided herein coupled to beads (e.g., sepharose beads). Kits can be provided which contain the antibodies (or fragments thereof) for detection and quantitation of TROP2 in vitro, e.g., in an ELISA or a Western blot. As with the article of manufacture, the kit comprises a container and a label or package insert on or associated with the container. For example, the container holds a composition comprising at least one anti-TROP2 antibody provided herein. Additional containers may be included that contain, e.g., diluents and buffers, control antibodies. The label or package insert may provide a description of the composition as well as instructions for the intended in vitro or diagnostic use.

EXAMPLES

Example 1A: Generation and Characterization of Anti-TROP2 Antibodies

Mouse anti-human TROP2 antibodies were obtained by immunizing mice with human TROP2, collecting splenocytes from immunized mice, and generating hybridomas. Clones that exhibited high affinity and potency for human TROP2 were selected for sequencing. The amino acid sequences of the heavy chain variable domains (VH) and light chain variable domains (VL) of anti-TROP2 antibodies 1B3, 15D9, 15A10, 7B6, and 17D1 are provided below:

| | VH SEQUENCES |
|---|---|
| 1B3 | QVQLQQSGAE LVRPGVSVKI SCKGS**GYTFT** **DYSIN**WVKQS HAKSLE**WIGV** **ISTYYGDASY** **NQKF**KGKATM TVDKSSSTAY MELARLTSED SAIYYC**ARYG** **DGYNQFDY**WG QGTTLTVSS (SEQ ID NO: 22) |
| 15D9 | QVQLQQSGAE LVRPGVSVKI SCKGS**GYTFT** **DYSIH**WVKQS HAKSLE**WIGV** **ISSYYGDATY** **NQKF**KGKATM TVDKSSSTAY MELARLTSED SAIYYC**ALLG** **AYNYFDY**WGQ GTTLTVSS (SEQ ID NO: 24) |
| 15A10 | EVQLEQSGPG LVQPSQSLSI TCTVS**GFSLT** **RYGVH**WVRQS PGRSLE**WLGV** **IWSGGNTDYN** **AAF**ISRLTIT KDNSKSQVFF KMNSLQPNDT GVYYC**AREDR** **YVGEFAY**WGQ GTLVTVSA (SEQ ID NO: 23) |
| 17B6 | QVQLQQSGAE LVRPGVSVKI SCKGS**GYTFT** **DYGMN**WVKQS HAKSLE**WIGV** **ISTFYGDANY** **NQKF**KGKATM TVDKSSSTAY MELARLTSED SAIYYC**ARRG** **NYDSMDY**WGQ GTSVTVSS (SEQ ID NO: 26) |
| 17D1 | QVQLQQSGAE LVRPGVSVKI SCKGS**GYTFT** **DYSIH**WVKQS HAKSLE**WIGL** **ISTYYGDATY** **TQKF**KGKATM TVDKSSSTAY MELARLTSED SAIYYC**ALLG** **AYNYFDY**WGQ GTTLTVSS (SEQ ID NO: 25) |
| | VL SEQUENCES |
| 1B3 | DIVLTQSPAS LAVSLGQRAT ISCRVS**ESVD** **SYGNNFMH**WY QQKPGQPPK**L** **LIYRASNLES** GVPARFSGSG SGTDFTLTIN PMEADDVATY YC**QQSYEDPY** **T**FGGGTKLEI K (SEQ ID NO: 27) |

-continued

| | |
|---|---|
| 15D9 | DIVLTQSPAS LAVSLGQRAT ISCRAS**ESVD SYGNSFMH**WY QQKPGQPPK**L LVYRASNLES** GIPARFSGSG SRTDFTLTIN PVEADDVATY YC**QQSYEDPP T**FGGGTKLEI K (SEQ ID NO: 29) |
| 15A10 | DIVLTQSTAS LAVSLGQRAT ISCRAS**ESVD SYGNSFIH**WY QQKPGQPPK**L LIYRASNLES** GIPARFSGSG SRTDFTLTIN PVEADDVATY YC**QQSNEDPR T**FGGGTKLEI K (SEQ ID NO: 28) |
| 17B6 | DIVLTQSPVF LAVSLGQRAT ISCRAS**ESVD SYGNSFMH**WY QQKPGQPPK**L LIYRASNLES** GIPARFSGSG SRTDFTLTIN PVEADDVETY YC**QQSYEDPP T**FGGGTKLEI E (SEQ ID NO: 31) |
| 17D1 | DIVLTQSPAS LAVSLGQRAT ISCRAS**ESVD SYGNSFMH**WY QQKPGQPPK**L LVYRASNLES** GIPARFSGSG SRTDFTLTIN PVEADDIATY YC**QQSYEDPP T**FGGGTKLEI K (SEQ ID NO: 30) |

FACS experiments were performed to verify that antibodies 1B3, 15D9, 15A10, 17B6, and 17D1 were internalized by SKBR3 cells. SKBR3 is a TROP2-expressing human breast carcinoma cell line. Briefly, $1.2\times10^5$ SKBR3 cells were seeded into each 12-well plates and cultured overnight. 300 μL of 20 nM control antibody, 1B3, 15D9, 15A10, 17B6, or 17D1 (in DMEM-10) were mixed with 300 μL 60 nM pHAb-labelled secondary antibody for 15 minutes at room temperature in the dark. The labeled antibodies mixtures were added to the SKBR3 cells and incubated overnight. Following overnight incubation, the SKBR3 cells were trypsinized, washed twice with 1% BSA/PBS, and analyzed via flow cytometry. See FIGS. 1A-1F. An overlap peak was observed with human IgG control and unlabeled cells (FIG. 1A), indicating that the control IgG was not internalized by the SKBR3 cells. No overlap peaks were observed for 1B3, 15D9, 15A10, 17B6, or 17D1, indicating that each of these anti-TROP2 antibodies was internalized by SKBR3 cells.

Example 1B. Characterization of Humanized Anti-Trophoblast Cell Surface Antigen 2 (TROP2) Antibodies The antibodies described in Example 1A were humanized using methods known in the art. The amino acid sequences of the humanized anti-TROP2 antibody heavy chains and light chains are provided in Table 7 below.

TABLE 7

| | |
|---|---|
| HC1 | QVQLVQSGAEVKKPGASVKVSCKASGYTFTDYSINWVRQAPGQGL EWMGVISTYYGDASYNQKFKGRVTMTTDTSTSTAYMELRSLRSDD TAVYYCARYGDGYNQFDYWGQGTMVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 52) |
| HC2 | QVQLVQSGAEVKKPGASVKVSCKASGYTFTDYSINWVRQAPGQGL EWMGVISTYYGDASYNQKFKGRVTMTRDTSTSTVYMELSSLRSED TAVYYCARYGDGYNQFDYWGQGTLVTVSSASTKGPSVFPLAPSSK |

TABLE 7-continued

| | |
|---|---|
| | STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 53) |
| HC3 | QVQLVQSGAEVKKPGASVKVSCKASGYTFTDYSINWVRQAPGQRL EWMGVISTYYGDASYNQKFKGRVTITRDTSASTAYMELSSLRSED TAVYYCARYGDGYNQFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 54) |
| HC4 | QVQLVQSGAEVKKPGSSVKVSCKASGYTFTDYSINWVRQAPGQGL EWMGVISTYYGDASYNQKFKGRVTITADESTSTAYMELSSLRSED TAVYYCARYGDGYNQFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 55) |
| HC5 | EVQLVQSGAEVKKPGESLKISCKGSGYTFTDYSINWVRQMPGKGL EWMGVISTYYGDASYNQKFKGQVTISADKSISTAYLQWSSLKASD TAMYYCARYGDGYNQFDYWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKT HTCPPCPAPELLGGPSVFLFPPKPKDTLMISRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 56) |
| LC1 | DIVMTQSPDSLAVSLGERATINCRVSESVDSYGNNFMHWYQQKPG QPPKLLIYRASNLESGVPDRFSGSGSGTDFTLTISSLQAEDVAVY YCQQSYEDPYTFGQGTKLEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC (SEQ ID NO: 58) |
| LC2 | DVVMTQSPLSLPVTLGQPASISCRVSESVDSYGNNFMHWFQQRPG QSPRRLIYRASNLESGVPDRFSGSGSGTDFTLKISRVEAEDVGVY YCQQSYEDPYTEGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC (SEQ ID NO: 59) |
| LC3 | DIVMTQSPLSLPVTPGEPASISCRVSESVDSYGNNFMHWYLQKPG QSPQLLIYRASNLESGVPDRFSGSGSGTDFTLKISRVEAEDVGVY YCQQSYEDPYTEGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC (SEQ ID NO: 60) |
| LC4 | EIVLTQSPATLSLSPGERATLSCRVSESVDSYGNNFMHWYQQKPG QAPRLLIYRASNLESGIPARFSGSGSGTDFTLTISSLEPEDFAVY YCQQSYEDPYTEGGGTKVEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC (SEQ ID NO: 61) |
| LC5 | DIQMTQSPSSLSASVGDRVTITCRVSESVDSYGNNFMHWYQQKPG KAPKLLIYRASNLESGVPSRFSGSGSGTDFTFTISSLQPEDIATY YCQQSYEDPYTFGGGTKLEIKRTVAAPSVFIFPPSDEQLKSGTAS VVCLLNNFYPREAKVQWKVDNALQSGNSQESVTEQDSKDSTYSLS STLTLSKADYEKHKVYACEVTHQGLSSPVTKSFNRGEC (SEQ ID NO: 62) |

The theoretical isoelectric points (pI) and theoretical molecular weights of anti-TROP2 antibodies comprising HC/LC pairs based on the sequences in Table 7 are shown in Table 8A below:

TABLE 8A

| Heavy Chain/ Light Chain* | Theoretical Isoelectric Point (pI) | Theoretical Molecular Weight (MW) |
|---|---|---|
| HC1/LC1 | 6.95 | 146616.28 |
| HC1/LC2 | 7.90 | 146576.33 |
| HC1/LC3 | 6.95 | 146378.12 |
| HC1/LC4 | 7.28 | 146446.13 |
| HC1/LC5 | 7.90 | 146470.09 |
| HC2/LC1 | 6.95 | 146636.32 |
| HC2/LC2 | 7.90 | 146596.37 |
| HC2/LC3 | 6.95 | 146398.16 |
| HC2/LC4 | 7.28 | 146466.17 |
| HC2/LC5 | 7.90 | 146490.23 |
| HC3/LC1 | 7.28 | 146682.37 |
| HC3/LC2 | 8.09 | 146642.41 |
| HC3/LC3 | 7.28 | 146444.21 |
| HC3/LC4 | 7.63 | 146512.21 |
| HC3/LC5 | 8.08 | 146536.18 |
| HC4/LC1 | 6.51 | 146461.95 |
| HC4/LC2 | 7.28 | 146421.99 |
| HC4/LC3 | 6.51 | 146223.79 |
| HC4/LC4 | 6.70 | 146291.80 |
| HC4/LC5 | 7.28 | 146315.76 |
| HC5/LC1 | 6.95 | 146634.51 |
| HC5/LC2 | 7.91 | 146594.56 |
| HC5/LC3 | 6.96 | 146396.35 |
| HC5/LC4 | 7.30 | 146464.36 |
| HC5/LC5 | 7.90 | 146488.32 |

*The amino acid sequenecs of each heavy chain and light chain are provided in Table 7

Surface plasmon resonance (SPR) experiments were performed to determine the kinetics and affinities of certain antibodies shown in Table 8A. The amino acid sequences of each antibody are shown in Table 7. The results are shown in Table 8B below.

TABLE 8B

Affinities and Kinetics of Anti-human TROP2 Antibodies

| Antibody | Analyte | $k_a$ (1/Ms) | $k_d$ (1/s) | $K_D$ (M) | Rmax | Chi$^2$ (RU$^2$) |
|---|---|---|---|---|---|---|
| DP002-HC1LC1 | TROP2 | 1.97E+06 | 1.30E−04 | 6.62E−11 | 52.4 | 4.18E−02 |
| DP002-HC1LC5 | TROP2 | 1.81E+06 | 1.04E−04 | 5.77E−11 | 51.7 | 3.78E−02 |
| DP002-HC4LC5 | TROP2 | 2.20E+06 | 4.05E−05 | 1.84E−11 | 50.7 | 1.01E−01 |
| Control* | TROP2 | 5.11E+05 | 2.04E−04 | 4.00E−10 | 50.7 | 1.65E−02 |

*The control antibody is a biosimilar of the anti-TROP2 antibody sacituzumab.

Additional SPR experiments were performed to rank the affinities of the anti-TROP2 antibodies listed in Table 8A. The results are shown in Table 8C below:

TABLE 8C

Kinetic Data of Humanized anti-TROP2 Antibodies to human TROP2

| ANTIBODY | Ka (1/Ms) | Kd (1/s) | $K_D$ (M) | Rmax (RU) |
|---|---|---|---|---|
| HC2 + LC1 | $1.54 \times 10^{6}$ | $5.78 \times 10^{-5}$ | $3.75 \times 10^{-11}$ | 65.3 |
| HC4 + LC1 | $1.69 \times 10^{6}$ | $7.74 \times 10^{-5}$ | $4.57 \times 10^{-11}$ | 56.6 |
| HC2 + LC5 | $1.42 \times 10^{6}$ | $7.38 \times 10^{-5}$ | $5.20 \times 10^{-11}$ | 65.6 |
| HC4 + LC4 | $1.71 \times 10^{6}$ | $8.88 \times 10^{-5}$ | $5.20 \times 10^{-11}$ | 38.6 |
| HC1 + LC1 | $1.63 \times 10^{6}$ | $1.05 \times 10^{-4}$ | $6.45 \times 10^{-11}$ | 48.4 |
| HC3 + LC1 | $1.65 \times 10^{6}$ | $1.10 \times 10^{-4}$ | $6.70 \times 10^{-11}$ | 53.3 |
| HC4 + LC5 | $1.72 \times 10^{6}$ | $1.38 \times 10^{-4}$ | $8.01 \times 10^{-11}$ | 49.9 |
| HC1 + LC4 | $1.38 \times 10^{6}$ | $1.26 \times 10^{-4}$ | $9.11 \times 10^{-11}$ | 45 |
| HC4 + LC3 | $1.95 \times 10^{6}$ | $1.78 \times 10^{-4}$ | $9.16 \times 10^{-11}$ | 29.6 |
| HC2 + LC4 | $1.46 \times 10^{6}$ | $1.40 \times 10^{-4}$ | $9.57 \times 10^{-11}$ | 41.3 |
| HC2 + LC3 | $1.36 \times 10^{6}$ | $1.41 \times 10^{-4}$ | $1.04 \times 10^{-10}$ | 35.4 |
| HC1 + LC5 | $1.39 \times 10^{6}$ | $1.49 \times 10^{-4}$ | $1.07 \times 10^{-10}$ | 52.5 |
| HC3 + LC3 | $1.49 \times 10^{6}$ | $1.59 \times 10^{-4}$ | $1.07 \times 10^{-10}$ | 35.2 |
| HC3 + LC5 | $1.32 \times 10^{6}$ | $1.51 \times 10^{-4}$ | $1.14 \times 10^{-10}$ | 62.8 |
| HC1 + LC3 | $1.62 \times 10^{6}$ | $1.96 \times 10^{-4}$ | $1.21 \times 10^{-10}$ | 35.1 |
| HC3 + LC4 | $1.37 \times 10^{6}$ | $1.92 \times 10^{-4}$ | $1.40 \times 10^{-10}$ | 37.2 |
| HC5 + LC1 | $1.60 \times 10^{6}$ | $2.35 \times 10^{-4}$ | $1.47 \times 10^{-10}$ | 44.2 |
| HC5 + LC3 | $1.46 \times 10^{6}$ | $2.66 \times 10^{-4}$ | $1.82 \times 10^{-10}$ | 34.3 |
| HC5 + LC4 | $1.36 \times 10^{6}$ | $2.99 \times 10^{-4}$ | $2.20 \times 10^{-10}$ | 32.5 |
| HC5 + LC5 | $1.42 \times 10^{6}$ | $3.38 \times 10^{-4}$ | $2.38 \times 10^{-10}$ | 61.3 |
| DP002-hm1 R | $7.80 \times 10^{5}$ | $2.14 \times 10^{-4}$ | $2.75 \times 10^{-10}$ | 91 |
| HC5 + LC2 | $2.61 \times 10^{5}$ | $4.02 \times 10^{-4}$ | $1.54 \times 10^{-9}$ | 0.9 |
| HC1 + LC2 | $2.49 \times 10^{5}$ | $1.02 \times 10^{-3}$ | $4.09 \times 10^{-9}$ | 2 |
| HC4 + LC2 | $1.84 \times 10^{5}$ | $9.84 \times 10^{-4}$ | $5.34 \times 10^{-9}$ | 2.8 |
| HC3 + LC2 | $1.69 \times 10^{5}$ | $1.77 \times 10^{-3}$ | $1.04 \times 10^{-8}$ | 3.5 |
| HC2 + LC2 | $2.49 \times 10^{4}$ | $2.51 \times 10^{-2}$ | $8.65 \times 10^{-7}$ | 63.7 |
| Blank | $9.24 \times 10^{4}$ | $1.15 \times 10^{-3}$ | $1.24 \times 10^{-8}$ | 1.7 |

Example 2: In Vitro Cytotoxicity Assays Performed Using an Anti-TROP2 Ab-MMAE Antibody-Drug Conjugate (ADC)

DP002-HC1LC1-ADC is an antibody-drug conjugate comprising anti-TROP antibody DP002-HC1LC1, which comprises HC1 (SEQ ID NO: 52) and LC 1 (SEQ ID NO: 58), conjugated to monomethyl auristatin E (MMAE) at a drug-antibody ratio (DAR) of 2. A DP002-HC1LC1-ADC was prepared using a conjugation method described in WO 2015/191883. A series of in vitro cytotoxicity assays were performed to assess the ability of DP002-HC1LC1-ADC to inhibit the growth of the following TROP2 expressing cancer cell lines: HCC1954 (a human breast carcinoma cell line), BxPC-3 (a human pancreatic adenocarcinoma cell line), and NCI-N87 (a human gastric carcinoma cell line). Experiments using staurospirone, a positive apoptosis control, and anti-TROP2 antibody DP002-HC4LC5, which comprises HC4 (SEQ ID NO: 55) and LC5 (SEQ ID NO: 62), were performed in parallel.

As shown in Table 9A, treatment with staurospirone induced apoptosis greater than 93% of all three cell lines, whereas treatment with anti-TROP2 antibody HC4/LC5 showed little to no activity in any of the cell lines. DP002-HC1LC1-ADC demonstrated maximum growth inhibition of about 46% in NCI-N87 gastric cancer cells, about 57% in BxPC-2 pancreatic cancer cells, and about 69% in HCC1954 breast cancer cells.

TABLE 9A

Cytotoxic Activity of ADC-1 in TROP2-Expressing Human Cancer Cell Lines

| Cell Line | Curve | IC50 (nM) | Max % inhibition |
|---|---|---|---|
| | Staurosprione | | |
| HCC1954 | 1 | 21.69 | 95.12 |
| BxPC-3 | 13 | 5.37 | 98.02 |
| NCI-N87 | 16 | 9.31 | 93.44 |

TABLE 9A-continued

| Cytotoxic Activity of ADC-1 in TROP2-Expressing Human Cancer Cell Lines | | | |
|---|---|---|---|
| Cell Line | Curve | IC50 (nM) | Max % inhibition |
| | DP002HC4LC5 | | |
| HCC1954 | 2 | >100 | 2.28 |
| BxPC-3 | 14 | >100 | 2.95 |
| NCI-N87 | 17 | >100 | 7.07 |
| | DP002-HC1LC1-ADC | | |
| HCC1954 | 3 | 0.18 | 69.04 |
| BxPC-3 | 15 | 0.16 | 57.11 |
| NCI-N87 | 18 | 0.04 | 46.05 |

Additional in vitro cytotoxicity assays were performed to test the ability of DP002-HC1LC1-ADC to inhibit the growth of MDA-MB-468 (a TROP2$^+$ human breast adenocarcinoma cell line) and HCC38 (a TROP2$^+$ human mammary ductal carcinoma cell line). As shown in Table 9B, DP002-HC1LC1-ADC inhibited the growth of TROP2$^+$ MDA-MB-468 breast cancer cells by about 65%.

TABLE 9B

| Cytotoxic Activity of ADC-1 in Cancer Cell Lines | | | | | | |
|---|---|---|---|---|---|---|
| | Staurosprione | | DP002-HC1LC1 | | DP002-HC1LC1-ADC | |
| Cell Line | IC50 (nM) | Max % inhibition | IC50 (nM) | Max % inhibition | IC50 (nM) | Max % inhibition |
| MDA-MB-468 | 14.69 | 92.38 | >100 | 14.57 | 0.15 | 64.75 |
| HCC38 | 4.26 | 99.44 | >100 | 10.87 | >100 | 22.56 |

Example 3: Activity of Anti-TROP2-MMAE Antibody Drug Conjugates in a Mouse MDA-MB-468 Xenograft Model The efficacies of two anti-TROP2-MMAE antibody drug conjugates, DP002-HC1LC5-ADC (DAR ~2) and DP002-HC4LC5-ADC (DAR ~1.6-2.3), in inhibiting tumor growth in mice bearing human MDA-MB-468 breast adenocarcinoma tumor xenografts were tested. DP002-HC1LC5-ADC comprises an anti-TROP antibody that comprises HC 1 (SEQ ID NO: 52) and LC5 (SEQ ID NO: 62); DP002-HC4LC5-ADC comprises an anti-TROP antibody that comprises HC 4 (SEQ ID NO: 44) and LC5 (SEQ ID NO: 62). Briefly, 48 NOD/SCID mice (female, 6-8 weeks of age) were implanted with 0.1 ml MDA-MB-468 cells (lx $10^7$ cell/ml). When the tumors sizes reached above 181 $mm^3$ (34 days after tumor inoculation), the mice were sorted randomly into 7 groups (6 mice/group) and treated according to the schedule provided in Table 10 below:

TABLE 10

| Dose and Administration Schedule for Efficacy Studies in MDA-MB-468-Xenografted Mice | | | | | | | |
|---|---|---|---|---|---|---|---|
| Group | Drug | Mice | Dose (mg/kg) | Volume (ml/kg) | Route | Frequency | Duration of Treatment |
| 1 | Vehicle* | 6 | — | 10 | intravenous | Single dose on Day 0 | 8 weeks |
| 2 | Antibody control** | 6 | 4 | 10 | intravenous | Single dose on Day 0 | 6 weeks |
| 3 | DP002-HC1LC5-ADC | 6 | 1 | 10 | intravenous | Single dose on Day 0 | 6 weeks |
| 4 | DP002-HC1LC5-ADC | 6 | 4 | 10 | intravenous | Single dose on Day 0 | 8 weeks |
| 5 | DP002-HC4LC5-ADC | 6 | 1 | 10 | intravenous | Single dose on Day 0 | 6 weeks |
| 6 | DP002-HC4LC5-ADC | 6 | 4 | 10 | intravenous | Single dose on Day 0 | 8 weeks |
| 7 | Positive Control*** | 6 | 7.5 | 10 | intravenous | Single dose on each of Days 0, 4, 7, and 11 | 8 weeks |

*Vehicle = Sterile 1 x PBS, pH = 7.4.

**Control antibody was unconjugated DP002-HC4LC5

*** Positive control was a biosimilar of sacituzumab govetican.

The antibody control administered to the mice in Group 2 was DP002-HC4LC5. The positive control administered to the mice in Group 7 was a biosimilar of IMMU-132 (also known as sacituzumab govitecan). No obvious side effects were seen in any of the groups based on body weight, survival and gross observations.

Figure 2:
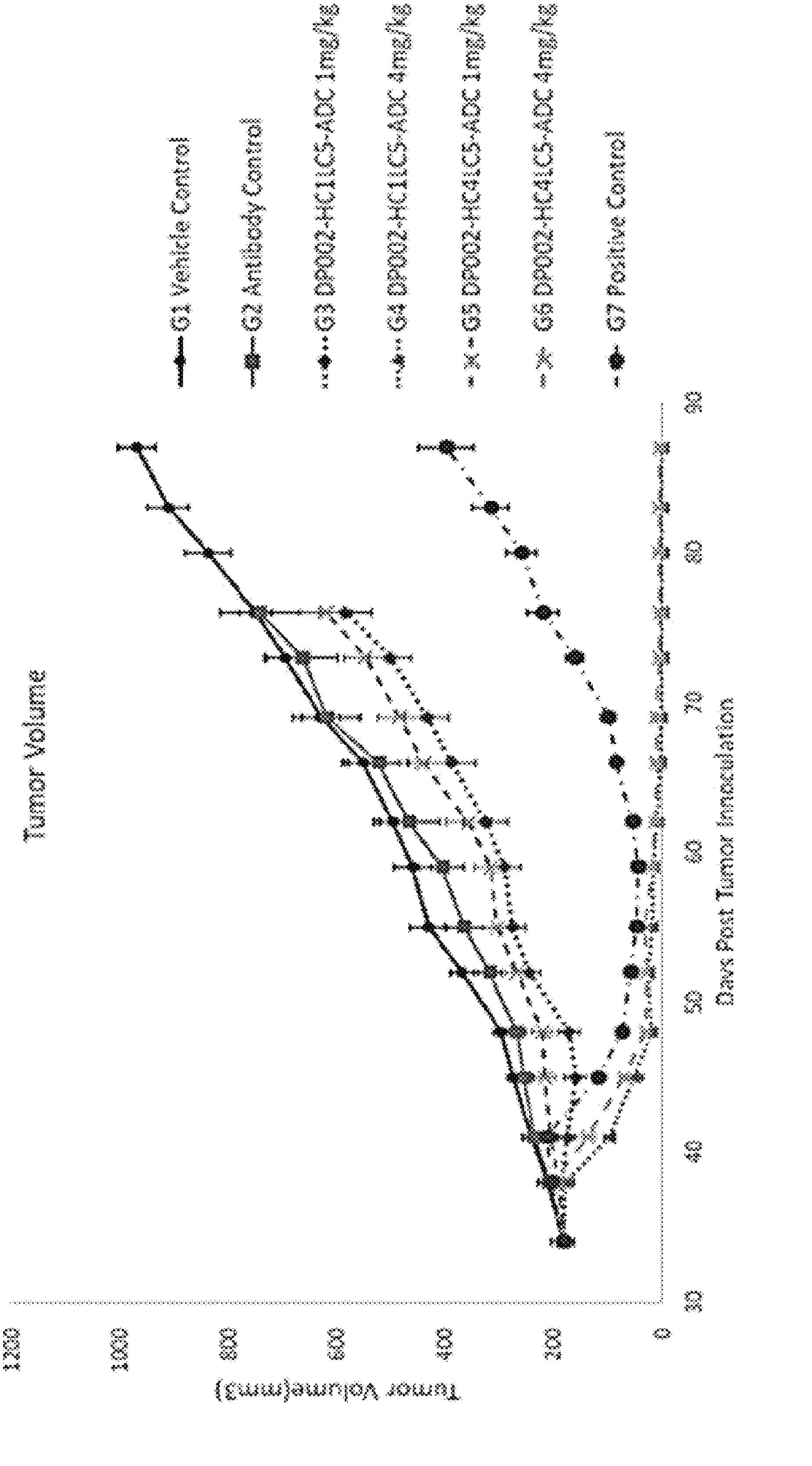
FIGS. 2 and 3 show the results of experiments that were performed to assess the efficacies of DP002-HC1LC5-ADC and DP002-HC4LC5-ADC in inhibiting tumor growth in mice bearing MDA-MB-468 human tumor xenografts.
Figure 3:
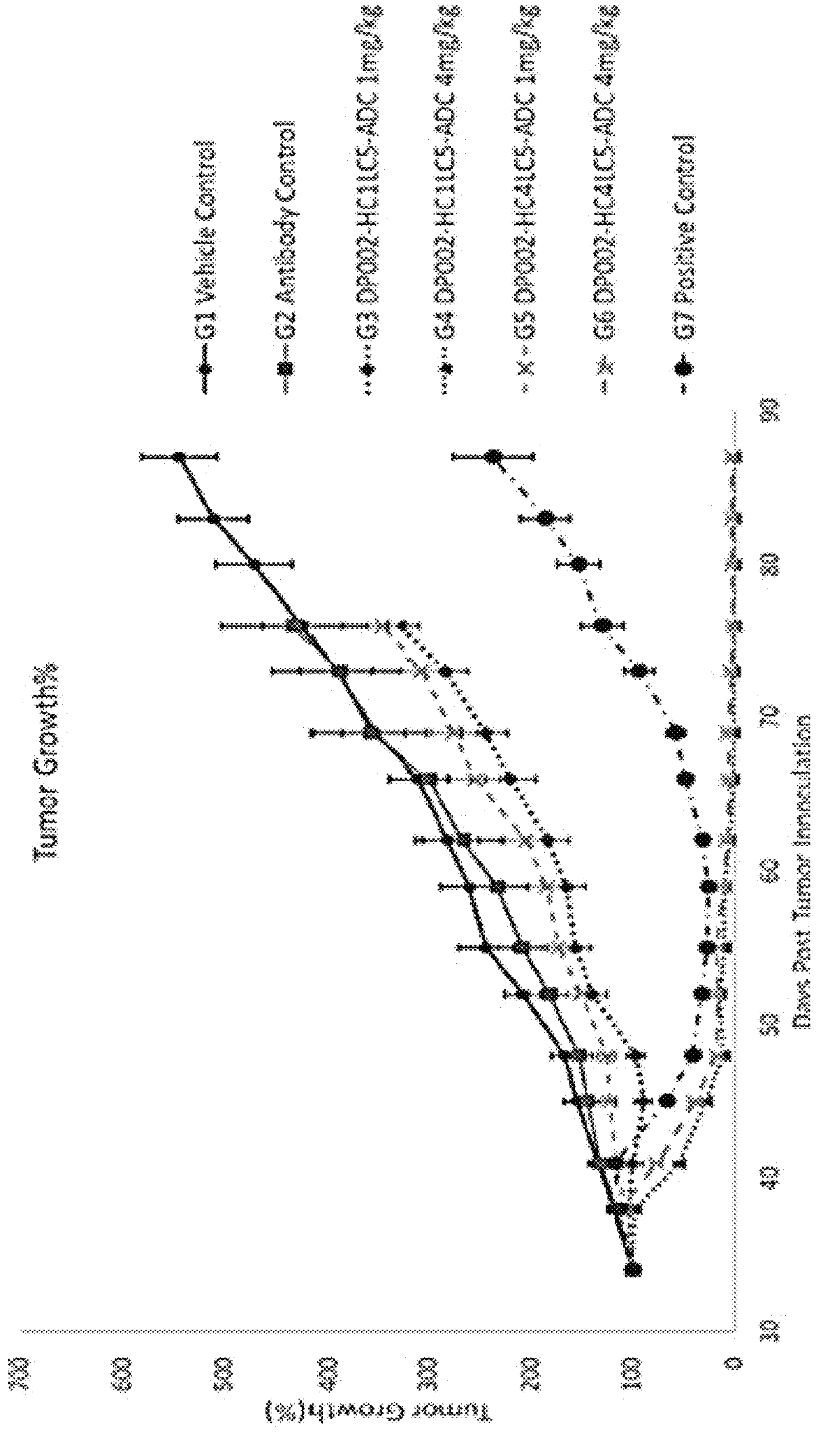

The results of the xenograft experiments are shown in Table 11 and in FIGS. 2 and 3.

TABLE 11

Antitumor Activities of Treatments Shown in Table 10

| Treatment Group | Tumor Size[a] ($mm^3$) at Day 42 | T/C (%)[b] | TGI (%)[c] | P-value[d] |
|---|---|---|---|---|
| 1 | 750 ± 31 | — | — | — |
| 2 | 742 ± 74 | 102 | −2% | ns |
| 3 | 583 ± 49 | 77 | 23 | ** |
| 4 | 0 ± 0 | 0 | 100 | **** |
| 5 | 620 ± 61 | 82 | 18 | ns |
| 6 | 4 ± 2 | 0 | 100 | **** |
| 7 | 219 ± 28 | 31 | 69 | **** |

[a]Mean ± standard error of mean (SEM);
[b]T/C = (tumor volume treated final/tumor volume treated initial)/(tumor volume Vehicle final/tumor volume Vehicle initial) * 100%;
[c]TGI = [1- (tumor volume treated final/tumor volume treated initial)/(tumor volume Vehicle final/tumor volume Vehicle initial)] * 100%;
[d]vs. Vehicle control, via Tukeys multiple comparisons test; P < 0.01, *P < 0.001, **P < 0.0001, ns: not significant As shown in Table 11 and FIGS. 2 and 3**, treatment with vehicle (Group 1) or antibody control (Group 2) did not have any effect on tumor growth. Similarly, treatment with an IgG-ADC control had no effect on tumor growth (data not shown). Mice treated with positive control (Group 7) demonstrated significant tumor growth inhibition (i.e., 69%). Tumor growth was inhibited in mice treated with 1 mg/kg DP002-HC1LC5-ADC (Group 3) or 1 mg/kg DP002-HC4LC5-ADC (Group 5) by 23% and 18%, respectively. Mice treated with 4 mg/kg DP002-HC1LC5-ADC (Group 4) or 4 mg/kg DP002-HC4LC5-ADC (Group 6) demonstrated complete tumor remission, i.e., an inhibition rate for tumor growth of 100%.

Groups 2, 3, and 5 were terminated on Day 42 post drug administration, and Groups 1, 4, 6, and 7 were monitored for an additional two weeks. The mean tumor volumes of mice in Group 1 (vehicle control) and Group 7 (positive control) reached 1069 $mm^3$ and 437 $mm^3$, respectively. By contrast, the tumors in mice in Groups 4 and 6 did not regrow. The average tumor volumes of mice in Group 4 (4 mg/kg DP002-HC1LC5-ADC) was 0 $mm^3$ on Day 56 following the initiation of treatment, and the average tumor volumes of mice in Group 6 (4 mg/kg DP002-HC4LC5-ADC) were 3 $mm^3$.

No obvious side effects were seen in the animals receiving DP002-HC1LC5-ADC or DP002-HC4LC5-ADC at either dose tested based on changes in body weight, survival and gross observations.

Example 4: Activity of Anti-TROP2-MMAE Antibody Drug Conjugate DP002-HC4LC5-ADC in a Mouse MDA-MB-468 Xenograft Model The anti-tumor activity of DP002-HC4LC5-ADC was evaluated as a single agent in female nude mice bearing xenografted MDA-MB-468 human breast adenocarcinoma tumors.

Each mouse was inoculated with $5\times10^6$ MDA-MB-468 tumor cells (in 0.1 mL, 1:1 with Matrigel) at the right flank by subcutaneous administration under sterile conditions. When the tumors reached a volume of ~150 $mm^3$, mice were randomized into one of 7 treatment groups (6 mice per group), as outlined in Table 12, and treatments began. All doses of DP002-HC4LC5-ADC were administered by intravenous injection via tail vein injection.

TABLE 12

Treatment Groups for MDA-MB-468 xenograft model

| Group | Animals | Treatment | Dose (mg/kg) | Injection Volume (mL/kg) | Concentration (mg/mL) | Route | Treatment Schedule |
|---|---|---|---|---|---|---|---|
| 1 | 6 | Vehicle (PBS) | (N/A) | 10 | (N/A) | IV | Once on Day 0 |
| 2 | 6 | DP002-HC4LC5 (Ab control) | 4 | 10 | 0.4 | IV | Once on Day 0 |
| 3 | 6 | DP002-HC4LC5-ADC | 1 | 10 | 0.1 | IV | Once on Day 0 |
| 4 | 6 | DP002-HC4LC5-ADC | 2 | 10 | 0.2 | IV | Once on Day 0 |
| 5 | 6 | DP002-HC4LC5-ADC | 4 | 10 | 0.4 | IV | Once on Day 0 |
| 6 | 6 | DP002-HC4LC5-ADC | 2<br>1 | 10<br>10 | 0.2<br>0.1 | IV<br>IV | Day 0<br>Day 7, 14 |
| 7 | 6 | DP002-HC4LC5-ADC | 1 | 10 | 0.1 | IV | Day 0, 7, 14, 21 |

All doses were administered via tail vein injection. Mice were dosed according to body weight using the most recent weight measurement.

Tumor size and animal body weight were measured twice per week. Clinical signs were recorded daily. Tumors were measured using a caliper in two dimensions (i.e., length (a) and width (b)), and tumor volumes were estimated from measurements of the two diameters of the individual tumors as follows: Tumor Volume ($mm^3$)=($a \times b^2$)/2.

The following criteria (humane endpoints) were used to determine whether animals were to be removed from study and euthanized:

1) Weight loss—animals were euthanized if they lost 20% of their body weight relative to the start of the study.
2) Tumor size—animals were euthanized if the tumor volume reached greater than 10% of animals body weight or 2000 $mm^3$.
3) Animal behavior—animals were euthanized if they demonstrated paralysis, dehydration, hypothermia, abnormal breathing, low activity level, obvious pain, general poor body condition, diarrhea, skin lesions and/or were not responsive to palliative treatment.
4) Tumor appearance—animals that developed of large or open tumor ulcerations were euthanized.

In the present study, all animals were euthanized on Day 84, unless the animal died at an earlier time point or was euthanized at an earlier time due to meeting one or more humane endpoints. On Day 70, four animals in Group 1 (vehicle) and four animals Group 2 (DP002 4 mg/kg) were euthanized due to open ulceration in the tumor according to the study protocol. On day 77, two animals in Group 3 (DP002-HC4LC5-ADC 1 mg/kg single dose), one animal in Group 4 (DP002-HC4LC5-ADC 2 mg/kg single dose), and one animal in Group 5 (DP002-HC4LC5-ADC DP002-HC4LC5-ADC 2 mg/kg on Day 0 plus DP002-HC4LC5-ADC 1 mg/kg on each of Days 7 and 14) were euthanized due to open ulceration in the tumor.

Average tumor growth curves for each treatment group were plotted with the observation time on the X-axis, and corresponding tumor volume (geometric mean) on the Y-axis. A two-tailed t-test was used to analyze the statistical significance of any differences between the treatment groups and the control group. Tumor Growth Inhibition (TGI) was calculated after each tumor volume measurement according to the formula: % TGI=(TVcn−TVtn)/TVcn×100, where TVtn and TVcn are the mean tumor Volume of treated and control groups, respectively. Body weight change (CBW %) was calculated after each body weight measurement according to the formula: CBW %=($BW_n$−$BW_0$)/$BW_0$×100, where $BW_n$ is the body weight at day n and $BW_0$ is the body weight at day 0 respectively.

Results

Administration of vehicle to the mice in Group 1 had no impact on animal growth. Group 1 mice continued to gain body weight throughout the treatment period. On Day 70, the average body weight of Group 1 mice increased 7.08% (or 1.37 g) compared to Day 0. On Day 84, the average body weight of Group 1 mice increased 10.69% (or 1.77 g) compared to Day 0. Similarly, the average body weight of Group 2 mice increased 9.31% (or 1.78 g) on Day 70, as compared to Day 0, and increased 17.79% (or 3.65 g) on Day 84, as compared to Day 0.

Figure 4:
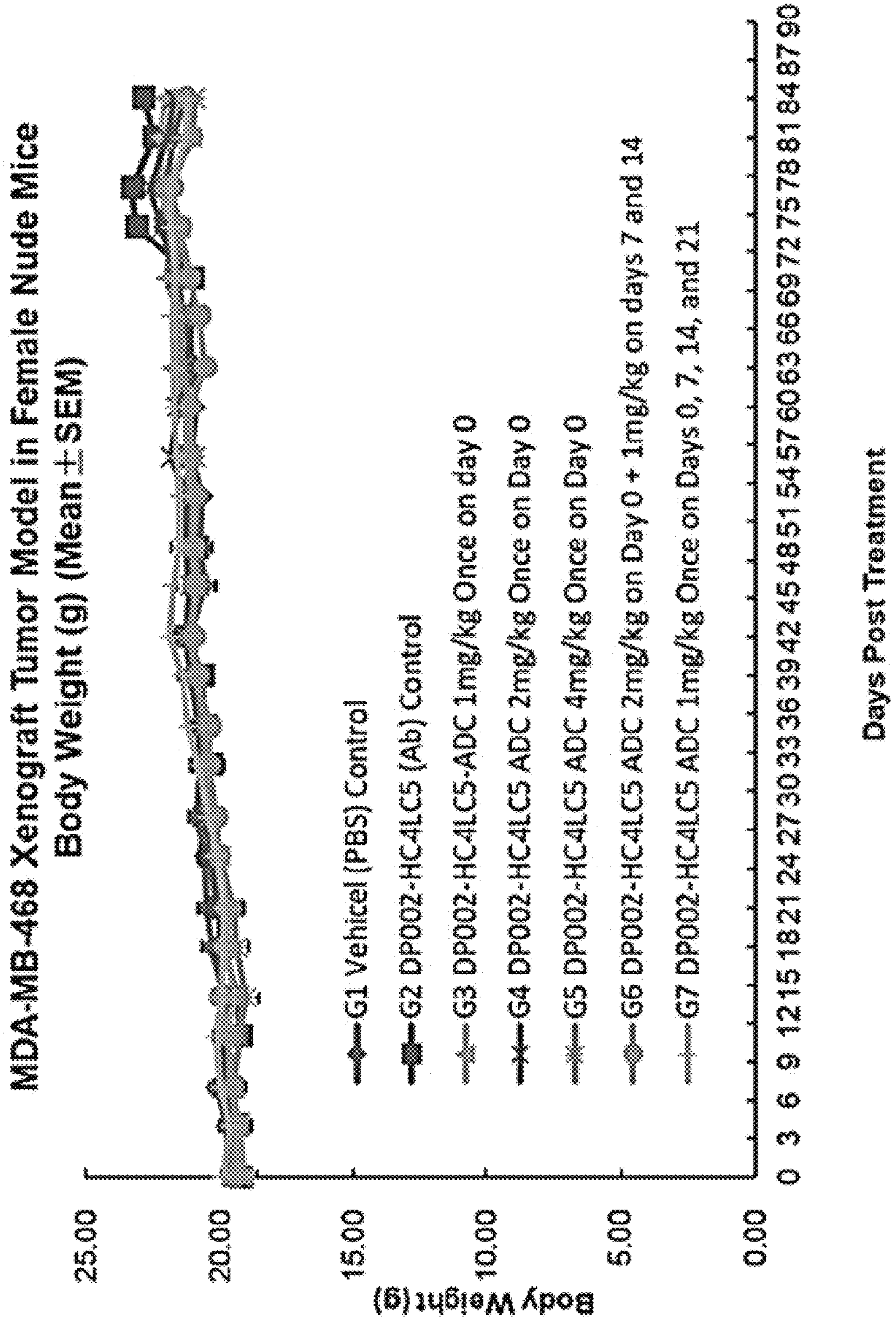
FIG. 4 shows the change in average body weight of mice in Treatment Groups 1-7 at timepoints following the start of treatment.

Animals in Groups 3, 4, 5, 6, and 7 also continued to gain body weight throughout the treatment period. On Day 70, the average body weight increased 15.09% (or 2.87 g) in Group 3 mice; 11.00% (or 2.14 g) in Group 4 mice; 10.87% (or 2.13 g) in Group 5 mice; 8.89% (or 1.72 g) in Group 6 mice; and 8.95% (or 1.76 g) in Group 7 mice, as compared to average body weight on Day 0. On Day 84, the average body weight increased 12.37% (or 2.92 g, n=4) in Group 3 mice; 10.84% (or 2.26 g, n=5) in Group 4 mice; 6.99% (or 1.37 g) in Group 5 mice; 10.24% (or 1.85 g, n=5) in Group 6 mice; and 6.66% (or 1.30) in Group 7 mice, as compared to average body weight on Day 0. Changes in average body weight in response to the various treatments are summarized in Table 13 and FIG. 4.

TABLE 13

Effects of Treatment with DP002-HC4LC5-ADC on Body Weight in MDA-MB-468 xenograft model

| Treatment | Body Weight (g, Mean ± SEM) | | | BWC* (%) | Drug-related |
|---|---|---|---|---|---|
| Group | Day 0 | Day 70 | Day 84 | Day 70 | Death |
| 1 | 19.60 ± 0.28 | 20.97 ± 0.39 | 21.37 ± 1.30 (N = 2) | 7.08% | 0 |
| 2 | 19.25 ± 0.31 | 21.03 ± 0.58 | 22.90 ± 0.70 (N = 2) | 9.31% | 0 |
| 3 | 19.14 ± 0.47 | 22.01 ± 0.50 | 22.06 ± 0.64 (N = 2) | 15.09% | 0 |
| 4 | 19.49 ± 0.33 | 21.63 ± 0.39 | 21.75 ± 0.55 (N = 2) | 11.00% | 0 |
| 5 | 19.59 ± 0.37 | 21.72 ± 0.44 | 20.96 ± 0.55 | 10.87% | 0 |
| 6 | 19.46 ± 0.34 | 21.18 ± 0.49 | 21.31 ± 0.46 (N = 2) | 8.89% | 0 |
| 7 | 19.94 ± 0.35 | 21.70 ± 0.30 | 21.24 ± 0.26 | 8.95% | 0 |

*BWC = body weight change

Figure 5A:
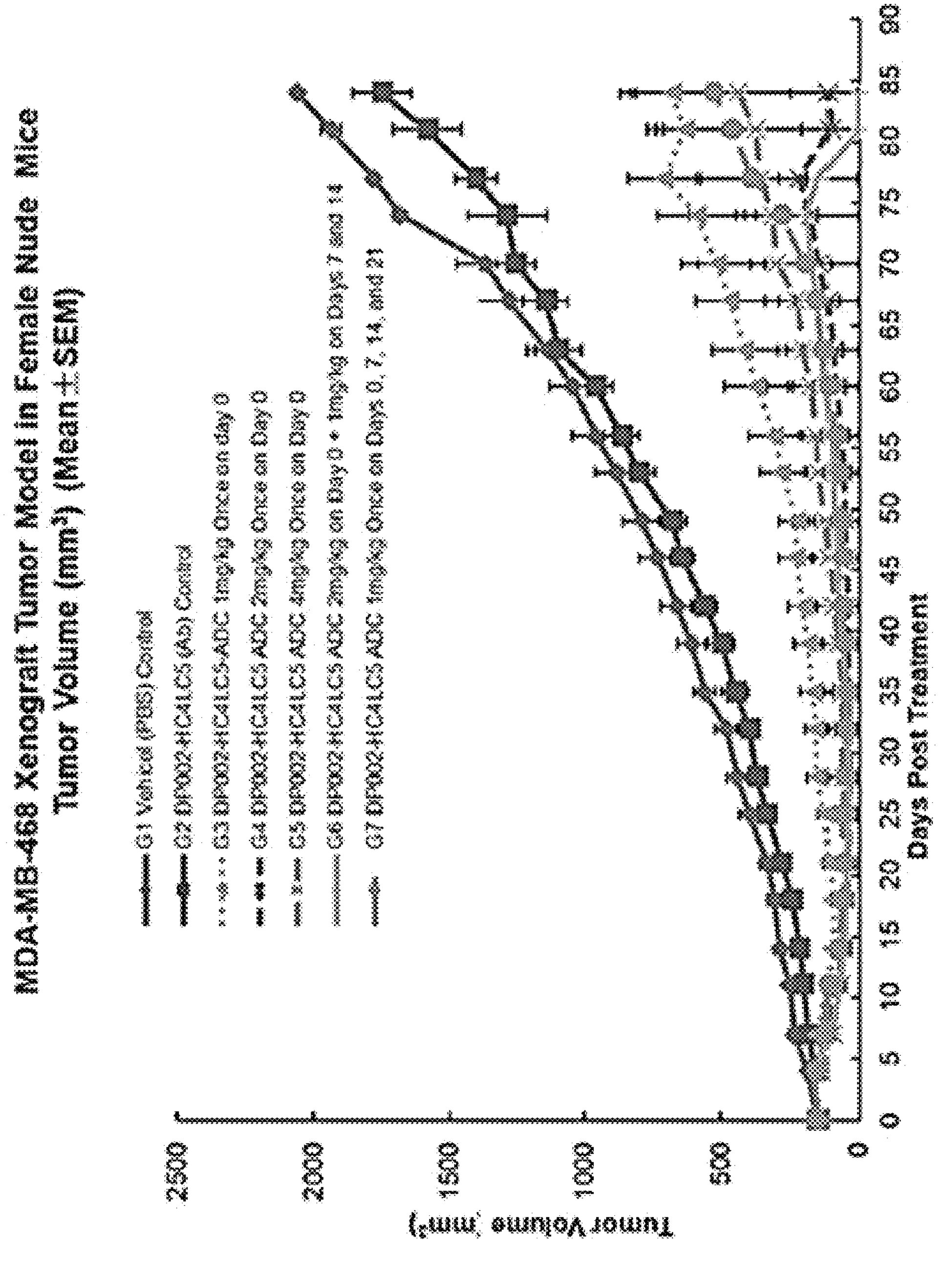
FIG. 5A shows the mean tumor volumes in all xenografted mice as a function of time during treatment with DP002-HC4LC5-ADC at different dosages and/or different administration schedules, vehicle control, or antibody control.
Figure 5B:
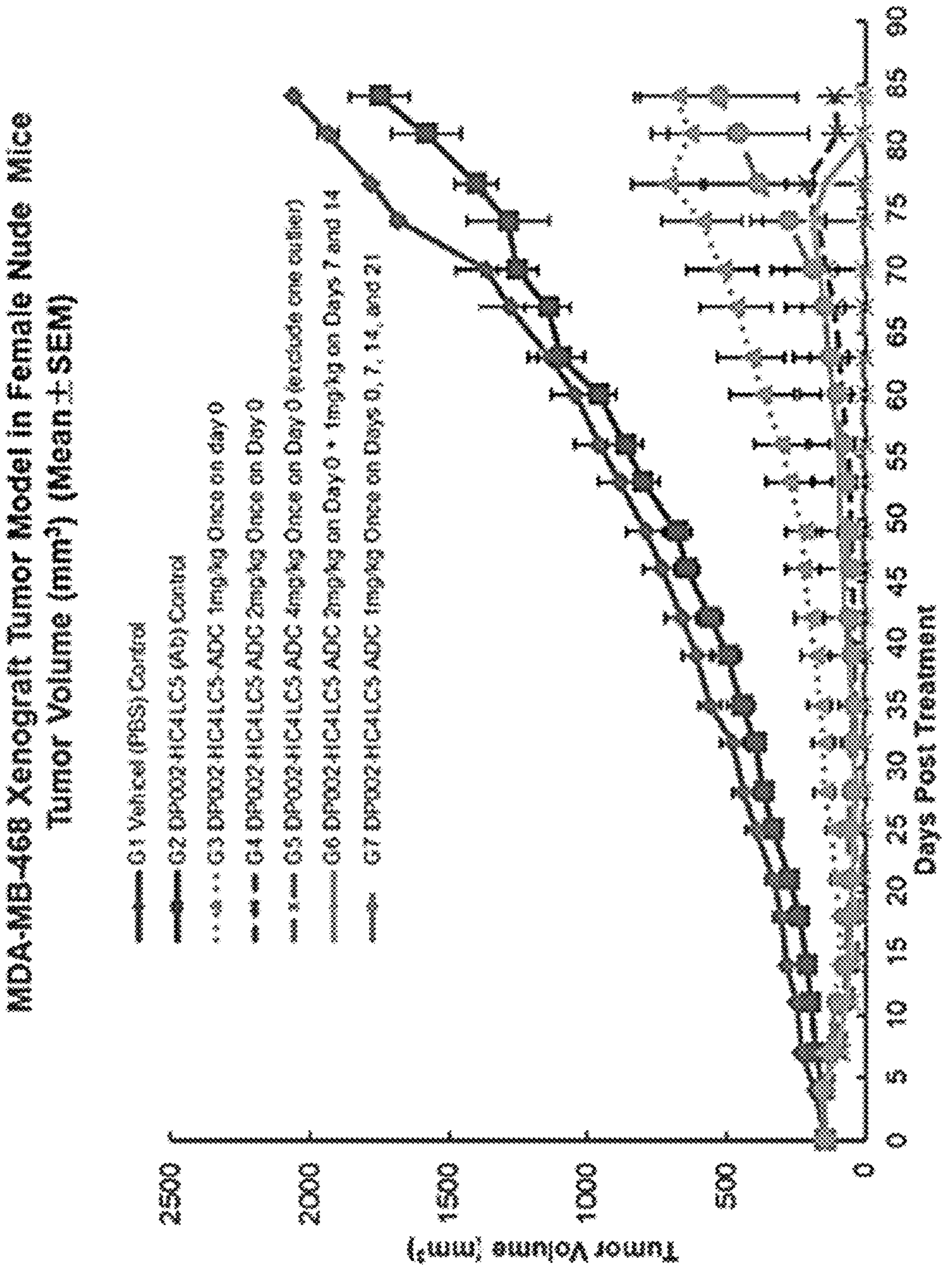
FIG. 5B shows the mean tumor volumes in all xenografted mice except the outlier animal in Group 5 as a function of time during treatment with DP002-HC4LC5-ADC at different dosages and/or different administration schedules, vehicle control, or antibody control.

Treatment with DP002-HC4LC5-ADC resulted in significant inhibition of MDA-MB-468 human breast tumor growth in all groups tested. On Day 70, the average tumor volume of mice in Groups 3, 4, and 5 were 515.77 $mm^3$ (TGI=62.16%, P <0.001), 139.85 $mm^3$ (TGI=89.74%, P<0.001) and 293.26 $mm^3$ (TGI=78.49%, P <0.01), respectively. There appeared an outlier animal in Group 5. Excluding the outlier, the average tumor size of mice in Group 5 on Day 70 was 4.89 $mm^3$, the TGI value for mice in Group 5 on Day 70 was 99.64% (P<0.001). On Day 70, the average tumor volume of mice in Group 6 was 168.94 $mm^3$ (TGI=87.61%, P<0.001), and the average tumor size of mice in Group 7 was 191.51 $mm^3$ (TGI=85.88%, P<0.001). The effects of various treatments on the MDA-MB-468 tumor growth is summarized in Table 14 and FIGS. 5A and 5B. The data in Table 14 and FIGS. 5A and 5B are presented as mean±SEM of n animals. The data in FIG. 5A include the outlier animal in Group 5, whereas the data in FIG. 5B exclude the outlier animal.

TABLE 15

Effect of DP002-HC4LC5-ADC Treaments on Tumor Growth in Mice Bearing xenografted MDA-MB-468 Human Breast Cancer Tumors

| | Tumor Volume ($mm^3$, Mean ± SEM)‡ | | % TGI | Tumor Weight (g, Mean ± SEM) | Tumor Weight (g, Mean ± SEM | Tumor Weight (g, Mean ± SEM |
|---|---|---|---|---|---|---|
| Group | Day 0 | Day 70 | Day 70 | Day 70 | Day 77 | Day 84 |
| 1 | 146.49 ± 8.32 | 1363.16 ± 110.63 | NA | 1.081 ± 0.127 (n = 4) | / | 1.811 ± 0.013 (n = 2) |
| 2 | 147.39 ± 8.98 | 1249.79 ± 70.34 | 8.32% | 1.032 ± 0.073 (n = 4) | / | 1.710 ± 0.058 (n = 2) |
| 3 | 146.98 ± 8.9 | 515.77 ± 127.38*** | 62.16 | / | 0.972 ± 0.165 (n = 2) | 0.658 ± 0.165 (n = 4) |
| 4 | 148.03 ± 8.41 | 139.85 ± 99.80*** | 89.74% | / | 1.004 (n = 1) | 0.089 ± 0.048 (n = 5) |
| 5 | 148.59 ± 7.73 | 293.26 ± 288.40** | 78.49% | / | / | 0.346 ± 0.341 |
| 6 | 148.59 ± 6.61 | 168.94 ± 168.94*** | 87.61% | / | 0.749 (n = 1) | 0.000 ± 0.000 (n = 5) |
| 7 | 146.49 ± 8.32 | 192.51 ± 91.38*** | 85.88% | / | / | 0.421 ± 0.218 |

‡When compared with vehicle group, *indicates that P < 0.05, indicates that P < 0.01, and *indicates that P < 0.001

Complete response (i.e., full tumor regression or remission) was observed in some mice in each of Groups 4-7. Full tumor regression was first observed in week 4 (day 21 or beyond) post the first dosing. At week 11, full regression was observed in 2/6 mice in Group 4; in 4/6 mice in Group 5; in 5/6 mice in Group 6; and in 2/6 mice in Group 7. Full regression was maintained in all mice at study termination (Day 84) except for one mouse in Group 3. Full regression appeared to be related to dose level. The therapeutic effect of administering DP002-HC4LC5-ADC to mice at a dose of 2 mg/kg on Day 0 and 1 mg/kg DP002-HC4LC5-ADC on each of Days 7 and 14 (i.e., Group 6 treatment) was slightly better than the therapeutic effect of administering a single 4 mg/kg dose of DP002-HC4LC5-ADC to mice on Day 0 (i.e., Group 5 treatment). The therapeutic effect of administering 1 mg/kg DP002-HC4LC5-ADC to mice on each of Days 0, 7, 14, and 21 (i.e., Group 7 treatment) was less effective than the Group 5 treatment or the Group 6 treatment. Data regarding full tumor regression in different treatment groups is summarized in Table 15.

TABLE 15

Full Tumor Regression Among Mice in Treatment Groups 1-7 (n = 6 per group unless otherwise specified)

| | Number of mice demonstrating full tumor regression at time point following first dose | | | | | | | | |
|---|---|---|---|---|---|---|---|---|---|
| Treatment Group | Week 4 | Week 5 | Week 6 | Week 7 | Week 8 | Week 9 | Week 10 | Week 11 | Week 12 |
| 1 | 0 | 0 | 0 | 0 | 0 | 0 | 0 | 0 (n = 2) | 0 (n = 2) |
| 2 | 0 | 0 | 0 | 0 | 0 | 0 | 0 | 0 (n = 2) | 0 (n = 2) |
| 3 | 0 | 0 | 0 | 0 | 0 | 0 | 0 | 0 | 0 (n = 4) |
| 4 | 2 | 2 | 2 | 2 | 2 | 2 | 2 | 2 | 1 (n = 5) |

TABLE 15-continued

Full Tumor Regression Among Mice in Treatment Groups 1-7
(n = 6 per group unless otherwise specified)

| Treatment Group | Number of mice demonstrating full tumor regression at time point following first dose | | | | | | | | |
|---|---|---|---|---|---|---|---|---|---|
| | Week 4 | Week 5 | Week 6 | Week 7 | Week 8 | Week 9 | Week 10 | Week 11 | Week 12 |
| 5 | 4 | 4 | 4 | 4 | 4 | 4 | 4 | 4 | 4 |
| 6 | 5 | 5 | 5 | 5 | 5 | 5 | 5 | 5 | 5 (n = 5) |
| 7 | 1 | 1 | 1 | 2 | 2 | 2 | 2 | 2 | 2 |

CONCLUSIONS

DP002-HC4LC5-ADC at a maximum cumulative dose of 4 mg/kg (administered as a single dose on Day 0; as a 2 mg/kg dose on Day 0 and 1 mg/kg doses on each of Days 7 and 14; or as 1 mg/kg doses on each of Days 0, 7, 14, and 21) was well tolerated in mice. No toxicity, significant changes in body weight, or changes in gross observation criteria were observed at this dose level or at the lower cumulative doses of 1 mg/kg or 2 mg/kg. Treatment with DP002-HC4LC5-ADC led to inhibition of MDA-MB-468 tumor growth in all groups tested in a dose-response manner. At the end of the study, treatment tumor regression was observed in 20% of mice given 2 mg/kg DP002-HC4LC5-ADC; in 66% of mice given 4 mg/kg DP002-HC4LC5-ADC as a single dose on Day 0; in 100% of mice given 2 mg/kg DP002-HC4LC5-ADC on Day 0 and 1 mg/kg on each of Days 7 and 14; and in 30% of mice given 1 mg/kg DP002-HC4LC5-ADC on each of Days 0, 7, 14, and 21. By contrast, DP002, the antibody itself, did not possess significant tumor inhibition effects at 4 mg/kg.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

What is claimed is:

1. An anti-Trophoblast cell surface antigen 2 (TROP2) antibody or antigen-binding fragment thereof that specifically binds TROP2, comprising:

i) a CDR-H1 comprising the amino acid sequence of SEQ ID NO: 1; ii) a CDR-H2 comprising the amino acid sequence of SEQ ID NO:39; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19;

or, comprising: i) a CDR-H1 comprising the amino acid sequence of SEQ ID NO:1; ii) a CDR-H2 comprising the amino acid sequence of SEQ ID NO: 5; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19.

2. The anti-TROP2 antibody or antigen-binding fragment thereof of claim 1, comprising a $V_H$ that comprises the amino acid sequence of SEQ ID NO: 22 and a $V_L$ that comprises the amino acid sequence of SEQ ID NO: 27;

or, comprising a $V_H$ comprising the amino acid sequence of SEQ ID NO: 40 and a $V_L$ comprising the amino acid sequence of SEQ ID NO: 46;

or, comprising a $V_H$ comprising the amino acid sequence of SEQ ID NO: 40 and a $V_L$ comprising the amino acid sequence of SEQ ID NO: 48;

or, comprising a $V_H$ comprising the amino acid sequence of SEQ ID NO: 40 and a $V_L$ comprising the amino acid sequence of SEQ ID NO: 49;

or, comprising a $V_H$ comprising the amino acid sequence of SEQ ID NO: 40 and a $V_L$ comprising the amino acid sequence of SEQ ID NO: 50;

or, comprising a $V_H$ comprising the amino acid sequence of SEQ ID NO: 41 and a $V_L$ comprising the amino acid sequence of SEQ ID NO: 46;

or, comprising a $V_H$ comprising the amino acid sequence of SEQ ID NO: 41 and a $V_L$ comprising the amino acid sequence of SEQ ID NO: 48;

or, comprising a $V_H$ comprising the amino acid sequence of SEQ ID NO: 41 and a $V_L$ comprising the amino acid sequence of SEQ ID NO: 49;

or, comprising a $V_H$ comprising the amino acid sequence of SEQ ID NO: 41 and a $V_L$ comprising the amino acid sequence of SEQ ID NO: 50;

or, comprising a $V_H$ comprising the amino acid sequence of SEQ ID NO: 42 and a $V_L$ comprising the amino acid sequence of SEQ ID NO: 46;

or, comprising a $V_H$ comprising the amino acid sequence of SEQ ID NO: 42 and a $V_L$ comprising the amino acid sequence of SEQ ID NO: 48;

or, comprising a $V_H$ comprising the amino acid sequence of SEQ ID NO: 42 and a $V_L$ comprising the amino acid sequence of SEQ ID NO: 49;

or, comprising a $V_H$ comprising the amino acid sequence of SEQ ID NO: 42 and a $V_L$ comprising the amino acid sequence of SEQ ID NO: 50;

or, comprising a $V_H$ comprising the amino acid sequence of SEQ ID NO: 43 and a $V_L$ comprising the amino acid sequence of SEQ ID NO: 46;

or, comprising a $V_H$ comprising the amino acid sequence of SEQ ID NO: 43 and a $V_L$ comprising the amino acid sequence of SEQ ID NO: 48;

or, comprising a $V_H$ comprising the amino acid sequence of SEQ ID NO: 43 and a $V_L$ comprising the amino acid sequence of SEQ ID NO: 49;

or, comprising a $V_H$ comprising the amino acid sequence of SEQ ID NO: 43 and a $V_L$ comprising the amino acid sequence of SEQ ID NO: 50;

or, comprising a $V_H$ comprising the amino acid sequence of SEQ ID NO: 44 and a $V_L$ comprising the amino acid sequence of SEQ ID NO: 46;

or, comprising a $V_H$ comprising the amino acid sequence of SEQ ID NO: 44 and a $V_L$ comprising the amino acid sequence of SEQ ID NO: 48;

or, comprising a $V_H$ comprising the amino acid sequence of SEQ ID NO: 44 and a $V_L$ comprising the amino acid sequence of SEQ ID NO: 49;

or, comprising a $V_H$ comprising the amino acid sequence of SEQ ID NO: 44 and a $V_L$ comprising the amino acid sequence of SEQ ID NO: 50.

3. The anti-TROP2 antibody or antigen-binding fragment thereof of claim 1, comprising an Fc domain.

4. The anti-TROP2 antibody or antigen-binding fragment thereof of claim 3, wherein the Fc domain is a human IgG1, IgG2, IgG3, or IgG4 Fc domain.

5. The anti-TROP2 antibody or antigen-binding fragment thereof of claim 4, wherein the human IgG1 Fc domain comprises the amino acid sequence of SEQ ID NO: 64 or 65.

6. The anti-TROP2 antibody or antigen-binding fragment thereof of claim 1, wherein the anti-TROP2 antibody or antigen binding fragment thereof is chimeric or humanized.

7. The anti-TROP2 antibody or antigen-binding fragment thereof of claim 1, wherein the antigen-binding fragment is selected from the group consisting of a Fab, a Fab', a F(ab)'2, a Fab'-SH, a single-chain Fv (scFv), an Fv fragment, and a linear antibody.

8. An isolated nucleic acid encoding the anti-TROP2 antibody or antigen-binding fragment thereof of claim 1.

9. A vector comprising the nucleic acid of claim 8.

10. A host cell comprising the nucleic acid of claim 8, or a vector comprising a nucleic acid encoding an anti-TROP2 antibody or antigen-binding fragment thereof, wherein the anti-TROP2 antibody or antigen-binding fragment thereof comprises:

i) a CDR-H1 comprising the amino acid sequence of SEQ ID NO: 1; ii) a CDR-H2 comprising the amino acid sequence of SEQ ID NO:39; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19; or, i) a CDR-H1 comprising the amino acid sequence of SEQ ID NO:1; ii) a CDR-H2 comprising the amino acid sequence of SEQ ID NO: 5; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19.

11. A method of producing an anti-TROP2 antibody or antigen-binding fragment thereof, comprising:

a) culturing the host cell of claim 10 under conditions effective to cause expression of the anti-TROP2 antibody or antigen-binding fragment thereof; and b) recovering the anti-TROP2 antibody or antigen-binding fragment thereof expressed by the host cell.

12. An immunoconjugate comprising the anti-TROP2 antibody or antigen-binding fragment thereof according to claim 1 specifically conjugated to a conjugate moiety.

13. The immunoconjugate of claim 12, wherein the conjugate moiety is selected from the group consisting of: a moiety that improves a pharmacokinetic property of the anti-TROP2 antibody or antigen-binding fragment thereof, a therapeutic moiety, a diagnostic moiety, and a label.

14. The immunoconjugate of claim 13, wherein the anti-TROP2 antibody or antigen-binding fragment thereof and the conjugate moiety are conjugated via a linker.

15. The immunoconjugate of claim 14, wherein the linker is a cleavable linker or a non-cleavable linker.

16. The immunoconjugate of claim 13, wherein the anti-TROP2 antibody or antigen-binding fragment thereof is conjugated to the conjugate moiety via an endogenous acceptor glutamine residue on the antibody.

17. The immunoconjugate of claim 13, wherein the conjugate moiety is a therapeutic moiety that comprises a toxin;

or, the conjugate moiety is a label, and wherein the label is selected from the group consisting of: a radioisotope, a fluorescent dye, and an enzyme.

18. The immunoconjugate of claim 17, wherein the toxin is selected from the group consisting of: an auristatin, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides, and conotoxin.

19. The immunoconjugate of claim 18, wherein the toxin is a monomethyl auristatin E (MMAE).

20. A pharmaceutical composition comprising the immunoconjugate of claim 12 and a pharmaceutically acceptable carrier.

21. A method of treating cancer in an individual, comprising administering to the individual an effective amount of an immunoconjugate, or the pharmaceutical composition of claim 20;

wherein the immunoconjugate comprises an anti-TROP2 antibody or antigen-binding fragment thereof specifically conjugated to a conjugate moiety; wherein the conjugate moiety is selected from the group consisting of: a moiety that improves a pharmacokinetic property of the anti-TROP2 antibody or antigen-binding fragment thereof, a therapeutic moiety, a diagnostic moiety, and a label;

wherein the anti-TROP2 antibody or antigen-binding fragment thereof comprises:

i) a CDR-H1 comprising the amino acid sequence of SEQ ID NO: 1; ii) a CDR-H2 comprising the amino acid sequence of SEQ ID NO:39; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19; or, i) a CDR-H1 comprising the amino acid sequence of SEQ ID NO:1; ii) a CDR-H2 comprising the amino acid sequence of SEQ ID NO: 5; iii) a CDR-H3 comprising the amino acid sequence of SEQ ID NO: 10; iv) a CDR-L1 comprising the amino acid sequence of SEQ ID NO: 14; v) a CDR-L2 comprising the amino acid sequence of SEQ ID NO: 17; and vi) a CDR-L3 comprising the amino acid sequence of SEQ ID NO: 19.

22. The method of claim 21, wherein the cancer is selected from solid tumor, breast cancer, cervical cancer, colon cancer, colorectal cancer, endometrioid endometrial cancer (EEC), esophageal cancer, gastric cancer, glioma, lung cancer, Hilar cholangiocarcinoma, squamous cell carcinoma of the oral cavity, small-sized pulmonary adenocarcinoma, ovarian cancer, pancreatic cancer, kidney cancer, prostate cancer, extranodal NK/T-cell lymphoma, nasal type (ENKTL), stomach cancer, thyroid cancer, urinary bladder cancer, or uterine cancer.

23. The method of claim 21, wherein the individual is further administered a therapeutic agent selected from the group consisting of: an anti-neoplastic agent, a chemotherapeutic agent, a growth inhibitory agent and a cytotoxic agent.

24. A method of detecting a TROP2 protein in a sample from an individual comprising contacting the anti-TROP2 antibody or antigen-binding fragment thereof according to claim 1 to the sample, and detecting binding of the anti-TROP2 antibody or antigen-binding fragment thereof to the TROP2 protein.

25. The method according to claim 24, wherein the anti-TROP2 antibody or antigen-binding fragment thereof is used an immunohistochemistry assay (IHC) or in an ELISA assay.

* * * * *